(12) United States Patent
Sharma et al.

(10) Patent No.: US 7,718,802 B2
(45) Date of Patent: May 18, 2010

(54) SUBSTITUTED MELANOCORTIN RECEPTOR-SPECIFIC PIPERAZINE COMPOUNDS

(75) Inventors: Shubh D. Sharma, Cranbury, NJ (US); Yi-Qun Shi, East Brunswick, NJ (US); Ramesh Rajpurohit, Hillsboro, NJ (US); Zhijun Wu, Plainsboro, NJ (US)

(73) Assignee: Palatin Technologies, Inc., Cranbury, NJ (US)

( * ) Notice: Subject to any disclaimer, the term of this patent is extended or adjusted under 35 U.S.C. 154(b) by 978 days.

(21) Appl. No.: 11/099,814

(22) Filed: Apr. 5, 2005

(65) Prior Publication Data
US 2005/0176728 A1 Aug. 11, 2005

Related U.S. Application Data

(63) Continuation-in-part of application No. 10/762,079, filed on Jan. 21, 2004, now Pat. No. 7,354,923, and a continuation-in-part of application No. PCT/US02/25574, filed on Aug. 12, 2002, and a continuation-in-part of application No. 10/837,519, filed on Apr. 30, 2004, now Pat. No. 7,456,184.

(60) Provisional application No. 60/559,741, filed on Apr. 5, 2004, provisional application No. 60/563,739, filed on Apr. 19, 2004, provisional application No. 60/474,497, filed on May 30, 2003, provisional application No. 60/311,404, filed on Aug. 10, 2001, provisional application No. 60/546,393, filed on Feb. 19, 2004, provisional application No. 60/467,442, filed on May 1, 2003, provisional application No. 60/441,139, filed on Jan. 17, 2003.

(51) Int. Cl.
C07D 241/04 (2006.01)
C07D 403/06 (2006.01)
C07D 295/023 (2006.01)

(52) U.S. Cl. ........................ 544/358; 544/359; 544/372; 544/386

(58) Field of Classification Search ................ 544/358, 544/359, 372, 386; 514/252.12, 252.13, 514/254.01
See application file for complete search history.

(56) References Cited

U.S. PATENT DOCUMENTS

| | | | |
|---|---|---|---|
| 4,148,923 A | 4/1979 | Giudicelli et al. | |
| 4,239,763 A | 12/1980 | Milavec et al. | |
| 4,626,549 A | 12/1986 | Molloy et al. | |
| 4,680,289 A | 7/1987 | Applezweig | |
| 4,711,957 A | 12/1987 | Lai | |
| 4,766,125 A | 8/1988 | Van Daele | |
| 4,937,267 A | 6/1990 | Holloway et al. | |
| 4,938,763 A | 7/1990 | Dunn et al. | |
| 4,943,578 A | 7/1990 | Naylor et al. | |
| 4,968,684 A | 11/1990 | Van Daele et al. | |
| 4,997,836 A | 3/1991 | Sugihara et al. | |
| 5,120,713 A | 6/1992 | Mugica | |
| 5,292,726 A | 3/1994 | Ashton et al. | |
| 5,331,573 A | 7/1994 | Balaji et al. | |
| 5,334,830 A | 8/1994 | Fukuyama et al. | |
| 5,348,955 A | 9/1994 | Greenlee et al. | |

(Continued)

FOREIGN PATENT DOCUMENTS

WO WO 96/38471 12/1996

(Continued)

OTHER PUBLICATIONS

U.S. Appl. No. 11/110,060, filed Apr. 2005, Sharma et al.*

(Continued)

*Primary Examiner*—James O Wilson
*Assistant Examiner*—Ebenezer Sackey
(74) *Attorney, Agent, or Firm*—Stephen A. Slusher

(57) ABSTRACT

Melanocortin receptor-specific compounds of the general formulas

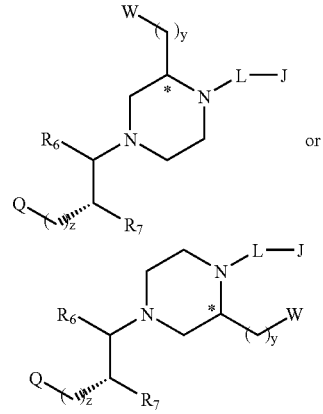

and pharmaceutically acceptable salts thereof, where J is a substituted or unsubstituted monocyclic or bicyclic ring structure, L is a linker, W is a heteroatom unit with at least one cationic center, hydrogen bond donor or hydrogen bond acceptor, Q includes a substituted or unsubstituted aromatic carbocyclic ring, $R_6$, $R_7$, y and z are as defined in the specification, and the carbon atom marked with an asterisk can have any stereochemical configuration, and optionally with one or two additional ring substituents as defined, which compounds bind to one or more melanocortin receptors and are optionally an agonist, a partial agonist, an antagonist, an inverse agonist or an antagonist of an inverse agonist, and may be employed for treatment of one or more melanocortin receptor-associated conditions or disorders, and methods for the use of the compounds of the invention.

34 Claims, No Drawings

U.S. PATENT DOCUMENTS

| | | |
|---|---|---|
| 5,464,788 A | 11/1995 | Bock et al. |
| 5,494,919 A | 2/1996 | Morriello et al. |
| 5,550,131 A | 8/1996 | Sugihara et al. |
| 5,574,031 A | 11/1996 | Abramo et al. |
| 5,579,250 A | 11/1996 | Balaji et al. |
| 5,599,809 A | 2/1997 | Hickey et al. |
| 5,639,778 A | 6/1997 | Andersson et al. |
| 5,672,602 A | 9/1997 | Burkholder et al. |
| 5,721,250 A | 2/1998 | Morriello et al. |
| 5,721,251 A | 2/1998 | Chen et al. |
| 5,736,539 A | 4/1998 | Graham et al. |
| 5,753,445 A | 5/1998 | Fillit et al. |
| 5,753,653 A | 5/1998 | Bender et al. |
| 5,763,445 A | 6/1998 | Kruse et al. |
| 5,798,359 A | 8/1998 | Shue et al. |
| 5,804,578 A | 9/1998 | Chakravarty et al. |
| 5,856,326 A | 1/1999 | Anthony et al. |
| 5,872,262 A | 2/1999 | Dolle et al. |
| 5,877,182 A | 3/1999 | Nargund et al. |
| 5,880,125 A | 3/1999 | Nargund |
| 5,880,128 A | 3/1999 | Doll et al. |
| 5,891,418 A | 4/1999 | Sharma |
| 5,892,038 A | 4/1999 | Dolle et al. |
| 5,936,089 A | 8/1999 | Carpino et al. |
| 5,965,565 A | 10/1999 | Chen et al. |
| 5,968,938 A | 10/1999 | Williams et al. |
| 6,020,334 A | 2/2000 | Fukushi et al. |
| 6,027,711 A | 2/2000 | Sharma |
| 6,033,656 A | 3/2000 | Mikami et al. |
| 6,127,381 A | 10/2000 | Basu et al. |
| 6,127,424 A | 10/2000 | Martin et al. |
| 6,140,354 A | 10/2000 | Dax et al. |
| 6,162,805 A | 12/2000 | Hefti et al. |
| 6,191,117 B1 | 2/2001 | Kozachuk |
| 6,207,665 B1 | 3/2001 | Bauman et al. |
| 6,207,699 B1 | 3/2001 | Rothman |
| 6,214,831 B1 | 4/2001 | Yokoo et al. |
| 6,245,764 B1 | 6/2001 | Kahn et al. |
| 6,284,735 B1 | 9/2001 | Girten et al. |
| 6,294,539 B1 | 9/2001 | Lou et al. |
| 6,303,611 B1 | 10/2001 | Zhang et al. |
| 6,316,470 B1 | 11/2001 | Kover et al. |
| 6,331,285 B1 | 12/2001 | Sharma |
| 6,340,868 B1 | 1/2002 | Lys et al. |
| 6,350,760 B1 | 2/2002 | Bakshi et al. |
| 6,372,747 B1 | 4/2002 | Taveras et al. |
| 6,376,509 B1 | 4/2002 | Bakshi et al. |
| 6,410,548 B2 | 6/2002 | Nargund et al. |
| 6,432,438 B1 | 8/2002 | Shukla |
| 6,432,959 B1 | 8/2002 | Cooper et al. |
| 6,451,783 B1 | 9/2002 | Hadcock et al. |
| 6,458,789 B1 | 10/2002 | Forood et al. |
| 6,458,790 B2 | 10/2002 | Palucki et al. |
| 6,469,006 B1 | 10/2002 | Blair et al. |
| 6,472,398 B1 | 10/2002 | Palucki et al. |
| 6,486,165 B2 | 11/2002 | Zhang et al. |
| 6,515,122 B1 | 2/2003 | Lang et al. |
| 6,531,476 B1 | 3/2003 | Heymans et al. |
| 6,534,503 B1 | 3/2003 | Dines et al. |
| 6,534,509 B1 | 3/2003 | Bauman et al. |
| 6,555,537 B2 | 4/2003 | Bauman et al. |
| 6,569,861 B2 | 5/2003 | Bakthavatchalam et al. |
| 6,579,968 B1 | 6/2003 | Blood et al. |
| 6,612,805 B2 | 9/2003 | Rietsch |
| 6,648,848 B1 | 11/2003 | Keldmann et al. |
| 6,673,767 B1 | 1/2004 | Brodbeck et al. |
| 6,699,873 B1 | 3/2004 | Maguire et al. |
| 6,715,485 B1 | 4/2004 | Djupesland |
| 6,734,175 B2 | 5/2004 | Hadcock et al. |
| 6,811,543 B2 | 11/2004 | Keldmann et al. |
| 6,949,552 B2 | 9/2005 | Nakazato et al. |
| 7,326,707 B2 | 2/2008 | Sharma et al. |
| 7,354,923 B2 | 4/2008 | Sharma et al. |
| 7,456,184 B2 | 11/2008 | Sharma et al. |
| 2001/0018075 A1 | 8/2001 | Shigeyuki et al. |
| 2001/0047001 A1 | 11/2001 | Varkhedkar et al. |
| 2002/0004512 A1 | 1/2002 | Bakshi et al. |
| 2002/0010182 A1 | 1/2002 | Masaaki et al. |
| 2002/0019523 A1 | 2/2002 | Palucki et al. |
| 2002/0022620 A1 | 2/2002 | Kahn et al. |
| 2002/0032238 A1 | 3/2002 | Priepke et al. |
| 2002/0037837 A1 | 3/2002 | Takada et al. |
| 2002/0042399 A1 | 4/2002 | Kruse et al. |
| 2002/0052383 A1 | 5/2002 | Bakthavatchalam et al. |
| 2002/0065277 A1 | 5/2002 | Hadcock et al. |
| 2002/0065416 A1 | 5/2002 | Stasiak et al. |
| 2002/0072604 A1 | 6/2002 | Carpino et al. |
| 2002/0082263 A1 | 6/2002 | Lou et al. |
| 2002/0107253 A1 | 8/2002 | Koh et al. |
| 2002/0107255 A1 | 8/2002 | Blumberg et al. |
| 2002/0128247 A1 | 9/2002 | Dow et al. |
| 2002/0128270 A1 | 9/2002 | Neya et al. |
| 2002/0137664 A1 | 9/2002 | Bakshi et al. |
| 2002/0143141 A1 | 10/2002 | Chen et al. |
| 2002/0173512 A1 | 11/2002 | Moltzen et al. |
| 2002/0177598 A1 | 11/2002 | Bauman et al. |
| 2002/0183316 A1 | 12/2002 | Pan et al. |
| 2003/0004162 A1 | 1/2003 | Treadway |
| 2003/0013721 A1 | 1/2003 | Meghani et al. |
| 2003/0040520 A1 | 2/2003 | Guzi et al. |
| 2003/0055008 A1 | 3/2003 | Marcotte |
| 2003/0055009 A1 | 3/2003 | Steiner et al. |
| 2003/0055247 A1 | 3/2003 | Cosford et al. |
| 2003/0055265 A1 | 3/2003 | Binggeli et al. |
| 2003/0060473 A1 | 3/2003 | Neya et al. |
| 2003/0064921 A1 | 4/2003 | Millhauser et al. |
| 2003/0069169 A1 | 4/2003 | Macor et al. |
| 2003/0083228 A1 | 5/2003 | Carpino et al. |
| 2003/0083335 A1 | 5/2003 | Hayward |
| 2003/0092732 A1 | 5/2003 | Yu et al. |
| 2003/0096827 A1 | 5/2003 | Yu et al. |
| 2003/0105106 A1 | 6/2003 | Chiang et al. |
| 2003/0109556 A1 | 6/2003 | Mazur et al. |
| 2003/0125334 A1 | 7/2003 | Chiang et al. |
| 2003/0139425 A1 | 7/2003 | Bauman et al. |
| 2003/0144277 A1 | 7/2003 | DeLucca |
| 2003/0149019 A1 | 8/2003 | Bremberg et al. |
| 2003/0158205 A1 | 8/2003 | Bauman et al. |
| 2003/0158209 A1 | 8/2003 | Dyck et al. |
| 2003/0162819 A1 | 8/2003 | Eisinger et al. |
| 2003/0166637 A1 | 9/2003 | Lehmann-Lintz et al. |
| 2003/0176425 A1 | 9/2003 | Eisinger et al. |
| 2003/0181441 A1 | 9/2003 | McClure et al. |
| 2003/0191136 A1 | 10/2003 | Bakthavatchalam et al. |
| 2003/0195212 A1 | 10/2003 | Lundstedt et al. |
| 2004/0006067 A1 | 1/2004 | Fotsch et al. |
| 2004/0024211 A1 | 2/2004 | Boyce et al. |
| 2004/0034034 A1 | 2/2004 | Blumberg et al. |
| 2004/0053933 A1 | 3/2004 | Pontillo et al. |
| 2004/0147567 A1 | 7/2004 | Nakazato et al. |
| 2004/0152534 A1 | 8/2004 | Chapman et al. |
| 2004/0157264 A1 | 8/2004 | Sharma et al. |
| 2004/0171520 A1 | 9/2004 | Sharma et al. |
| 2004/0204398 A1 | 10/2004 | Bakshi et al. |
| 2004/0224957 A1 | 11/2004 | Sharma et al. |
| 2004/0254198 A1 | 12/2004 | Reynolds et al. |
| 2005/0124636 A1 | 6/2005 | Sharma et al. |
| 2005/0130988 A1 | 6/2005 | Sharma et al. |
| 2005/0176728 A1 | 8/2005 | Sharma et al. |
| 2006/0009456 A1 | 1/2006 | Hutchinson et al. |
| 2006/0084657 A1 | 4/2006 | Nakazato et al. |
| 2006/0287330 A1 | 12/2006 | Sharma et al. |
| 2006/0287331 A1 | 12/2006 | Sharma et al. |
| 2006/0287332 A1 | 12/2006 | Sharma et al. |

| | | |
|---|---|---|
| 2008/0070921 A1 | 3/2008 | Burris et al. |
| 2008/0234289 A1 | 9/2008 | Sharma et al. |
| 2009/0076029 A1 | 3/2009 | Sharma et al. |

FOREIGN PATENT DOCUMENTS

| | | |
|---|---|---|
| WO | WO 97/46553 | 12/1997 |
| WO | WO 98/10653 | 3/1998 |
| WO | WO 98/17625 | 4/1998 |
| WO | WO 99/55679 | 11/1999 |
| WO | WO 99/58501 | 11/1999 |
| WO | WO 99/64002 | 12/1999 |
| WO | WO 00/01726 | 1/2000 |
| WO | WO 00/05373 | 2/2000 |
| WO | WO 00/17348 | 3/2000 |
| WO | WO 00/35952 | 6/2000 |
| WO | WO 00/36136 | 6/2000 |
| WO | WO 00/40247 | 7/2000 |
| WO | WO 00/53148 | 9/2000 |
| WO | WO 00/68185 | 11/2000 |
| WO | WO 00/74679 | 12/2000 |
| WO | WO 01/05401 | 1/2001 |
| WO | WO 01/10842 | 2/2001 |
| WO | WO 01/12176 | 2/2001 |
| WO | WO 01/13112 | 2/2001 |
| WO | WO 01/18210 | 3/2001 |
| WO | WO 01/21634 | 3/2001 |
| WO | WO 01/21647 | 3/2001 |
| WO | WO 01/23392 | 4/2001 |
| WO | WO 01/30343 | 5/2001 |
| WO | WO 01/30808 | 5/2001 |
| WO | WO 01/35970 | 5/2001 |
| WO | WO 01/52880 | 7/2001 |
| WO | WO 01/55106 | 8/2001 |
| WO | WO 01/55107 | 8/2001 |
| WO | WO 01/55109 | 8/2001 |
| WO | WO 01/70708 | 9/2001 |
| WO | WO 01/91752 | 12/2001 |
| WO | WO 02/00259 | 1/2002 |
| WO | WO 02/00654 | 1/2002 |
| WO | WO 02/12178 | 2/2002 |
| WO | WO 02/15909 | 2/2002 |
| WO | WO 02/18437 | 3/2002 |
| WO | WO 02/47670 | 6/2002 |
| WO | WO 02/059095 | 8/2002 |
| WO | WO 02/059107 | 8/2002 |
| WO | WO 02/059108 | 8/2002 |
| WO | WO 02/059117 | 8/2002 |
| WO | WO 02/062766 | 8/2002 |
| WO | WO 02/064091 | 8/2002 |
| WO | WO 02/064734 | 8/2002 |
| WO | WO 02/067869 | 9/2002 |
| WO | WO 02/068387 | 9/2002 |
| WO | WO 02/068388 | 9/2002 |
| WO | WO 02/069905 | 9/2002 |
| WO | WO 02/070511 | 9/2002 |
| WO | WO 02/079146 | 10/2002 |
| WO | WO 02/079203 | 10/2002 |
| WO | WO 02/079753 | 10/2002 |
| WO | WO 02/081443 | 10/2002 |
| WO | WO 02/085925 | 10/2002 |
| WO | WO 02/092566 | 11/2002 |
| WO | WO 03/006620 | 1/2003 |
| WO | WO 03/007949 | 1/2003 |
| WO | WO 03/009847 | 2/2003 |
| WO | WO 03/009850 | 2/2003 |
| WO | WO 03/013509 | 2/2003 |
| WO | WO 03/013571 | 2/2003 |
| WO | WO 03/020724 | 3/2003 |
| WO | WO 03/027239 | 4/2003 |
| WO | WO 03/031410 | 4/2003 |
| WO | WO 03/045920 | 6/2003 |
| WO | WO 03/053927 | 7/2003 |
| WO | WO 03/055477 | 7/2003 |
| WO | WO 03/061660 | 7/2003 |
| WO | WO 03/066587 | 8/2003 |
| WO | WO 03/066597 | 8/2003 |
| WO | WO 03/072056 | 9/2003 |
| WO | WO 03/092690 | 11/2003 |
| WO | WO 03/093234 | 11/2003 |
| WO | WO 03/094918 | 11/2003 |
| WO | WO 2004/037796 | 5/2004 |
| WO | WO 2005/102340 | 11/2005 |
| WO | WO 2006/014552 | 2/2006 |
| WO | WO 2007/021990 | 2/2007 |
| WO | WO 2007/021991 | 2/2007 |

OTHER PUBLICATIONS

U.S. Appl. No. 12/130,299, filed May 30, 2008, Burris et al.
U.S. Appl. No. 12/130,316, filed May 30, 2008, Sharma et al.
Abou-Gharbia et al. "Synthesis and SAR of Adatanserin: Novel Adamantyl Aryl- and Heteroarylpiperazines with Dual Serotonin 5-HT$_{1A}$ and 5-HT$_2$ Activity as Potential Anxiolytic and Antidepressant Agents" J. Med. Chem. 42(25):5077-5094 (1999).
Adan et al. "Inverse agonism gains weight" Trends in Pharmacological Sciences 24(6):315-321 (2003).
Alterman et al. "Design and synthesis of new potent C2-symmetric HIV-1 protease inhibitors. Use of L-mannaric acid as a peptidomimetic scaffold" J. Med. Chem. 41:3782-3792 (1998).
Baldwin et al. "Synthesis of a bicyclic γ-lactam dipeptide analogue" Tetrahedron Letters 34(10):1665-1668 (1993).
Chang et al. "Morphiceptin (NH4-tyr-pro-phe-pro-COHN2): a potent and specific agonist for morphine (mu) receptors" Science 212(4490):75-77 (1981).
Cho et al. "Discovery of novel, potent and orally active nonpeptide antagonist of the human luteinizing hormone-releasing hormone (LHRH) receptor" J. Med. Chem. 41:4190-4195 (1998).
Chorev et al. "Toward nonpeptidal substance P mimetic analogues: Design, synthesis, and biological activity" Biopolymers 31(6):725-733 (1991).
Cornille et al. "Anodic amide oxidations: Conformationally restricted peptide building blocks from the direct oxidation of dipeptides" Tetrahedron Letters 35(38):6989-6992 (1994).
DiMaio et al. "Synthesis of chiral piperazin-2-ones as model peptidomimetics" J Chem. Soc., Perkin Trans I, 1687-1689 (1989).
Gante "Peptidomimetics—Tailored enzyme-inhibitors" Angewandte Chemie International Edition in English 33(17):1699-1720 (1994).
Giannis et al. "Peptidomimetics in drug design" Advances in Drug Research 29:1-78 (1997).
Hadley et al. "Discovery and development of novel melanogenic drugs. Melanotan-I and -II" Ronald. T. Borchardt, et al. editors; Integration of Pharmaceutical Discovery and Development: Case Histories, Plenum Press, New York, 575-595 (1998).
Haskell-Luevano et al. "Discovery of Prototype Peptidomimetic Agonists at the Human Melanocortin Receptors MC1R and MC4R" J. Med. Chem. 40:2133-2139 (1997).
Hruby et al. "Molecular organization of receptors —Efficacy, agonists, and antagonists" Annals of the New York Academy of Sciences 757:7-22 (1995).
Jones et al. "Clinically validated peptides as templates for de novo peptidomimetic drug design at G-protein coupled receptors" Current Opinion in Pharmacology 3:530-543 (2003).
Kask et al. "Discovery of a novel superpotent and selective melanocortin-4 receptor antagonist (HS024): Evaluation in vitro and in vivo" Endocrinology 139(12):5006-5014 (1998).
Kim et al. "Synthesis of (3R)-carboxy pyrrolidine (a β-proline analogue) and its oligomer" Bioorganic & Medicinal Chemistry Letters 10(21):2417-2419 (2000).
Klein et al. "O-benzyl hydroxyproline as a bioisostere for Phe-Pro: Novel dipeptide thrombin inhibitors" Bioorganic & Medicinal Chemistry Letters 6(18):2225-2230 (1996).
Lerner et al. "Synthetic melanocortin receptor. Agonist and antagonists" Cutaneous Neuroimmunomodulation: The Proopiomelanocortin System, Annals of the New York Academy of Sciences 885:153-160 (1995).

Medical Encyclopaedia: Female sexual dysfunction [online]. Retrieved on Oct. 10, 2007 from http://www.nlm.nih.gov/medlineplus/ency/article/003151.htm.

Mitsunobu "The use of diethyl azodicarboxylate and triphenylphosphine in synthesis and transfromation of natural products" Synthesis 1:1-28 (1981).

Moore et al. "A rapid screening system to determine drug affinities for the instestinal dipeptide transporter 2: Affinities of ACE inhibitors" International Journal of Pharmaceutics 210: 29-44 (2000).

Moore et al. "Designing Peptide Mimetics" Trends Pharmacol. Sci. 15:124-129 (1994).

Rarey et al. "Similarity searching in large combinatorial chemistry spaces" J. Computer-Aided Mol. Des. 15(6):497-520 (2001).

Rubsam et al. "Synthesis of chiral piperazinones as versatile scaffolds for peptidomimetics" Tetrahedron 56(43):8481-8487 (2000).

Sasaki et al. "Discovery of a thieno[2,3-d]pyrimidine-2,4-dione bearing a p-methoxyureidophenyl moiety at the 6-position: A highly potent and orally bioavailable non-peptide antagonist for the human luteinizing hormone-releasing hormone receptor" J. Med. Chem. 46:113-124 (2003).

Schioth et al. "Pharmacological comparison of rat and human melanocortin 3 and 4 receptors in vitro" Regulatory Peptides 106:7-12 (2002).

Shvachkin et al. "Synthesis of analogs of the thyrotropin-releasing hormone" Journal of General Chemistry of the USSR in English Translation 43(3):686-687 (1973).

Stavropoulos et al. "Synthesis of cis-4-hydroxy-L-proline and its incorporation into biologically important peptides" Review of Clinical Pharmacology and Pharmacokinetics 103-106 (1995).

Sudoh et al. "Transport characteristics of peptidomimetics. Effect of the pyrrolinone bioisostere of transport across caco-2 cell monolayers" Pharmaceutical Research 15(5):719-725 (1998).

Takenaka et al. "Synthesis of met- and leu-enkephalin analogues containing chiral N,N-ethylene-bridged phenylalanyl-methionine and -leucine" J Chem. Soc., Perkin Trans I, 8:933-937 (1993).

Torres et al. "Neoglycopeptide synthesis and purification in multigram scale: preparation of O-(2,3,4,6-tetra-O-acetyl-beta-D-galactopyranosyl)-N alpha-fluoren-9-yl-methoxycarbonyl-hydroxyproline and its use in the pilot-scale synthesis of the potent analgesic glycopeptide O1.5-beta-D-galactopyranosyl [DMet2, Hyp5]enkephalinamide." Journal of Peptide Science 3(2):99-109 (1997).

Torres et al. "Synthesis and conformational analysis of a series of galactosyl enkephalin analogues showing high analgesic activity" The EMBO Journal 8(10):2925-2932 (1989).

Yamamoto "Synthesis and adhesive studies of marine polypeptides" J. Chem. Soc., Perkin Trans I, 3:613-618 (1987).

Zhorov et al. "Similarity of Ca2+-bound conformations of morphine and Met-enkephalin: A computational study" FEBS Letters 354(2):131-134 (1994).

Cachexia [online], retrieved on Nov. 19, 2009 from the internet (URL: http://en.wikipedia.org/wiki/Cachexia)

Inui "Cancer anorexia-cachexia syndrome: Current issues in research and management" CA A Cancer Journal for Clinicians 52:72-91 (2002).

*Synthetic Peptides: A User's Guide*, GA Grant, editor, W.H. Freeman & Co., New York, 1992, the teachings of which are incorporated herein by reference, includings the text and table set forth at pp. 11 through 24.

Hruby VJ, Al-obeidi F and Kazrnierski W: *Biochem J*268:249-262, 1990.

Toniolo C: *Int J Peptide Protein.Res* 35:287-300, 1990.

R.T. Dorr et al., Evaluation of Melanota-II, A Superpotent Cyclic Melanotropic Peptide in a Pilot Phase-I Clinical Study. *Life Sci.* 58:1777-1784 (1996).

R.A.H. Adan, Identification of Antagonists for Melanocortin MC3, MC4, and MC5 Receptors. *Eur. J. Pharmacol.*, 269;331-337 (1994).

Fan et al. "Role of melanocortinergic neurons in feeding and the agouti obesity syndrome" Nature 385(6612):165-168 (1997).

Holder et al. "Melanocortin ligands: 30 years of structure-activity relationship (SAR) studies" Medicinal Research Reviews 24(3): 325-356 (2004).

Hruby et al. "Synthesis of oligopeptide and peptidomimetic libraries" Current Opinion in Chemical Biology 1(1): 114-119 (1997).

* cited by examiner

SUBSTITUTED MELANOCORTIN RECEPTOR-SPECIFIC PIPERAZINE COMPOUNDS

CROSS-REFERENCE TO RELATED APPLICATION

This application is a continuation-in-part application of U.S. patent application Ser. No. 10/762,079, entitled "Piperazine Melanocortin-Specific Compounds", filed on Jan. 21, 2004, which claimed priority to U.S. Provisional Patent Application Ser. No. 60/474,497, entitled "Substituted Piperazine Compounds Specific for Melanocortin Receptors", filed on May 30, 2003 and U.S. Provisional Patent Application Ser. No. 60/441,139, entitled "Ring Core Compounds Specific for Melanocortin Receptors", filed on Jan. 17, 2003, and which in turn was a continuation-in-part application of International Application No. PCT/US02/25574, International Publication No. WO 03/013571, entitled "Peptidomimetics of Biologically Active Metallopeptides", filed on Aug. 12, 2002, which claimed priority to U.S. Provisional Patent Application Ser. No. 60/311,404, entitled "Receptor-Specific Peptides Derived from Biologically Active Metallopeptides", filed on Aug. 10, 2001. This application is also a continuation-in-part application of U.S. patent application Ser. No. 10/837,519, entitled "Melanocortin Receptor-Specific Compounds", filed on Apr. 30, 2004, which claimed priority to U.S. Provisional Patent Application Ser. No. 60/546,393, entitled "Melanocortin Receptor-Specific Tetra-Substituted Piperazine Compounds", filed on Feb. 19, 2004, and U.S. Provisional Patent Application Ser. No. 60/467,442, entitled "Tetra-, Penta- and Hexa-Substituted Piperazine Compounds and Derivatives", filed on May 1, 2003. The specification of each of the foregoing patent applications, including international applications and provisional applications, is incorporated herein by reference.

This application claims the benefit of the filing of U.S. Provisional Patent Application 60/559,741, entitled "Substituted Melanocortin-Receptor-Specific Piperazine Compounds", filed on Apr. 5, 2004, and of U.S. Provisional Patent Application 60/563,739, entitled "Substituted Melanocortin Receptor-Specific Ketopiperazine Compounds", filed on Apr. 19, 2004, and the specification thereof of each is incorporated herein by reference.

BACKGROUND OF THE INVENTION

1. Field of the Invention (Technical Field)

The present invention relates to tri-, tetra- and penta-substituted piperazine compounds that bind to one or more melanocortin receptors and are agonists, antagonists, mixed agonist-antagonists, inverse agonist or antagonists of inverse agonists with respect to one or more melanocortin receptors, and use thereof for the treatment of metabolic, immune, infection-related and melanocortin receptor mediated disorders.

2. Background Art

A family of melanocortin receptor types and subtypes have been identified, including melanocortin-1 receptors (MC1-R) expressed on normal human melanocytes and melanoma cells, melanocortin-2 receptors (MC2-R) for ACTH (adrenocorticotropin) expressed in cells of the adrenal gland, melanocortin-3 and melanocortin-4 receptors (MC3-R and MC4-R), expressed primarily in cells in the hypothalamus, midbrain and brainstem, and melanocortin-5 receptors (MC5-R), expressed in a wide distribution of tissues.

In general, compounds specific for MC1-R are believed to be useful for treatment of melanoma. Compounds specific for MC3-R or MC4-R are believed to be useful in regulation of energy homeostasis, including use as agents for attenuating food intake and body weight gain, for use in treatment of anorexia, as a weight gain aid, for treatment of obesity, and treatment of other food intake and metabolism-related purposes. Compounds specific for MC3-R and MC4-R can further be used as agents for treatment of sexual dysfunction, including male erectile dysfunction and female sexual dysfunction. Other melanocortin receptor-specific compounds, such as MCR-1 agonists, can be used as tanning agents to increase melanin production in the skin, acting as chemopreventive agents against harmful effects of UV solar radiation. Compounds specific for MCR-1 and MCR-3 may further be useful in regulation of inflammatory processes.

There is a significant need for compounds with high specificity for discrete melanocortin receptors, as well as for compounds that are either agonists or antagonists for specific melanocortin receptors. High affinity compounds for melanocortin receptors can be used to exploit varied physiological responses associated with the melanocortin receptors, either as agonists or antagonists. In addition, melanocortin receptors have an effect on the activity of various cytokines, and high affinity compounds for melanocortin receptors can be used to regulate cytokine activity.

There are piperazine and piperidine compounds known, such as those disclosed in WO 02/070511 (Bristol-Myers Squibb Company), WO 02/059095 (Eli Lilly and Company), and WO 00/74679 (Merck & Co., Inc.), asserted to be specific for melanocortin or related receptors. However, in general such compounds have at most two functional substituted groups, have relatively poor affinity and specificity, and are not suitable for use as a drug compound. There is a significant need for compounds with high specificity for discrete receptors, such as melanocortin and other receptors, as well as compounds that are agonists or antagonists for such receptors. High affinity compounds for such receptors can be used to exploit varied physiological responses associated with the receptors, either as agonists or antagonists. There is thus a need for compounds that are more selective, including higher affinity and specificity, and in particular for compounds that have at least three or four biologically active substituted groups. This invention addresses that need.

WO 02/085925, "Melanocortin Receptor Ligands", to The Proctor & Gamble Company, discloses ketopiperazine structures and methods of synthesis thereof, but does not disclose piperazine structures, piperazine structures with four or more substituted groups, methods to synthesize piperazine structures, methods to synthesize piperazine structures with four or more substituted groups, or methods to synthesize optically pure structures, and further does not disclose structures with a single substituent group that is a single D-Phe residue, or a derivative or homolog thereof, optionally with an amine capping group.

With respect to certain objects, methods, synthetic schemes, utilities, applications, definitions, protocols and other disclosures, this application is related to U.S. patent application Ser. No. 10/762,079, entitled "Piperazine Melanocortin-Specific Compounds", filed on Jan. 21, 2004; U.S. patent application Ser. No. 10/837,519, entitled "Melanocortin Receptor-Specific Compounds", filed on Apr. 30, 2004; International Application No. PCT/US02/25574, International Publication No. WO 03/013571, entitled "Peptidomimetics of Biologically Active Metallopeptides", filed on Aug. 12, 2002; and the specifications of each of the foregoing are incorporated herein by reference as if set forth in full.

SUMMARY OF THE INVENTION

In one embodiment, the invention provides a tri-substituted melanocortin receptor-specific piperazine compound having the structure I or II:

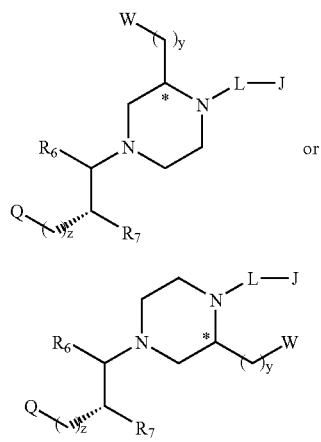

and pharmaceutically acceptable salts thereof;
wherein
J is a substituted or unsubstituted monocyclic or bicyclic ring structure, wherein in each instance the ring or rings have 5 or 6 ring atoms;
L is a linker selected from the group consisting of:
—$(CH_2)_q$—,
—$(CH_2)_q$—O—,
—$(CH_2)_q$—O—(C=O)—,
—$(CH_2)_q$—NH—,
—$(CH_2)_q$—NH—(C=O)—,
—$(CH_2)_q$—(C=O)—NH—,
—$(CH_2)_q$—(C=O)—O—,
—NH—(C=O)—$(CH_2)_q$—,
—(C=O)—NH—$(CH_2)_q$—,
—NH—$(CH_2)_q$—,
—NH—$(CH_2)_q$—O—,
—(C=O)$(CH_2)_q$—,
—$(CH_2)_q$—(C=O)— and
—(C=O)—O—$(CH_2)_q$—,
where q is from 0 to 6;
W is a heteroatom unit with at least one cationic center, hydrogen bond donor or hydrogen bond acceptor;
Q includes a substituted or unsubstituted aromatic carbocyclic ring;
$R_6$ is H, =O, =S or $CH_3$;

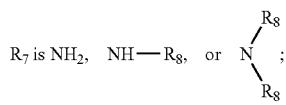

$R_8$ is a $C_1$ to $C_6$ linear or branched chain or an amine capping group, and where there are two $R_8$ groups, each $R_8$ is independently a $C_1$ to $C_6$ linear or branched chain or an amine capping group;
y is from 0 to 6;
z is from 0 to 6; and
wherein the carbon atom marked with an asterisk can have any stereochemical configuration.

In one preferred embodiment, $R_6$ is H or =O.
In another preferred embodiment, $R_7$ is $NH_2$, $N(CH_3)_2$,

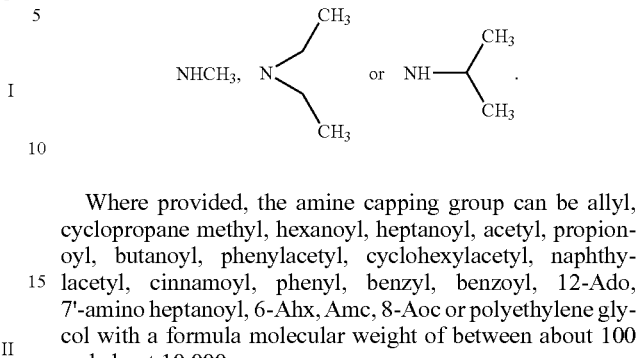

Where provided, the amine capping group can be allyl, cyclopropane methyl, hexanoyl, heptanoyl, acetyl, propionoyl, butanoyl, phenylacetyl, cyclohexylacetyl, naphthylacetyl, cinnamoyl, phenyl, benzyl, benzoyl, 12-Ado, 7'-amino heptanoyl, 6-Ahx, Amc, 8-Aoc or polyethylene glycol with a formula molecular weight of between about 100 and about 10,000.

In one preferred embodiment, L is —$CH_2$—, —$(CH_2)_2$—, or —(C=O)$(CH_2)_2$—.

J may be a substituted or unsubstituted ring structure selected from the group consisting of:

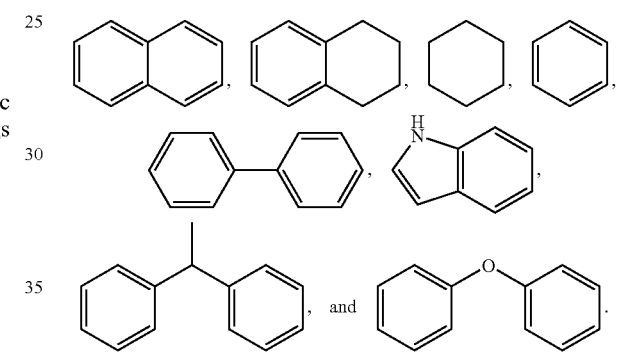

Where J is one of the foregoing, J may be substituted at one or more positions with one or more hydroxyl, halogen, alkyl or aryl groups.

W may be is a cationic center selected from the group consisting of —$NH_2$ and —NH(C=NH)$NH_2$. Alternatively, W may be a cationic center, hydrogen bond donor or hydrogen bond acceptor selected from the group consisting of:
—$NHCOCH_3$,
—$CONHCH_3$,
—NH(C=NH)NHMe,
—NH(C=NH)NHEt,
—NH(C=NH)NHPr,
—NH(C=NH)NHPr—I,
—NH(C=NH)$NH_2$,
—NH(C=O)$OCH_3$,
—NH(C=O)$CH_3$,
—NH(C=O)$NH_2$,
—NH(C=O)$NHCH_3$,

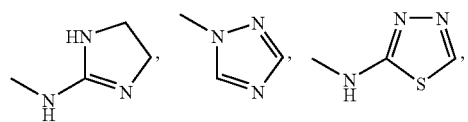

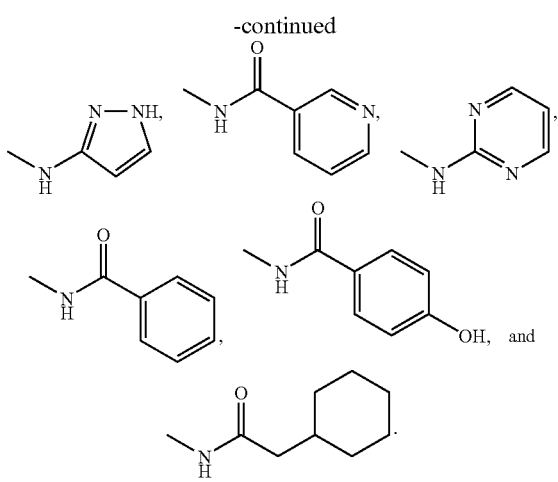

Q may be phenyl, substituted phenyl, naphthyl or substituted naphthyl. Alternatively, Q may be an indole, substituted indole, quinoline, substituted quinoline, isoquinoline or substituted isoquinoline. Where Q is phenyl or substituted phenyl, Q may be

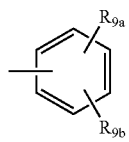

where $R_{9a}$ and $R_{9b}$ are optional ring substituents, and when one or both are present, are the same or different and independently hydroxyl, halogen, alkyl, or aryl groups attached directly or through an ether linkage.

In a second embodiment, the invention provides a tetra-substituted melanocortin receptor-specific piperazine compound having the structure III or IV:

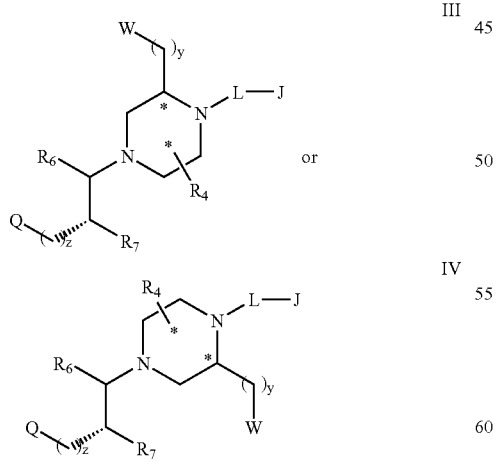

and pharmaceutically acceptable salts thereof; wherein J, L, W, Q, $R_6$, $R_7$, y and z are as defined for compounds I and II, $R_4$ is a $C_1$ to $C_6$ linear or branched chain, a $C_1$ to $C_6$ linear or branched chain with an aryl group, or a $C_1$ to $C_6$ linear or branched chain with a heteroatom unit containing at least one cationic center, hydrogen bond donor or hydrogen bond acceptor, and wherein the carbon atoms marked with an asterisk can have any stereochemical configuration.

It may thus be seen that compounds III and IV includes compounds with the following structures:

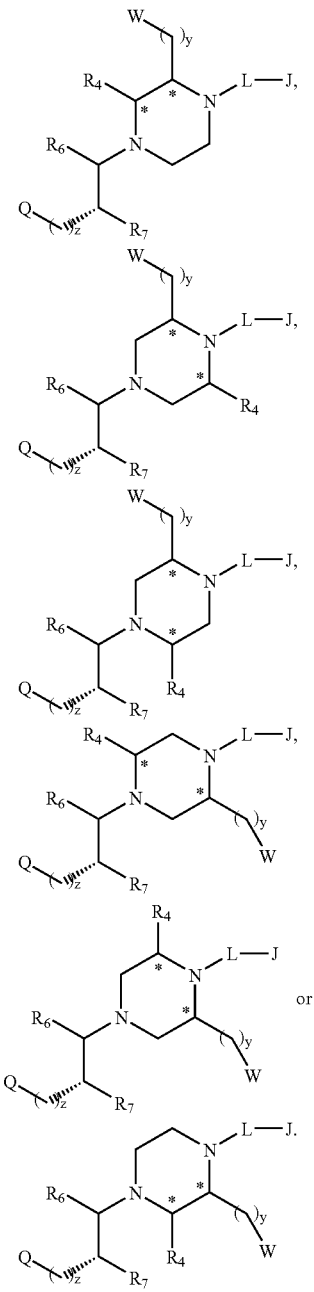

In one preferred embodiment, $R_4$ is $CH_3$,

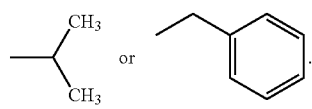

In a third embodiment, the invention provides a penta-substituted melanocortin receptor-specific piperazine compound having the structure V or VI:

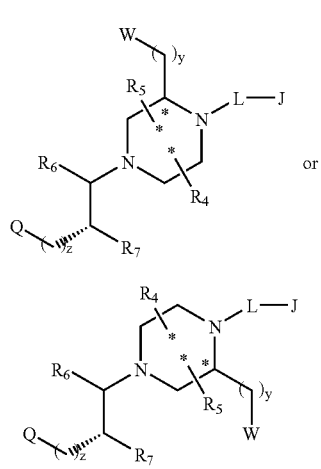

and pharmaceutically acceptable salts thereof; wherein J, L, W, Q, $R_6$, $R_7$, y and z are as defined for compounds I and II, $R_4$ and $R_5$ are each independently a $C_1$ to $C_6$ linear or branched chain, a $C_1$ to $C_6$ linear or branched chain with an aryl group, or a $C_1$ to $C_6$ linear or branched chain with a heteroatom unit containing at least one cationic center, hydrogen bond donor or hydrogen bond acceptor, and wherein the carbon atoms marked with an asterisk can have any stereochemical configuration.

It may thus be seen that compounds V and VI includes compounds with the following structures:

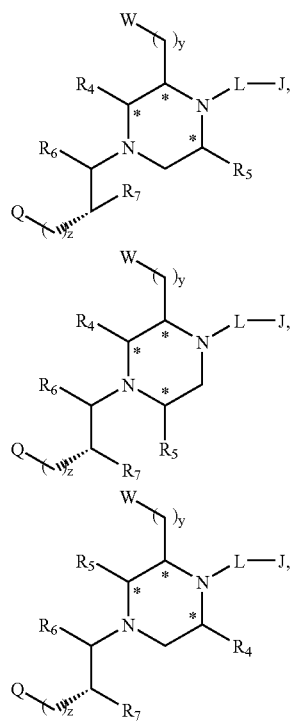

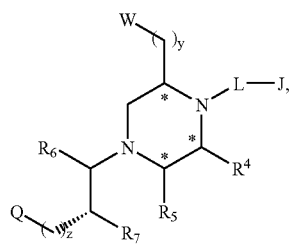

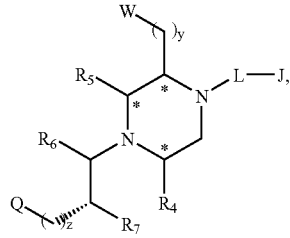

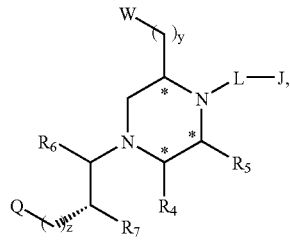

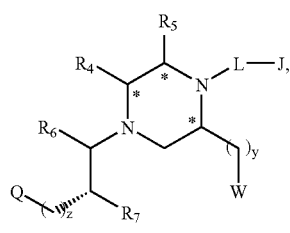

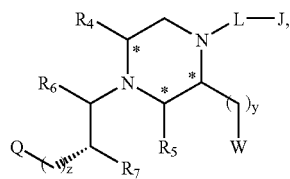

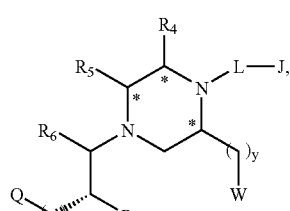

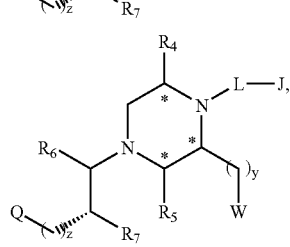

-continued

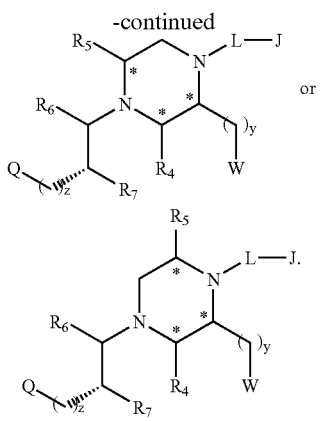

or

In one preferred embodiment, $R_4$ and $R_5$ are each independently $CH_3$,

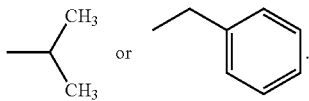

The present invention further provides a compound that is an agonist of a melanocortin receptor, including MC1-R, MC3-R, MC4-R, or MC5-R. The compound can also be an antagonist of a melanocortin receptor, including MC1-R, MC3-R, MC4-R, or MC5-R. The compound can also be an inverse agonist of a melanocortin receptor, including MC1-R, MC3-R, MC4-R, or MC5-R. The compound can also further be an antagonist of an inverse agonist of a melanocortin receptor, including MC1-R, MC3-R, MC4-R, or MC5-R.

The invention further includes a method for altering a disorder or condition associated with the activity of a melanocortin receptor, comprising administering to a patient a therapeutically effective amount a compound of this invention. In one embodiment the disorder or condition is an eating disorder such as cachexia. In another embodiment the disorder or condition is obesity and associated impairment of energy homeostasis. In yet another embodiment the disorder or condition is sexual dysfunction such as erectile dysfunction or female sexual dysfunction.

A primary object of the present invention is to provide a conformationally constrained and optically pure isomer of a tri-, tetra-, or penta-substituted piperazine, wherein the pendant group substituents are amino acid moieties, amino acid side chain moieties or derivatives thereof, such that the resulting ring compound mimics biologically a relevant reverse turn peptide structure.

Another object of the present invention is to provide methods for the synthesis of optically pure tri-, tetra-, or penta-substituted piperazine compounds.

Another object of the present invention is to provide piperazine compounds with three or four or five pendant groups, such pendant groups consisting of any moiety other than H, O, S, or a halogen.

Another object of the present invention is to provide piperazine core compounds wherein pendant groups are provided, which pendant groups are or include amino acid side chain moieties.

Another object of the present invention is to provide a tri-, tetra-, or penta-substituted piperazine compound wherein such compound is specific for one or more melanocortin receptors.

Another object of the present invention is to provide a method for synthesis of tri-, tetra-, or penta-substituted piperazine compounds of the invention.

Other objects, advantages and novel features, and the further scope of applicability of the present invention will be set forth in part in the detailed description to follow, and in part will become apparent to those skilled in the art upon examination of the following, or may be learned by practice of the invention.

DETAILED DESCRIPTION OF THE INVENTION

In this invention it is disclosed that piperazine rings may be employed with three, four or five descriptors, wherein each descriptor is a separate pendant group unique to a given ring atom. By employing three or four descriptors, the inventors have further found that the chirality of the ring, and stereo structure generally, is fixed in a desired structure, thereby more closely mimicking the desired pharmacophores, and with the descriptors positioned in the most relevant chemical space.

This invention thus discloses the use of tri-, tetra-, or penta-substituted piperazine templates for drug design. The invention further also relates to enantiomerically pure tri-, tetra- or penta-substituted piperazines, preferably made by the synthetic schemes disclosed herein or variants thereof. A classical piperazine ring is a conformationally dynamic six-membered ring structure. It can exist in a variety of conformational states, commonly referred to as chair, boat, twisted chair or twisted boat conformations. Because of this dynamism in structural states, the location of descriptors on the ring plays an important role in stabilizing the ring in a single conformational state; if the appropriate conformational state is selected, this is conducive to making a molecule more selective for its receptor. For example, a 1,3 axial placement of two bulky descriptors generally causes unfavorable steric interactions between these two groups, and thus make a chair conformation energetically less stable. Consequently, the chair conformation is less preferred, resulting in a twisted chair or boat conformation. The twisted chair or boat conformation results in a specific stereochemical alignment of the descriptors, which is specifically relevant to interaction with the desired receptor. Thus a conformation resulting from 1,3 axial placement of two descriptors may result in a structure more selective for a given receptor sub-type.

In yet another embodiment, the invention describes tri- and tetra-substituted piperazine compounds specific for G-protein coupled receptor systems, such systems including, but not limited to, melanotropin or melanocortin receptors (MC1-R, MC3-R, MC4-R and MC5-R).

In yet another embodiment, the invention provides novel schemes and methods of synthesis of tri-, tetra- or penta-substituted piperazine compounds.

Definitions. Before proceeding further with the description of the invention, certain terms are defined as set forth herein.

The "amino acid" and "amino acids" used in this invention, and the terms as used in the specification and claims, include the known naturally occurring protein amino acids, which are referred to by both their common three letter abbreviation and single letter abbreviation. See generally *Synthetic Peptides: A User's Guide*, G A Grant, editor, W.H. Freeman & Co., New York, 1992, the teachings of which are incorporated herein by reference, including the text and table set forth at pages 11 through 24. As set forth above, the term "amino acid" also includes stereoisomers and modifications of naturally occurring protein amino acids, non-protein amino acids, post-translationally modified amino acids, enzymatically synthesized amino acids, derivatized amino acids, constructs or structures designed to mimic amino acids, and the like. Modified and unusual amino acids are described generally in *Synthetic Peptides: A User's Guide*, cited above; Hruby V J, Al-obeidi F and Kazmierski W: *Biochem J* 268:249-262, 1990; and Toniolo C: *Int J Peptide Protein Res* 35:287-300, 1990; the teachings of all of which are incorporated herein by reference.

The term "amino acid side chain moiety" used in this invention includes any side chain of any amino acid, as the term "amino acid" is defined herein, including any derivative of an amino acid side chain moiety, as the term "derivative" is defined herein. This thus includes the side chain moiety present in naturally occurring amino acids. It further includes side chain moieties in modified naturally occurring amino acids, such as glycosylated amino acids. It further includes side chain moieties in stereoisomers and modifications of naturally occurring protein amino acids, non-protein amino acids, post-translationally modified amino acids, enzymatically synthesized amino acids, derivatized amino acids, constructs or structures designed to mimic amino acids, and the like. For example, the side chain moiety of any amino acid disclosed herein is included within the definition of an amino acid side chain moiety.

The "derivative" of an amino acid side chain moiety includes any modification to or variation in any amino acid side chain moieties, including a modification of naturally occurring amino acid side chain moieties. By way of example, derivatives of amino acid side chain moieties include straight chain or branched, cyclic or noncyclic, substituted or unsubstituted, and saturated or unsaturated alkyl, aryl or aralkyl moieties.

The following abbreviations for amino acids, amino acid side chain moieties and derivatives thereof have the meanings giving, it being understood that any amino acid may be in either the L- or D-configuration:

| Abbreviation | Meaning |
|---|---|
| Abu | gamma-amino butyric acid |
| 2-Abz | 2-amino benzoic acid |
| 3-Abz | 3-amino benzoic acid |
| 4-Abz | 4-amino benzoic acid |
| Achc | 1-amino-cyclohexane-1-carboxylic acid |
| Acpc | 1-amino-cyclopropane-1-carboxylic acid |
| 12-Ado | 12-amino dodecanoic acid |
| Aib | alpha-aminoisobutyric acid |
| Aic | 2-aminoindane-2-carboxylic acid |
| 6-Ahx | 6-amino hexanoic acid |
| Amb | 4-(aminomethyl)-benzoic acid |
| Amc | 4-(aminomethyl)-cyclohexane carboxylic acid |
| 7'-amino-heptanoyl | $NH_2$—$(CH_2)_6CO$— |
| 8-Aoc | 8-amino octanoic acid |
| Arg(Tos) | $N^G$-para-tosyl-arginine |
| Asp(anilino) | beta-anilino-aspartic acid |
| Asp(3-Cl-anilino) | beta-(3-chloro-anilino)-aspartic acid |
| Asp(3,5-diCl-anilino) | beta-(3,5-dichloro anilino)-aspartic acid |
| Atc | 2-aminotetralin-2-carboxylic acid |
| 11-Aun | 11-amino undecanoic acid |
| AVA | 5-amino valeric acid |
| Beta-hHyp(Bzl) | Beta-(O-benzyl)-homohydroxyproline |
| Beta-hSer(Bzl) | Beta-(O-benzyl)-homoserine |
| Bip | biphenylalanine |
| Bpa | 4-benzoylphenylalanine |
| Bzl | benzyl |
| Bz | benzoyl |
| Cha | cyclohexalanine |
| Chg | cyclohexylglycine |
| Cmpi | 4-caboxymethyl-piperazine |
| Cys(Bzl) | S-benzyl-cysteine |
| Dip | 3,3-diphenylalanine |
| Disc | 1,3-dihydro-2H-isoindolecarboxylic acid |
| Dpr(beta-Ala) | $N^{beta}$-(3-aminopropionyl)-alpha,beta-diaminopropionic acid |
| Et- | ethyl |
| GAA | epsilon-guanidino acetic acid |
| GBzA | 4-guanidino benzoic acid |
| B-Gpa | 3-guanidino propionic acid |
| GVA(Cl) | beta-chloro-epsilon-guanidino valeric acid |
| Heptanoyl | $CH_3$—$(CH_2)_5CO$— |
| HPhe | homophenylalanine |
| HSer | homoserine |
| HHyp | homo hydroxy proline |
| Hyp | hydroxy proline |
| Hyp(Bzl) | O-benzyl-hydroxyproline |
| Hyp(2-naphthly) | O-2' naphthyl-hydroxyproline |
| Hyp(Phenyl) | phenyl-hydroxyproline |
| Idc | indoline-2-carboxylic acid |
| Igl | indanylglycine |
| Inp | isonipecotic acid |
| Lys(Bz) | $N^e$-benzoyl-lysine |
| Lys(Z-2'Br) | $N^e$-(2-bromobenzyloxycarbonyl)-lysine |
| Lys(Z) | N-epsilon-benzyloxycarbonyl-lysine |
| Me | methyl |
| Nal 1 | 3-(1-naphthyl)alanine |
| Nal 2 | 3-(2-naphthyl)alanine |
| (N-Bzl)Nal 2 | N-benzyl-3-(2-naphthyl) alanine |
| 2-Naphthylacetyl | 2-naphthyl-$CH_2CO$— |
| (Nlys)Gly | N-(4-aminobutyl)-glycine |
| (N-PhEt)Nal 2 | N(2-phenylethyl)-3-(2-naphthyl) alanine |
| OcHx | cyclohexyl ester |
| pF-Phe | para-fluoro-phenylalanine |
| Phe(4-Br) | 4-bromo-phenylalanine |
| Phe(4-$CF_3$) | 4-trifluoromethyl-phenylalanine |
| Phe(4-Cl) | 4-chloro-phenylalanine |
| Phe(3-Cl) | 3-chloro-phenylalanine |
| Phe(2-Cl) | 2-chloro-phenylalanine |
| Phe(2,4-diCl) | 2,4,-dichloro-phenylalanine |
| Phe(3,4-diCl) | 3,4,-dichloro-phenylalanine |
| Phe(5-Cl) | 5-chloro-phenylalanine |
| Phe(2-Cl, 4-$CF_3$) | 2-chloro-4-trifluoromethyl-phenylalanine |
| Phe(2-Cl, 4-Me) | 2-chloro-4-methyl-phenylalanine |
| Phe(3,4-diF) | 3,4,-difluoro-phenylalanine |
| Phe(2-F, 4-Cl) | 4-chloro-4-fluoro-phenylalanine |
| Phe(2,4-diF) | 2,4-difluoro-phenylalanine |
| Phe(4-I) | 4-iodo-phenylalanine |
| Phe(4-Me) | 4-methyl-phenylalanine |
| Phe(2,4-diMe) | 2,4-dimethyl-phenylalanine |
| Phe(4-OMe) | 4-methoxy-phenylalanine |
| Phe(3,4-di-OMe) | 3,4,-dimethoxy-phenylalanine |
| Phe(2-Me, 4-Cl) | 4-chloro-2-methyl-phenylalanine |
| Phe(4-NC) | 4-cyano-phenylalanine |
| Phe(4-$NO_2$) | 4-nitro-phenylalanine |
| Phe(4-Phenyl) | 4-phenyl-phenylalanine |
| Phg | phenylglycine |
| Pip | pipecolic acid |
| Pr | propyl |
| Pr-I | isopropyl |
| 3-Pya | 3-pyridylalanine |
| Pyr | pyroglutamic acid |
| Qal(2') | beta-(2-quinolyl)-alanine |
| Sal | 3-styrylalanine |
| Sar | sarcosine |
| Ser(Bzl) | O-benzyl-serine |
| Ser(2-Naphthyl) | O-2-Naphthyl-serine |
| Ser(Phenyl) | O-2-Phenyl-serine |
| Ser(4-Cl-Phenyl) | O-4-Cl-Phenyl-serine |
| Ser(2-Cl-Phenyl) | O-2-Cl-Phenyl-serine |
| Ser(p-Cl-Bzl) | O-4-Cl-Benzyl-serine |
| Thr(Bzl) | O-Benzyl-threonine |
| Tic | 1,2,3,4-tetrahydroisoquinoline-3-carboxylic acid |
| Tiq | 1,2,3,4-tetrahydroisoquinoline-1-carboxylic acid |
| Tle | tert-butylalanine |
| Tpi | 1,2,3,4-tetrahydronorharman-3-carboxylic acid |
| Tyr(Bzl) | O-benzyl-tyrosine |
| Tyr(2,6-DiCl-Bzl) | O-(2,6 dichloro)benzyl-tyrosine |
| Z | benzyloxycarbonyl |

In the listing of compounds according to the present invention, conventional amino acid residues have their conventional meaning as given in Chapter 2400 of the *Manual of Patent Examining Procedure*, 8th Ed. Thus, "Nle" is norleucine; "Asp" is aspartic acid; "His" is histidine; "D-Phe" is D-phenylalanine; "Arg" is arginine; "Trp" is tryptophan; "Lys" is lysine; "Gly" is glycine; "Pro" is proline; "Tyr" is tyrosine, "Ser" is serine and so on. The following amino acids, or side chains thereof, may be employed, in either the L- or D-configuration as appropriate, in certain embodiments of this invention:

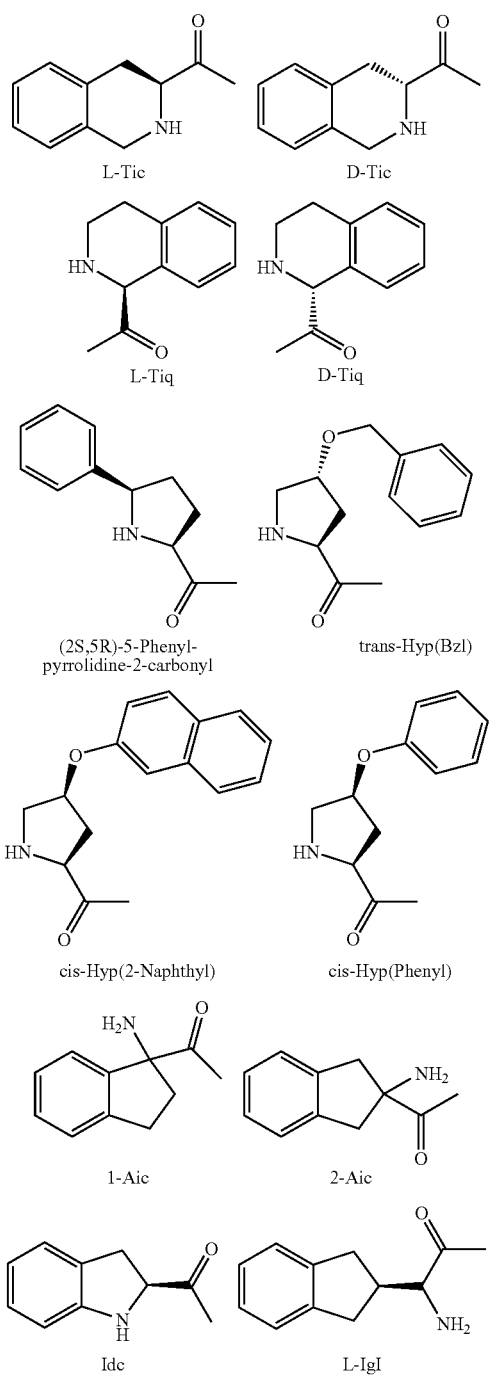

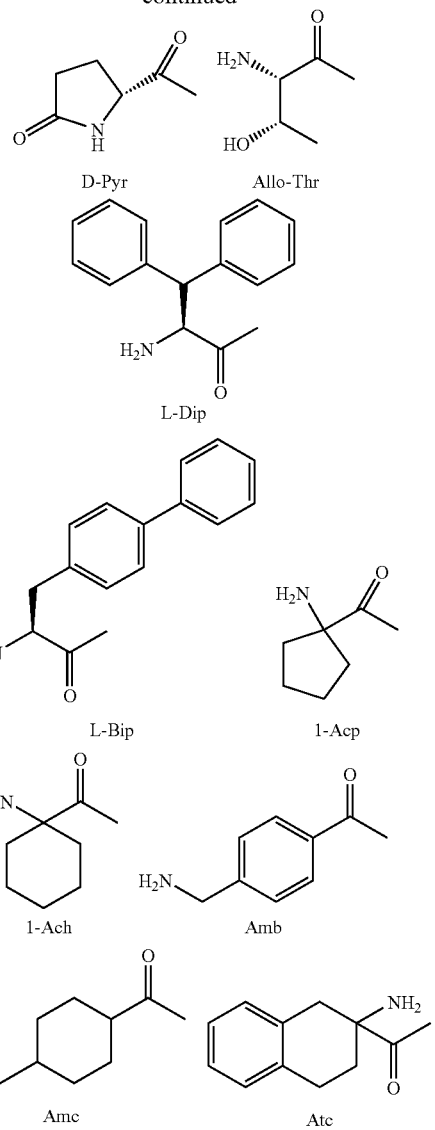

In the specification and the claims, the term "homolog" includes, without limitation, (a) a D-amino acid residue or side chain substituted for an L-amino acid residue side chain, (b) a post-translationally modified residue or side chain substituted for the residue or side chain, (c) a non-protein or other modified amino acid residue or side chain based on another such residue or side chain, such as phenylglycine, homophenylalanine, ring-substituted halogenated, and alkylated or arylated phenylalanines for a phenylalanine residue, diamino proionic acid, diamino butyric acid, ornithine, lysine and homoarginine for an arginine residue, and the like, and (d) any amino acid residue or side chain, coded or otherwise, or a construct or structure that mimics an amino acid residue or side chain, and which has at least a similarly charged side chain (neutral, positive or negative), preferably a similar hydrophobicity or hydrophilicity, and preferably a similar side chain in terms of being a saturated aliphatic side chain, a functionalized aliphatic side chain, an aromatic side chain or a heteroaromatic side chain.

The term "alkene" includes unsaturated hydrocarbons that contain one or more double carbon-carbon bonds. Examples of such alkene groups include ethylene, propene, and the like.

The term "alkenyl" includes a linear monovalent hydrocarbon radical of two to six carbon atoms or a branched monovalent hydrocarbon radical of three to six carbon atoms containing at least one double bond; examples thereof include ethenyl, 2-propenyl, and the like.

The "alkyl" groups specified herein include those alkyl radicals of the designated length in either a straight or branched configuration. Examples of such alkyl radicals include methyl, ethyl, propyl, isopropyl, butyl, sec-butyl, tertiary butyl, pentyl, isopentyl, hexyl, isohexyl, and the like.

The term "alkynal" includes a linear monovalent hydrocarbon radical of two to six carbon atoms or a branched monovalent hydrocarbon radical of three to six carbon atoms containing at least one triple bond; examples thereof include ethynyl, propynal, butynyl, and the like.

The term "aryl" includes a monocyclic or bicyclic aromatic hydrocarbon radical of 6 to 12 ring atoms, and optionally substituted independently with one or more substituents selected from alkyl, haloalkyl, cycloalkyl, alkoxy, alkythio, halo, nitro, acyl, cyano, amino, monosubstituted amino, disubstituted amino, hydroxy, carboxy, or alkoxy-carbonyl. Examples of an aryl group include phenyl, biphenyl, naphthyl, 1-naphthyl, and 2-naphthyl, derivatives thereof, and the like.

The term "aralkyl" includes a radical—$R^a R^b$ where $R^a$ is an alkylene (a bivalent alkyl) group and $R^b$ is an aryl group as defined above. Examples of aralkyl groups include benzyl, phenylethyl, 3-(3-chlorophenyl)-2-methylpentyl, and the like.

The term "aliphatic" includes compounds with hydrocarbon chains, such as for example alkanes, alkenes, alkynes, and derivatives thereof.

The term "acyl" includes a group RCO—, where R is an organic group. An example is the acetyl group $CH_3CO$—.

A group or aliphatic moiety is "acylated" when an alkyl or substituted alkyl group as defined above is bonded through one or more carbonyl [—(C=O)—] groups.

An "omega amino derivative" includes an aliphatic moiety with a terminal amino group. Examples of omega amino derivatives include aminoheptanoyl and the amino acid side chain moieties of ornithine and lysine.

The term "heteroaryl" includes mono- and bicyclic aromatic rings containing from 1 to 4 heteroatoms selected from nitrogen, oxygen and sulfur. 5- or 6-membered heteroaryl are monocyclic heteroaromatic rings; examples thereof include thiazole, oxazole, thiophene, furan, pyrrole, imidazole, isoxazole, pyrazole, triazole, thiadiazole, tetrazole, oxadiazole, pyridine, pyridazine, pyrimidine, pyrazine, and the like. Bicyclic heteroaromatic rings include, but are not limited to, benzothiadiazole, indole, benzothiophene, benzofuran, benzimidazole, benzisoxazole, benzothiazole, quinoline, benzotriazole, benzoxazole, isoquinoline, purine, furopyridine and thienopyridine.

An "amide" includes compounds that have a trivalent nitrogen attached to a carbonyl group (—$CO.NH_2$), such as methylamide, ethylamide, propylamide, and the like.

An "imide" includes compounds containing an imido group (—CO.NH.CO—).

An "amine" includes compounds that contain an amino group (—$NH_2$)—.

A "nitrile" includes compounds that are carboxylic acid derivatives and contain a (—CN) group bound to an organic group.

An amino acid side chain moiety is "hydrogen bonding" when the side chain includes hydrogen donors or alternatively hydrogen acceptors.

An "amine capping group" includes any terminal group attached through a terminal amine, including but not limited to any omega amino derivative, acyl group or terminal aryl or aralkyl, including groups such as a $C_1$ to $C_6$ linear or branched chain such as methyl, dimethyl, ethyl, propyl, isopropyl, butyl, isobutyl, pentyl, or hexyl, groups such as allyl, cyclopropane methyl, hexanoyl, heptanoyl, acetyl, propionoyl, butanoyl, phenylacetyl, cyclohexylacetyl, naphthylacetyl, cinnamoyl, phenyl, benzyl, benzoyl, 12-Ado, 7'-amino heptanoyl, 6-Ahx, Amc or 8-Aoc, or a molecule such as polyethylene glycol with a formula molecular weight of between 100 and 10,000.

The term "composition", as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and one or more pharmaceutically acceptable carriers, and optionally one or more pharmaceutically active ingredients and agents.

A variety of chemicals and compounds are employed in this invention, and the following abbreviations have the meanings given:

| | |
|---|---|
| AcOH | acetic acid |
| Boc | tertiary butyloxycarbonyl |
| Cbz | benzyloxycarbonyl |
| DCM | dichloromethane |
| DEAD | diethyl azodicarboxylate |
| DIAD | diisopropyl azodicarboxylate |
| DIC | 1,3-diisopropylcarbodiimide |
| DMF | N,N-dimethylformamide |
| DMSO | dimethyl sulfoxide |
| EDC | N-(3-dimethylaminopropyl)-N'-ethylcarbodiimide hydrochloride |
| EtOAc | ethyl acetate |
| Fmoc | 9-fluorenylmethoxycarbonyl |
| HEPES | 4-(2-hydroxyethyl)1-piperazineethanesulfonic acid |
| HOAt | 1-hydroxy-7-azabenzotriazole |
| IBCF | isobutyl chloroformate |
| LAH | lithium aluminum hydride |
| NMM | N-methylmorpholine |
| NMP | 1-methyl-2-pyrrolidinone |
| TBTU | 2-(1H-Benzotriazole-1-yl)-1,1,3,3-tetramethyluronium tetrafluoroborate |
| TEA | triethylamine |
| TFA | trifluoroacetic acid |
| THF | tetrahydrofuran |
| TPP | triphenylphosphine |

A "tri-substituted piperazine", as used herein, is a piperazine compound or derivative thereof wherein a group other than solely H, and preferably including an amino acid residue or an amino acid side chain moiety, are attached to each ring N member, and further wherein a group other than solely H, O, S or a halogen, preferably including an amino acid side chain moiety, are attached to one ring C member.

A "tetra-substituted piperazine", as used herein, is a piperazine compound or derivative thereof wherein a group other than solely H, and preferably including an amino acid residue or an amino acid side chain moiety, are attached to each ring N member, and further wherein groups other than solely H, O, S or a halogen, preferably including an amino acid side chain moiety, are attached to two ring C members.

A "penta-substituted piperazine", as used herein, is a piperazine compound or derivative thereof wherein groups a group other than solely H, and preferably including an amino acid residue or an amino acid side chain moiety, are attached to both ring N members, and further wherein groups other than solely H, O, S or a halogen, preferably including an amino acid side chain moiety, are attached to three ring C members.

"Sexual dysfunction" means any condition that inhibits or impairs normal sexual function, including coitus. The term is not limited to physiological conditions, and includes psychogenic conditions or perceived impairment without a formal diagnosis of pathology or disorder. Sexual dysfunction includes erectile dysfunction in a male mammal and female sexual dysfunction in a female mammal.

"Erectile dysfunction" is a disorder involving the failure of a male mammal to achieve functional erection, ejaculation, or both. Erectile dysfunction is accordingly synonymous with impotence, and includes the inability to attain or sustain an erection of sufficient rigidity for coitus. Symptoms of erectile dysfunction include an inability to achieve or maintain an erection, ejaculatory failure, premature ejaculation, or inability to achieve an orgasm. An increase in erectile dysfunction is often associated with age or may be caused by a physical disease or as a side-effect of drug treatment.

"Female sexual dysfunction" is a disorder including sexual arousal disorder. The term "sexual arousal disorder" includes a persistent or recurrent failure to attain or maintain the lubrication-swelling response of sexual excitement until completion of sexual activity. Sexual dysfunction in females can also include inhibited orgasm and dyspareunia, which is painful or difficult coitus. Female sexual dysfunction includes, but is not limited to, a number of categories of diseases, conditions and disorders including hypoactive sexual desire disorder, sexual anhedonia, sexual arousal disorder, dyspareunia and vaginismus. Hypoactive sexual desire disorder includes a disorder in which sexual fantasies and desire for sexual activity are persistently or recurrently diminished or absent, causing marked distress or interpersonal difficulties. Hypoactive sexual desire disorder can be caused by boredom or unhappiness in a long-standing relationship, depression, dependence on alcohol or psychoactive drugs, side effects from prescription drugs, or hormonal deficiencies. Sexual anhedonia includes decreased or absent pleasure in sexual activity. Sexual anhedonia can be caused by depression, drugs, or interpersonal factors. Sexual arousal disorder can be caused by reduced estrogen, illness, or treatment with diuretics, antihistamines, antidepressants, or antihypertensive agents. Dyspareunia and vaginismus are sexual pain disorders characterized by pain resulting from penetration and may be caused, for example, by medications which reduce lubrication, endometriosis, pelvic inflammatory disease, inflammatory bowel disease or urinary tract problems.

By a melanocortin receptor "agonist" is meant an endogenous or drug substance or compound, including a compound of this invention, which can interact with a melanocortin receptor and initiate a pharmacological response characteristic of the melanocortin receptor. By a melanocortin receptor "antagonist" is meant a drug or a compound, including a compound of this invention, which opposes the melanocortin receptor-associated responses normally induced by a melanocortin receptor agonist agent.

By "binding affinity" is meant the ability of a compound or drug to bind to its biological target.

Clinical Applications. The compounds disclosed herein can be used for both medical applications and animal husbandry or veterinary applications. Typically, the product is used in humans, but may also be used in other mammals. The term "patient" is intended to denote a mammalian individual, and is so used throughout the specification and in the claims. The primary applications of this invention involve human patients, but this invention may be applied to laboratory, farm, zoo, wildlife, pet, sport or other animals.

Melanocortin receptor-specific compounds of this invention that are MC1-R specific can be used as chemoprevention agents against sun-induced, such as by UV radiation, neoplastic activity in human skin. MC1-R agonist compounds of this invention may be employed to stimulate epidermal melanocytes to produce melanin as well as to convert pheomelanin to eumelanin. Eumelanin, which is dark brown or black pigmentation, is considered more photo-protective than pheomelanin, which is yellow or red pigmentation. The process of melanogenesis is believed to involve stimulation of MC1-R in epidermal melanocytes, thereby mediating the stimulation of tyrosinase enzymes within these pigment cells, inducing the conversion of tyrosine to dopa and then through dopaquinone to eumelanin. Sun tanning due to direct sun exposure is proposed to result from the same pathway by local production of melanotropic peptide from a POMC gene in the epidermis. Thus stimulation of eumelanin production and conversion of pheomelanin to eumelanin may be a desirable chemoprevention modality in blocking sun- or UV-induced neoplastic activity in skin. A potent, high-affinity and highly selective MC1-R agonist compound of this invention can accordingly be used as a therapeutic chemoprevention agent for combating harmful sun or UV exposure that induces neoplastic activity in skin melanocytes.

In another embodiment, compounds of this invention that are MC4-R agonists can be used as a therapeutic agent to modify energy metabolism and feeding behavior, including treatment of pathologic obesity and related conditions. Compounds of this invention that are MC4-R antagonists can also be used as a therapeutic agent in eating disorders, such as treatment of anorexia and cachexia, which is malnutrition and wasting due to illness. Control centers for eating and satiety reside in the hypothalamus. These responses are determined by diverse hormones and soluble factors that signal through specific receptors in the hypothalamus. MC4-R is known to be expressed in the brain, and inactivation of this receptor by gene targeting has resulted in mice with a maturity-onset obesity syndrome associated with hyperphagia, hyperinsulinemia and hyperglycemia.

In yet another embodiment, compounds of this invention can be used as therapeutic agents for treatment of sexual dysfunction, including treatment of both male erectile dysfunction and female sexual dysfunction.

In yet another embodiment, compounds of this invention may be used as therapeutic agents for treatment of inflammation, including specifically MC1-R, MC3-R and MC5-R agonists.

In yet another embodiment of the invention, compounds of this invention that are MC5-R specific can be used as agents to decrease sebum production, and thus may be efficacious in the treatment of acne and related diseases. The compounds for this application may be conveniently formulated for local administration, as through a gel, lotion, cream or other topical formulation.

The compounds may be formulated by any means known in the art, including but not limited to tablets, capsules, caplets, suspensions, powders, lyophilized forms and aerosols and may be mixed and formulated with buffers, binders, stabilizers, anti-oxidants and other agents known in the art. The compounds may be administered by any systemic or partially systemic means known in the art, including but not limited to intravenous injection, subcutaneous injection, administration through mucous membranes, oral administration, dermal administration, skin patches, aerosols and the like.

The invention further provides a pharmaceutical composition that includes a compound of this invention and a pharmaceutically acceptable carrier. The compound of this invention may thus be formulated or compounded into pharmaceutical compositions that include at least one compound of this invention together with one or more pharmaceutically acceptable carriers, including excipients, such as diluents, carriers and the like, and additives, such as stabilizing agents, preservatives, solubilizing agents, buffers and the like, as may be desired. Formulation excipients may include polyvinylpyrrolidone, gelatin, hydroxy cellulose, acacia, polyethylene glycol, mannitol, sodium chloride or sodium citrate. For injection or other liquid administration formulations, water containing at least one or more buffering constituents is suitable, and stabilizing agents, preservatives and solubilizing agents may also be employed. For solid administration formulations, any of a variety of thickening, filler, bulking and carrier additives may be employed, such as starches, sugars, fatty acids and the like. For topical administration formulations, any of a variety of creams, ointments, gels, lotions and the like may be employed. For most pharmaceutical formulations, non-active ingredients will constitute the greater part, by weight or volume, of the preparation. For pharmaceutical formulations, it is also contemplated that any of a variety of measured-release, slow-release or time-release formulations and additives may be employed, such that the dosage may be formulated so as to effect delivery of a compound of this invention over a period of time.

The compounds of this invention may be in the form of any pharmaceutically acceptable salt. Acid addition salts of the compounds of this invention are prepared in a suitable solvent from the compound and an excess of an acid, such as hydrochloric, hydrobromic, sulfuric, phosphoric, acetic, trifluoroacetic, maleic, succinic or methanesulfonic. The acetate salt form is especially useful. Where the compounds of this invention include an acidic moiety, suitable pharmaceutically acceptable salts may include alkali metal salts, such as sodium or potassium salts, or alkaline earth metal salts, such as calcium or magnesium salts.

The compounds and pharmaceutical compositions of this invention may be administered by injection, which injection may be intravenous, subcutaneous, intramuscular, intraperitoneal or by any other means known in the art. In general, any route of administration by which the compounds of this invention are introduced across an epidermal layer of cells may be employed. Administration means may include administration through mucous membranes, buccal administration, oral administration, dermal administration, inhalation administration, nasal administration and the like. The dosage for treatment is administration, by any of the foregoing means or any other means known in the art, of an amount sufficient to bring about the desired therapeutic effect.

Therapeutically Effective Amount. In general, the actual quantity of compound of this invention administered to a patient will vary between fairly wide ranges depending upon the mode of administration, the formulation used, and the response desired. The dosage for treatment is administration, by any of the foregoing means or any other means known in the art, of an amount sufficient to bring about the desired therapeutic effect. This may readily be determined by one of ordinary skill in the art through means such as pharmacokinetic studies, plasma half-life studies, dose escalation studies, and the like. Thus a therapeutically effective amount includes an amount of a compound or pharmaceutical composition of this invention that is sufficient to induce the desired therapeutic effect.

In general, the compounds of this invention are highly active, with dose responses as low as 0.01 µg/kg, generally with optimal or peak dose responses between about 0.01 µg/kg and 25 µg/kg, depending on the specific compound and the route of administration. For example, the compound can be administered at 0.01, 0.05, 0.1, 0.5, 1, 5, 10, 50, 100, or 500 µg/kg body weight, depending on specific compound selected, the desired therapeutic response, the route of administration, the formulation and other factors known to those of skill in the art. Conventional dose response studies and other pharmacological means may be employed to determine the optimal dose for a desired effect with a given compound, given formulation and given route of administration.

Combination Therapy and Sexual Dysfunction. It is also possible and contemplated to use the compounds of this invention in combination with other drugs or agents for treatment of sexual dysfunction. These other drugs and agents may include melanocortin receptor-specific agents that induce erectile activity, including specifically MC3-R and MC4-R agonists, phosphodiesterase-5 inhibitors, testosterone, prostaglandin and the like. In a preferred embodiment of the invention, compounds of the invention are used in combination with a therapeutically effective amount of a cyclic-GMP-specific phosphodiesterase inhibitor or an alpha-adrenergic receptor antagonist. Similarly, the compounds of this invention may be used in combination with any known mechanical aids or devices.

The present invention thus provides methods of treating sexual dysfunction, the methods comprising the step of administering to the patient having or at risk of having sexual dysfunction a therapeutically effective amount of a compound of this invention in combination with a therapeutically effective amount of a second sexual dysfunction pharmaceutical agent. The compound of this invention may be administered simultaneously with, prior to or subsequent to administration with a therapeutically effective amount of a second sexual dysfunction pharmaceutical agent. Preferably the compound of this invention is administered within one hour, preferably within less than one-half hour, of administration of a therapeutically effective amount of a second sexual dysfunction pharmaceutical agent. However, for certain forms of combination therapy, such as for example in combination with a therapeutically effective amount of a hormone or hormone-related sexual dysfunction pharmaceutical agent, the hormone or hormone-related sexual dysfunction pharmaceutical agent may be administered on an independent schedule, such that there is no set or specific temporal relationship between administration of the compound of this invention and the hormone or hormone-related sexual dysfunction pharmaceutical agent. Thus, for example, the hormone or hormone-related sexual dysfunction pharmaceutical agent may be administered on a daily or other dose, or by means of patches or other continuous administration schedules, with administration of the compound of this invention when desired or needed by the patient.

The present invention thus provides methods of treating sexual dysfunction, the methods comprising the step of administering to a patient having or at risk of having sexual dysfunction a therapeutically effective amount of a compound of this invention in combination with a compound that is a melanocortin receptor agonist.

The present invention further also provides methods of treating sexual dysfunction, the methods comprising the step of administering to a patient having or at risk of having sexual dysfunction a therapeutically effective amount of a compound of this invention in combination with a compound that is a melanocortin receptor agonist and in combination with another compound that is useful in the treatment of sexual dysfunction.

In a preferred embodiment of combination therapy the sexual dysfunction is female sexual dysfunction. In an especially preferred embodiment of combination therapy the sexual dysfunction is erectile dysfunction. In a preferred embodiment of the foregoing methods, the melanocortin receptor agonist is an agonist of MC3-R or MC4-R, and preferably MC4-R. The agonist may be a non-selective MC3-R and MC4-R agonist.

The present invention also provides pharmaceutical compositions that comprise 1) a compound of this invention and 2) a compound that is a melanocortin receptor agonist. The present invention further provides pharmaceutical compositions that comprise 1) a compound of this invention; 2) a compound that is a melanocortin receptor agonist; and 3) a third compound useful for the treatment of sexual dysfunction. The present invention further provides pharmaceutical compositions that comprise 1) a compound of this invention and 2) a second compound useful for the treatment of sexual dysfunction.

Representative agonists of the melanocortin receptor which are a second compound useful in combination therapy are disclosed in the following publications, which are incorporated here by reference in their entirety: M. E. Hadley et al., Discovery and development of the novel melanogenic drugs, in *Integration of Pharmaceutical Discovery and Development: Case Studies*, edited by Borchardt et al., Plenum Press, New York (1998); R. T. Dorr et al., Evaluation of Melanotan-II, A Superpotent Cyclic Melanotropic Peptide in a Pilot Phase-I Clinical Study. *Life Sci.* 58:1777-1784 (1996); and R. A. H. Adan, Identification of Antagonists for Melanocortin MC3, MC4, and MC5 Receptors. *Eur. J. Pharmacol.*, 269: 331-337 (1994).

In one embodiment of the composition above, the agonists are melanocyte-stimulating hormones (MSH) including α-, β-, and γ-MSH and/or adrenocorticotropic hormones (ACTH).

In another embodiment of the composition above, the melanocortin receptor agonist is Melanotan-II (MT-II). A preferred melanocortin receptor agonist includes any linear or cyclic melanocortin receptor-specific agonist peptide disclosed in International Application WO 03/006620 or a metallopeptide disclosed in International Application WO 02/064091. A particularly preferred melanocortin receptor agonist is Ac-Nle-cyclo(-Asp-His-D-Phe-Arg-Trp-Lys)-OH, as disclosed in U.S. Pat. No. 6,579,968. Alternatively, the agonist may be any agonist disclosed in any of the following patents or patent applications: U.S. Pat. Nos. 6,534,503, 6,472,398, 6,458,790, 6,410,548, 6,376,509, or 6,350,760; U.S. Published Application Nos. 2002/0137664, 2002/0004512, 2002/0143141, or US 2003/0069169; or International Application No. WO 02/18437. The agonist of the melanocortin receptor may preferably be selective for MC4-R.

In an embodiment of the composition above, the additional compounds useful for the treatment of sexual dysfunction are preferably selected from but not limited to the group consisting of a phosphodiesterase inhibitor; a cyclic-GMP-specific phosphodiesterase inhibitor; prostaglandins; apomorphin; oxytocin modulators; α-adrenergic antagonists; dopanergic ligands; androgens; selective androgen receptor modulators (SARMs); buprobion; vasoactive intestinal peptide (VIP); neutral endopeptidase inhibitors (NEP); neuropeptide Y receptor antagonists (NPY); and bombesin receptor-3 antagonists.

In an embodiment of the method and composition, the second sexual dysfunction pharmaceutical agent is testosterone.

In another embodiment of combination therapy, the second sexual dysfunction pharmaceutical agent is a type V phosphodiesterase inhibitor (PDE-5). For example, the PDE-5 inhibitor may be Viagra®, a brand of sildenafil, Levitra®, Cialis®), or may be 1-[[3-(6,7-dihydro-1-methyl-7-oxo-3-propyl-1-H-pyrazolo[4,3-d]pyrimidin-5-yl]-4-ethoxy-phenyl]sufonyl)-4-methylpiperazine citrate salt, as disclosed in U.S. Published Application No. 2003/0083228.

In another embodiment of the composition above, the compound useful for the treatment of sexual dysfunction is an estrogen agonist/antagonist. In one embodiment, the estrogen agonist/antagonist is (–)-cis-6-phenyl-5-[-4-(2-pyrrolidin-1-yl-ethoxy)-phenyl]-5,6,7,8-tetrahydro-napth-thalene-2-ol (also known as lasofoxifene) or an optical or geometric isomer thereof; a pharmaceutically acceptable salt, N-oxide, ester, quaternary ammonium salt; or a prodrug thereof. More preferably, the estrogen agonist/antagonist is in the form of a D-tartrate salt.

In yet another embodiment of the composition above, the estrogen agonist/antagonist is selected from the group consisting of tamoxifen, 4-hydroxy tamoxifen, raloxifene, droloxifene, toremifene, centchroman, idoxifene, 6-(4-hydroxy-phenyl)-5-[4-(2-piperidine-1-yl-ethoxy)-benzyl]-napthalen-2-ol, {4-[2-(2-aza-bicyclo[2.2.1]hept-2-yl)-ethoxy]-phenyl}-[6-hydroxy-2-(4-hydroxy-phenyl)-benzo[b]thiopehn-3-yl]-methanone, EM-652, EM-800, GW 5368, GW 7604, TSE-424 and optical or geometric isomers thereof; and pharmaceutically acceptable salts, N-oxides, esters, quaternary ammonium salts, and prodrugs thereof.

In yet another embodiment, a compound of this invention may be used in combination with any known mechanical aids or devices.

The present invention also provides kits for the treatment of sexual dysfunction (including erectile dysfunction), the kits comprising: a first pharmaceutical composition including a compound of this invention; a second pharmaceutical composition comprising a second compound useful for the treatment of sexual dysfunction; and, a container for the first and second compositions.

Female Sexual Dysfunction. The compounds of this invention may be used to treat female sexual dysfunction as well as male sexual dysfunction. In general, the dosing schedules and doses for females are comparable to those for males.

Combination Therapy and Weight Regulation. It is also possible and contemplated to use compounds of this invention in combination with other drugs or agents for treatment of various weight and feeding-related disorders. Where the compound is an agonist or partial agonist, the compound may be employed for decreasing food intake and/or body weight in combination with any other agent or drug heretofore employed as a diet aid, or for decreasing food intake and/or body weight. Where the compound is an antagonist, the compound may be employed for increasing food intake and/or body weight in combination with any other agent or drug heretofore employed for increasing food intake and/or body weight.

Drugs that reduce energy intake include, in part, various pharmacological agents, referred to as anorectic drugs, which are used as adjuncts to behavioral therapy in weight reduction programs. Classes of anorectic drugs include, but are not limited to, noradrenergic and serotonergic agents. Noradrenergic medications may be described as those medications generally preserving the anorectic effects of amphetamines but with weaker stimulant activity. The noradrenergic drugs, except phenylpropanolamine, generally act through a centrally mediated pathway in the hypothalamus that causes anorexia. Phenylpropanolamine, a racemic mixture of norephedrine esters, causes a release of norepinephrine throughout the body and stimulates hypothalamic adrenoreceptors to reduce appetite.

Suitable noradrenergic agents include, but are not limited to, diethylpropion such as TENUATE™ (1-propanone, 2-(diethylamino)-1-phenyl-, hydrochloride) commercially available from Merrell; mazindol (or 5-(p-chlorophenyl)-2,5-dihydro-3H-imidazo[2,1-a]isoindol-5-ol) such as SANOREX™ commercially available from Novartis or MAZANOR™ commercially available from Wyeth Ayerst; phenylpropanolamine (or Benzenemethanol, alpha-(1-aminoethyl)-, hydrochloride); phentermine (or Phenol, 3-[[4,5-duhydro-1H-imidazol-2-yl)ethyl](4-methylphenyl)amino], monohydrochloride) such as ADIPEX-P™ commercially available from Lemmon, FASTIN™ commercially available from Smith-Kline Beecham and Ionamin™ commercially available from Medeva; phendimetrazine (or (2S,3S)-3,4-Dimethyl-2phenylmorpholine L-(+)-tartrate (1:1)) such as METRA™ commercially available from Forest, PLEGINE™ commercially available from Wyeth-Ayerst; PRELU-2™ commercially available from Boehringer Ingelheim, and STATOBEX™ commercially available from Lemmon; phendamine tartrate such as THEPHORIN™ (2,3,4,9-Tetrahydro-2-methyl-9-phenyl-1H-indenol[2,1-c]pyridine L-(+)-tartrate (1:1)) commercially available from Hoffmann-LaRoche; methamphetamine such as DESOXYN™ Tablets ((S)—N, (alpha)-dimethylbenzeneethanamine hydrochloride) commercially available from Abbott; and phendimetrazine tartrate such as BONTRIL™ Slow-Release Capsules (-3,4-Dimethyl-2-phenylmorpholine Tartrate) commercially available from Amarin.

Suitable non-limiting serotonergic agents include sibutramine such as MERIDIA™ capsules (a racemic mixture of the (+) and (−) enantiomers of cyclobutanemethanamine, 1-(4-chlorophenyl)-N,N-dimethyl-(alpha)-(2-methylpropyl)-, hydrochloride, monohydrate) commercially available from Knoll, fenfluramine such as Pondimin™ (Benzeneethanamine, N-ethyl-alpha-methyl-3-(trifluoromethyl)-, hydrochloride) commercially available from Robbins; dexfenfluramine such as Redux™ (Benzeneethanamine, N-ethyl-alpha-methyl-3-(trifluoromethyl)-, hydrochloride) commercially available from Interneuron. Fenfluramine and dexfenfluramine stimulate release of serotonin and inhibit its reuptake. Sibutramine inhibits the reuptake of serotonin, norepinephrine and dopamine, but does not stimulate secretion of serotonin.

Other serotonergic agents useful with the practice of the present invention include, but are not limited to, certain auoretic gene 5HT1a inhibitors (brain, serotonin) such as carbidopa and benserazide as disclosed by U.S. Pat. No. 6,207,699 which is incorporated herein by reference; and certain neurokinin 1 receptor antagonist and selective serotonin reuptake inhibitors including fluoxetine, fluvoxamine, paroxtine, sertraline and other useful compounds as disclosed by U.S. Pat. No. 6,162,805 which is incorporated herein by reference. Other potential inhibitors that may be employed include 5HT2c inhibitors.

Other useful compounds for reducing energy intake include, but are not limited to, certain aryl-substituted cyclobutylalkylamines as disclosed by U.S. Pat. No. 6,127,424 which is incorporated herein by reference; certain trifluoromethylthiophenylethylamine derivatives as disclosed by U.S. Pat. No. 4,148,923 which is incorporated herein by reference; certain compounds as disclosed by U.S. Pat. No. 6,207,699 which is incorporated herein by reference; certain kainite or AMPA receptor antagonists as disclosed by U.S. Pat. No. 6,191,117 which is incorporated herein by reference; certain neuropeptide receptor subtype 5 as disclosed by U.S. Pat. No. 6,140,354 which is incorporated herein by reference; and certain alpha-blocking agents as disclosed by U.S. Pat. No. 4,239,763 which is incorporated herein by reference.

Moreover, several peptides and hormones regulate feeding behavior. For example, cholecystokinin and serotonin act to decrease appetite and food intake. Leptin, a hormone produced by fat cells, controls food intake and energy expenditure. In obese persons who are losing weight without medications, a decrease in weight is associated with a decrease in circulating levels of leptin, suggesting its role in weight homeostasis. Obese patients with high leptin levels are thought to have peripheral leptin resistance secondary to the down-regulation of leptin receptors. Non-limiting examples of useful compounds affecting feeding behavior include certain leptin-lipolysis stimulated receptors as disclosed by WO 01/21647 which is incorporated herein by reference; certain phosphodiesterase enzyme inhibitors as disclosed by WO 01/35970 which is incorporated herein by reference; certain compounds having nucleotide sequences of the mahogany gene as disclosed by WO 00/05373 which is incorporated herein by reference; and certain sapogenin compounds as disclosed by U.S. Pat. No. 4,680,289 which is incorporated herein by reference.

Other useful compounds include certain gamma peroxisome proliferator activated receptor (PPAR) agonists as disclosed by WO 01/30343 and U.S. Pat. No. 6,033,656 which are incorporated herein by reference and certain polypeptides such as fibroblast growth factor-10 polypeptides as disclosed by WO 01/18210 which is incorporated herein by reference.

Moreover, monoamine oxidase inhibitors that decrease energy intake or increase energy expenditure are useful with the practice of the present invention. Suitable, but non-limiting examples of monoamine oxidase inhibitors include befloxatone, moclobemide, brofaromine, phenoxathine, esuprone, befol, toloxatone, pirlindol, amiflamine, sercloremine, bazinaprine, lazabemide, milacemide, caroxazone and other certain compounds as disclosed by WO 01/12176 which is incorporated herein by reference.

Certain compounds that increase lipid metabolism are also useful with the practice of the present invention. Such compounds include, but are not limited to, useful evodiamine compounds as disclosed by U.S. Pat. No. 6,214,831 which is incorporated herein by reference.

Nutrient partitioning agents and digestive inhibitors are another strategy in the treatment of obesity by interfering with the breakdown, digestion or absorption of dietary fat in the gastrointestinal tract. Gastric and pancreatic lipases aid in the digestion of dietary triglycerides by forming them into free fatty acids that are then absorbed in the small intestine. Inhibition of these enzymes leads to inhibition of the digestion of dietary triglycerides. Non-limiting examples include a lipase inhibitor, orlistat, such as XENICAL™ capsules ((S)-2-formylamino-4-methyl-pentanoic acid (S)-1-[[(2S, 3S)-3-hexyl-4-oxo-2-oxetanyl]methyl]-dodecyl ester) commercially available from Roche Laboratories and certain benzoxazinone compounds as described by WO 00/40247 which is incorporated herein by reference.

Agents that increase energy expenditure are also referred to as thermogenic medications. Non-limiting examples of suitable thermogenic medications include xanthines, such as caffeine and theophylline, selective β-3-adrenergic agonists, for example certain compounds in U.S. Pat. No. 4,626,549 which is incorporated by reference herein, and α-2-adrenergic and growth hormones compounds as described in U.S. Pat. Nos. 4,937,267 and 5,120,713 which are incorporated by reference herein.

Generally, a total dosage of the above-described obesity control agents or medications, when used in combination with a compound of this invention can range from 0.1 to 3,000 mg/day, preferably from about 1 to 1,000 mg/day and more preferably from about 1 to 200 mg/day in single or 2-4 divided doses. The exact dose, however, is determined by the attending clinician and is dependent on such factors as the potency of the compound administered, the age, weight, condition and response of the patient.

Agents or drugs employed for increasing food intake and/or body weight include appetite stimulants such as megastrol acetate, adrenocorticoids such as prednisolone and dexamethasone, cyproheptidine, serotonergic drugs such as fenfluramine, neuropeptide Y, and androgen antagonists such as flutamide, nilutamide, and zanoterone.

Synthetic Methods of the Invention.

One general strategy includes developing a linear intermediate using chiral building blocks such as amino acid derivatives. The linear intermediate can be cyclized using a Mitsunobo reaction strategy or by spontaneous cyclization through reactive groups such as a reaction between an amine and an ester or between an amine and an aldehyde function. In these cyclizaiions, the driving force for intramolecular reaction versus intermolecular reaction is the thermodynamically favored reaction forming a six-membered ring structure. In many instances, the methodology incorporates conditions that do not involve inversion or racemization of chiral centers. In some instances where a small percentage of racemate is observed, such as in use of an a-amino aldehyde in the $R_3$ position, the desired chiral product is easily purified by methods known in the art, such as flash chromatography on a silica gel column.

Certain of the compounds of the invention are tri-substituted piperazine molecules, and can be generalized as having the following structures:

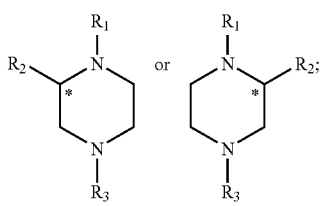

where $R_1$ is

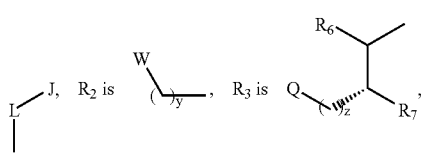

L, J, W, Q, $R_6$, $R_7$, y and z are as defined in the Summary of the Invention, and the carbon atom marked with an asterisk can have any stereochemical configuration. In the synthetic schemes that follow, such groups are sometimes referred to as $R_1$, $R_2$ and $R_3$, it being understood that such groups have the meaning given here.

Certain other compounds of the invention are tetra-substituted piperazine molecules, and can be generalized as having the following structures:

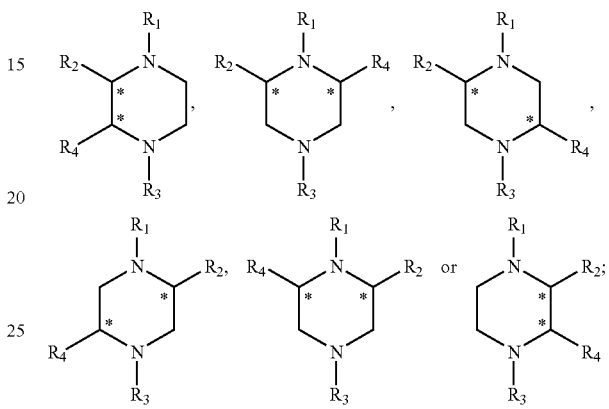

where $R_1$, $R_2$, and $R_3$ are as defined above, $R_4$ is a $C_1$ to $C_6$ linear or branched chain, including $CH_3$, a $C_1$ to $C_6$ linear chain or branched chain with an aryl group, or a $C_1$ to $C_6$ linear chain and a heteroatom unit with at least one cationic center, hydrogen bond donor or hydrogen bond acceptor, and the carbon atoms marked with an asterisk can have any stereochemical configuration.

Certain other compounds of the invention are penta-substituted piperazine molecules, and can be generalized as having the following structures:

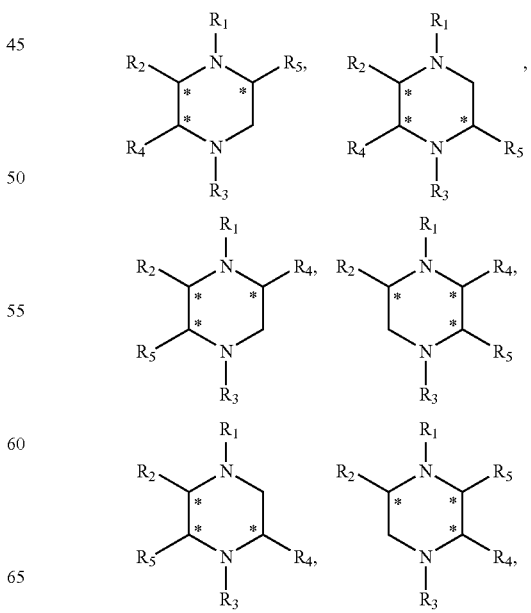

-continued

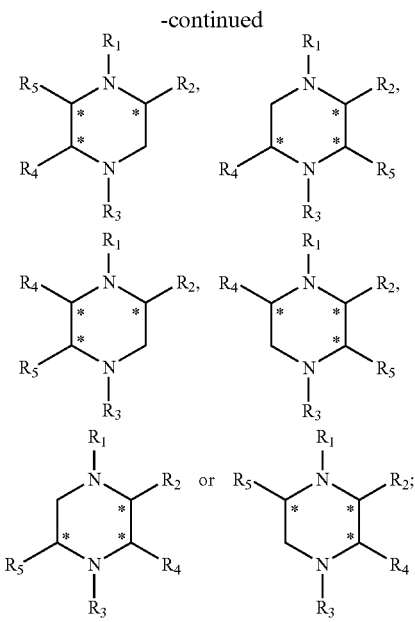

where $R_1$, $R_2$, and $R_3$ are as defined above, $R_4$ and $R_5$ are each independently a $C_1$ to $C_6$ linear or branched chain, including $CH_3$, a $C_1$ to $C_6$ linear chain or branched chain with an aryl group, or a $C_1$ to $C_6$ linear chain or branched chain and a heteroatom unit with at least one cationic center, hydrogen bond donor or hydrogen bond acceptor, and the carbon atoms marked with an asterisk can have any stereochemical configuration.

In the synthetic schemes that follow, groups are sometimes referred to as $R_1$, $R_2$, $R_3$, $R_4$ and $R_5$, it being understood that such groups have the meaning given here.

The methods disclosed herein thus allow for the synthesis of piperazine molecules with the diverse functionalities disclosed herein. Certain of the schemes further provide a facile approach to obtain compounds that differ at the $R_3$ group since this group is introduced after the cyclic intermediate has been synthesized.

It is further understood that for the $R_2$, $R_4$ and $R_5$ positions, such positions on the ring carbon include both a hydrogen atom and the specified group, such that the position includes such group in one of $R_{xa}$ or $R_{xb}$, and hydrogen in the remaining of $R_{xa}$ or $R_{xb}$. Thus, for example, $R_2$ may be in either the $R_{2a}$ or $R_{2b}$ position, with the remaining position being hydrogen. In one embodiment, $R_{2a}$ is -$L_2$-W and $R_{2b}$ is hydrogen, and in another embodiment, $R_{2a}$ is hydrogen and $R_{2b}$ is -$L_2$-W, and so on. It may thus be seen that all possible stereochemical configurations are included within the disclosure of this invention.

The $R_3$ position may be an amino acid residue or derivative thereof of the general formula given above, including but not limited to a D-amino acid selected from the group consisting of Phe, Phe(2-Cl), Phe(4-Cl), Phe(2,4-diCl), Phe(2,4-diF), Phe(3,4-diCl), Phe(4-NO$_2$), Phe(4-Me), Phe(4-Phenyl), HPhe, pF-Phe, Phe(4-Br), Phe(4-CF$_3$), Phe(3,4-diF), Phe(4-I), Phe(2-Cl, 4-Me), Phe(2-Me, 4-Cl), Phe(2-F, 4-Cl), Phe(2,4-diMe), Phe(2-Cl, 4-CF$_3$), Phe(3,4-di-OMe), Phg, Trp, Nal 1, Nal 2, Bip, Dip, Bpa, Ser(Bzl), Ser(2-Naphthyl), Ser(Phenyl), Ser(4-Cl-Phenyl), Ser(2-Cl-Phenyl), Lys(Z), Lys(Z-2'Br), Lys(Bz), Thr(Bzl), Tic, Tiq, Cys(Bzl), Tyr(2,6-DiCl-Bzl) and Tyr(Bzl), in each instance optionally further include a modified terminal amine, including a $C_1$ to $C_6$ linear or branched chain, a $C_1$ to $C_6$ linear or branched chain with an aryl group or an amine capping group.

In one embodiment, the $R_3$ position may be a group of the general formula given above which is made by use of an aldehyde derivative of a D-amino acid. By use of an α-amino aldehyde the resulting $R_3$ group has the general structure:

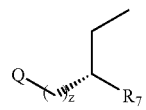

where the $R_6$ group is hydrogen. By way of example, where an aldehyde derivative of D-Phe is employed in synthesis, in the resulting compound $R_7$ may be $NH_2$, z may be 1, and Q may be phenyl. However, it can readily be seen that any D-amino acid listed above may be employed as an aldehyde derivative, and may further be seen that $R_7$ may be as generally defined, including any amine capping group, so long as $R_6$ is hydrogen. In synthesis, preferably an N-protected D-amino acid aldehyde is employed, where the N-protecting group is conventionally Boc or Fmoc. Because of the inherent instability of an α-amino aldehyde in solution, these compounds are preferably synthesized immediately prior to use. Two different methods are used for synthesis.

In the first method, to an N-protected amino acid (such as with a Boc- or Fmoc-group) in dichloromethane was added TBTU (1 equiv) (here and elsewhere "equiv" is an abbreviation for equivalent or equivalents, as the context requires) and NMM (1 equiv). The mixture was stirred for half an hour and N,O-dimethylhydroxylamine hydrochloride (1 equiv) and NMM (1 equiv) were added. The reaction was carried out overnight. The solvent was removed and EtOAc was added. The organic phase was washed by aqueous sodium bicarbonate, brine and dried over sodium sulfate. After evaporation of solvent and drying under vacuum the residue was dissolved in THF under nitrogen at −78° C. To this solution was added LAH (1 M in THF, 1.5 equiv) slowly. The solution was stirred for an additional half hour. The reaction was diluted by ether and quenched by aqueous potassium hydrogen sulfate. The organic phase was washed with 1 N HCl, water, brine and dried over sodium sulfate. After removal of solvent the aldehyde was used immediately for the next step reaction without purification.

In the second method, to an N-protected amino acid (such as with a Boc- or Fmoc-group) in THF was added borane-THF (1 M, 1.2 equiv) slowly at 0° C. The temperature was raised to room temperature and the solution stirred for 2 hours. The reaction was quenched by 1 N HCl and the solvent was evaporated. The crude product was purified on a silica gel column to give a pure N-protected amino alcohol. This alcohol was dissolved in dry dichloromethane and Dess-Martin periodinane (1.1 equiv) was added. The solution was stirred for 1 hour and the reaction was diluted by ether. The organic phase was washed by saturated sodium bicarbonate with 10% sodium thiosulfate, then water, then brine and dried over sodium sulfate. After removal of solvent the crude product was used for the next step reaction immediately without further purification.

In the synthetic methods that follow, either of the foregoing methods may be employed to utilize a D-amino acid aldehyde.

Scheme 1: Synthesis of 1,2,4-substituted Piperazine Derivatives

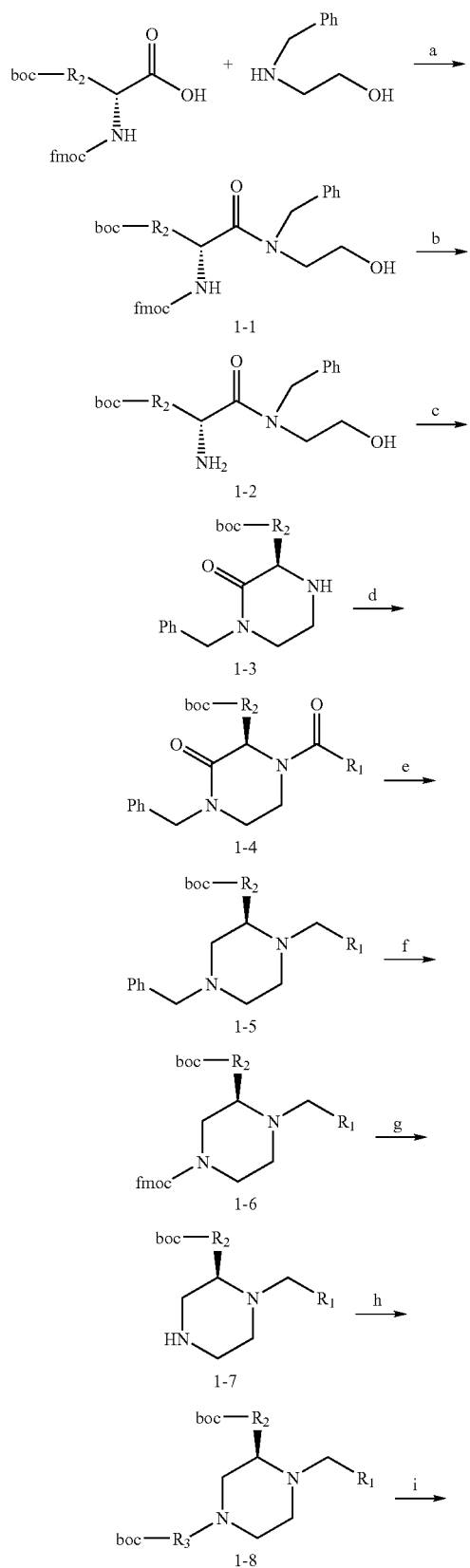

a) TBTU, NMM, EtOAc; b) 20% Et$_2$NH/EtOAc; c) Ph$_3$P, DIAD, EtOAc; d) R$_1$ acid, HOAt, EDC, NMM, DMF; e) AlH$_3$-TEA; if necessary, followed by (i) TFA/DCM, ii) NMM, BPC, CH$_3$CN; f) Fmoc—Cl, CH$_3$CN; g) 20% Et$_2$NH/EtOAc; h) EDC, HOAt, NMM, DMF, Boc—R$_3$; i) TFA/DCM An amino acid residue that includes R$_2$, preferably with a protected R$_2$ group, most preferably a Boc protected R$_2$ group, is employed. The side chain of the residue forms the R$_2$ group, and thus residues such as Orn, D-Orn, Arg or D-Arg may be employed. In one embodiment, Fmoc-D-Orn(Boc)-OH or Fmoc-Orn(Boc)-OH are employed, resulting in an L group that is (CH$_2$)$_3$ and a W group that is NH$_2$. In another embodiment, a guanidine group was added by treating compound 1-5 with 30% TFA in dichloromethane for 30 min. then with NMM (1 eq.) and N,N'-Bis(t-butoxycarbonyl)-1H-pyrazole-1-carboxamidine (BPC),(1 eq.) in acetonitrile overnight at room temperature. This results in an L group that is (CH$_2$)$_3$ and a guanidine group for W. In yet another embodiment, as set forth in Example 7, a solution of Fmoc-D-Orn(Boc)-OH (2.27 g, 5.0 mmol), N-benzylethanolamine (1.5 g, 10.0 mmol), and NMM (0.72 mL, 6.5 mmol) in 50 mL of EtOAc was employed, to which was added TBTU (2.07 g, 6.5 mmol) at room temperature. After stirring at room temperature overnight, the reaction mixture was diluted with 50 mL of EtOAc. The organic phase washed with 1 N HCl (2 times), H$_2$O (2 times), saturated aqueous NaCl (1 time), and dried over MgSO$_4$. After solvent was evaporated, the crude product (1-1) was used for the next reaction without further purification.

Compound 1-1 was treated with 24 mL of EtOAc and 6 mL of Et$_2$NH at room temperature for two hours with stirring. After completion of reaction, solvent was evaporated and co-evaporated with EtOAc once more. The crude product (1-2) was used for the next reaction without further purification.

Compound 1-2 was dissolved in 50 mL of EtOAc, and to the solution were added Ph$_3$P (1.97 g, 7.5 mmol) and DIAD (1.2 mL, 6.0 mmol). The reaction mixture was stirred at room temperature for 1.5 hours. The solvent was removed and the residue was purified by flash column chromatography (using EtOAc:hexane at 3:1, EtOAc, then acetone as eluents). The product (1-3) was obtained as a yellow solid (1.45 g, 84% overall yield for the last 3 steps).

An acid form of R$_1$ was employed to introduce the R$_1$ group. Compounds so employed include 2-naphthylacetic acid, 1-naphthylacetic acid, benzoic acid, 3-indoleacetic acid, and 3-phenylpropionic acid. In one embodiment, to a solution of 1-3 (0.85 g, 2.35 mmol), 2-naphthylacetic acid (438 mg, 2.35 mmol), HOAt (4.7 mL, 2.35 mmol), NMM (0.26 mL, 2.35 mmol) in 5 mL of DMF was added EDC (451 mg, 2.35 mmol). The reaction mixture was stirred at room temperature overnight. After removing DMF the residue was diluted with EtOAc. The organic layer was washed with 1 N HCl, H$_2$O (2 times), 1 N NaOH, H$_2$O (2 times) and brine, then dried over MgSO$_4$. The solvent was evaporated in vacuo. The obtained crude product (1-4) was a yellow soft solid (1.2 g), which was used for the next reaction without further purification.

Under nitrogen at 0° C. to the solution of compound 1-4 (0.80 g, 1.50 mmol) in 12 mL of anhydrous THF was added AlH$_3$-TEA (0.5 M, 6.0 mmol) dropwise. The reaction was carried out at room temperature for 1.5 hours and quenched at 0° C. with 5 mL of 6 N HCl, then diluted with EtOAc and neutralized with saturated NaHCO$_3$ to pH ~7. The solution was then extracted with EtOAc (3 times). The combined organic layers were washed with brine (2 times), dried and concentrated in vacuo. The crude product (1-5) was obtained as a brown oil (380 mg), which was used for the next reaction without further purification.

A mixture of 1-5 (225 mg, 0.46 mmol) and Fmoc-Cl (179 mg, 0.69 mmol) was stirred in 10 mL of acetonitrile at room temperature for 1 hour. The solvent was evaporated and the crude product (1-6) as obtained as a yellow oil, which was used for the next reaction without further purification.

Compound 1-6 was treated with 1 mL of diethyl amine in 4 mL of EtOAc at room temperature overnight, after evaporation of solvent and purification by flash column chromatography (using acetone:MeOH 10:1 to 5:1 as eluents) to yield a white solid (1-7) (50 mg, 32%).

The R$_3$ group was added following the same procedure as with compound 1-3, but using compound 1-7 and Boc-R$_3$ as starting materials. Boc-R$_3$ may be any amino acid residue meeting the definition for R$_3$, such as for example any substituted or unsubstituted Boc-L- or -D-Phe-OH residue. In the embodiment of Examples 1 through 8, Boc-D-Phe(4-Cl)—OH was employed as the starting material, and to a solution of 1-7 (0.85 g, 2.35 mmol), Boc-D-Phe(4-Cl)—OH (438 mg, 2.35 mmol), HOAt (4.7 mL, 2.35 mmol), and NMM (0.26 mL, 2.35 mmol) in 5 mL of DMF was added EDC (451 mg, 2.35 mmol). The reaction mixture was stirred at room temperature overnight. After removing DMF the residue was diluted with EtOAc. The organic layer was washed with 1 N HCl, H$_2$O (2 times), 1 N NaOH, H$_2$O (2 times) and brine, and then dried over MgSO$_4$. The solvent was evaporated in vacuo. The crude product was purified by flash column chromatography (using hexane:AcOEt at 1:1 as eluent) to give 1-8.

Compound 1-8 was treated with TFA/DCM (1 mL/2 mL) at room temperature for 1 hour to remove the Boc groups on R$_2$ and R$_3$. The resulting reaction mixture was concentrated and the crude product was purified by HPLC to yield final product 1-9.

Scheme 2: Synthesis of tetra-substituted piperazine compounds

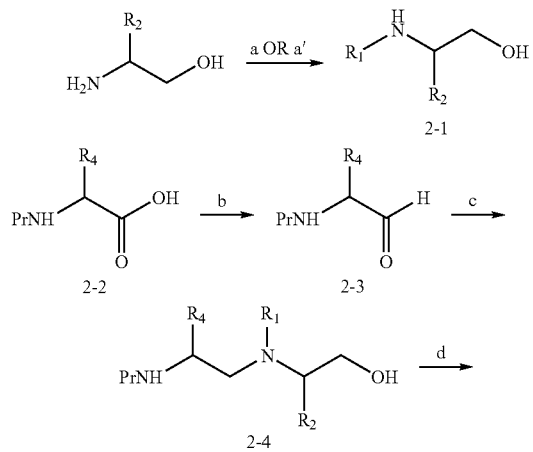

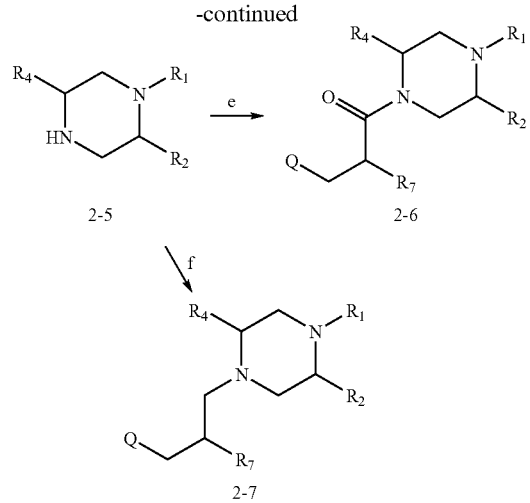

Reagents: (a) i) HOAt, EDC, DMF; ii) NaBH$_4$, HOAc, Dioxane, reflux; OR R$_1$Br, K$_2$CO$_3$, DMF; OR R$_1$—Br, Pd$_2$dba$_3$, BINAP, NaO$^t$Bu; (a') 4A molecular sieves, Aldehyde, NaBCNH$_3$, HOAc/THF. (b) i) NHMeOMe, HCl, TBTU, NMM; ii) LAH, THF; (c) 4A molecular sieves, Compound 2-1, NaBCNH$_3$, HOAc/THF. (d) i) 20% Et$_2$NH/EtOAc; ii) Ph$_3$P, DIAD, THF; (e) i) (QCH$_2$)CHR$_7$—COOH, HOAt, DIC, DMF; ii) TFA/DCM; (f) i) (QCH$_2$)CHR$_7$—CHO, 4A molecular sieves, NaBCNH$_3$, HOAc/THF; ii) TFA/DCM.

To a solution of L-J-COOH (where L and J are as defined above, such as where L-J-COOH is naphthylacetic acid) and 1-hydroxy-7-azabenzotriazole (1 equiv) in dry N,N-dimethylformamide is added 1-(3-dimethylaminopropyl)-3-ethylcarbodiimide hydrochloride (1 equiv). After the mixture is stirred at room temperature for one-half hour, a chiral amino alcohol (e.g., an (R) or (S) 2-amino-2-R$_2$ group-1-ethanol, which would afford an R$_2$ group) (1 equiv) is added. The reaction is continued for 16 hours. The reaction mixture is poured into water and extracted by EtOAc twice. The organic layer is washed by 1 N hydrochloric acid twice, 1 N sodium hydroxide twice, brine and dried over sodium sulfate. After evaporation, the product is purified on silica gel column with 10% methanol in methylene chloride.

To this product (1 equiv) and sodium borohydride (5 equiv) in dioxane is added acetic acid (5 equiv) in dioxane slowly. After completion, the mixture is refluxed for 2 hours. The reaction is quenched by water. The product is extracted from ether by 1 N hydrochloric acid. The pH value of the resulting aqueous solution is adjusted by potassium hydroxide to ~11, and the product extracted by ether three times. The organic layer is dried over sodium sulfate and the solvent evaporated. The obtained compound 2-1 is used for the next step reaction without further purification.

Alternatively, an aliphatic bromide (1 equiv) is stirred with the amino alcohol and potassium carbonate in DMF overnight at room temperature. The reaction mixture is poured into water and extracted by EtOAc twice. The organic layer is washed by aqueous sodium bicarbonate, brine and dried over sodium sulfate. After evaporation, the product can be used for the next step without purification. When an aromatic bromide is reacted with a chiral amino alcohol the reaction is conducted in the presence of tris(dibenzylideneacetone)dipalladium(0) (Pd$_2$dba$_3$) (0.05 equiv), 2,2'-bis(diphenylphosphino)-1,1'-binaphthyl (BINAP) (0.15 equiv) and sodium t-butoxide (1.5 equiv) in toluene at 90° C. for 6 hours. The solution is concentrated and dissolved in methylene chloride, which is subsequently passed through a celite column. Purification by silica gel column yields pure product 2-1.

Alternatively, a mixture of amino alcohol and the desired aldehyde (for example, a Boc- or Fmoc-protected amino acid aldehyde) is stirred in the presence of activated 4 Å molecular sieves (1 g) in dry THF (10% acetic acid) for 1 hour. Sodium cyanoborohydride (1 equiv, 1 M solution in THF) is added to this mixture. After 2 hours, solvent is evaporated and the desired product (2-4) purified on silica gel column.

To compound 2-2, an N-protected amino acid with its side chain group appearing as $R_4$ (1 equiv), and NMM (1 equiv) in dry dichloromethane is added TBTU (1 equiv). The mixture is stirred at room temperature for 30 minutes. A mixture of N,O-dimethylhydroxyamine hydrochloride (1.5 equiv) and NMM (1.5 equiv) in DCM is stirred for 30 minutes. These two mixtures are combined and stirred at room temperature for 18 hours. The organic solvent is evaporated and the residue loaded on a flash chromatograph column and eluted with EtOAc/hexane (2/1) to yield an N,O-dimethylhydroxyamide product. This product is dissolved in dry THF at 0° C. and LAH (1 M in THF, 1.2 equiv) is added slowly. After 30 minutes the reaction is quenched by aqueous potassium hydrogen sulfate (1.2 equiv). THF is removed and ether is added. The solution is washed by 1 N HCl (2 times), aqueous sodium hydrogen carbonate and brine, and dried over sodium sulfate. The solvent is removed under vacuum to give compound 2-3. Compound 2-3 is used for next step reaction without further purification.

A mixture of compound 2-3 and compound 2-1 is stirred in the presence of activated 4 Å molecular sieves (1 g) in dry THF (10% acetic acid) for 1 hour. Sodium cyanoborohydride (1 equiv, 1 M solution in THF) is added to this mixture. After 2 hours, solvent is evaporated and the desired product (2-4) purified on a silica gel column.

Compound 2-4 is treated with 20% diethylamine in EtOAc for 12 hours, with the solvent evaporated to dryness. The residue and TPP (3 equiv) is dissolved in dry THF. To this solution is added diisopropyl azodicarboxylate (3 equiv) in THF slowly at 0° C. The reaction is continued for 16 hours at room temperature. The product 2-5 is purified by a silica gel column after evaporation of solvent.

The $R_3$ group is introduced in compound 2-5 in the following manner. Compound 2-5 is coupled with an appropriate amino acid, such as substituted or unsubstituted D-Phe or a derivative or homolog thereof, (2 equiv) by use of HOAt (2 equiv) and 1,3-diisopropylcarbodiimide (2 equiv) in DMF solution overnight at room temperature. Flash chromatograph (EtOAc/hexane=2) gives the product with protecting groups. The Fmoc group is removed by treatment with 20% diethyl amine in EtOAc, and the Boc group is removed by treatment with 30% TFA in methylene chloride for 1 hour, as applicable to the compounds. The final pure compound (2-6) is obtained by purification on HPLC.

Compound 2-7 is synthesized by a method similar to that described for compound 2-4. A suitable aldehyde, such as an N-protected α-amino aldehyde derived from an N-protected amino acid as described above, is employed. A mixture of compound 2-5 and the aldehyde is stirred in the presence of activated 4 Å molecular sieves (1 g) in dry THF (10% acetic acid) for 1 hour. Sodium cyanoborohydride (1 equiv, 1 M solution in THF) is added to this mixture. After 2 hours, solvent is evaporated and the product purified on a silica gel column. Flash chromatograph gives the product with protecting groups. The Fmoc group is removed by treatment with 20% diethyl amine in EtOAc, and the Boc group is removed by treatment with 30% TFA in methylene chloride for 1 hour, as applicable to the compounds. The final pure compound (2-7) is obtained by purification on HPLC.

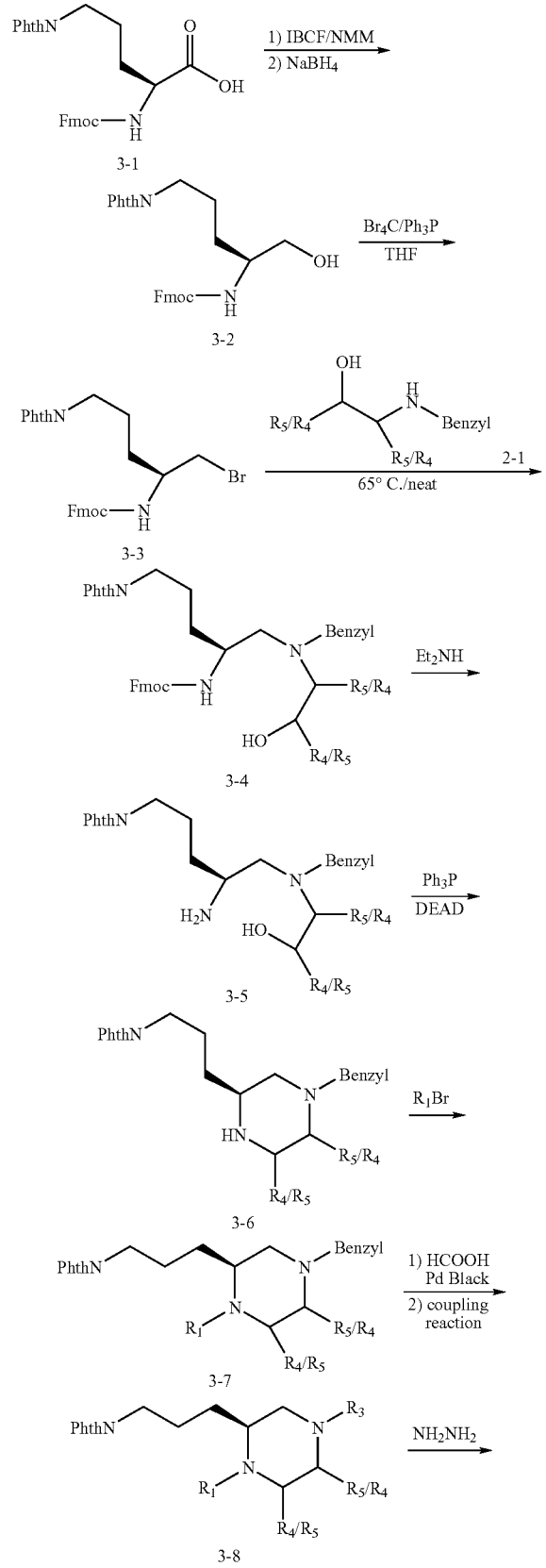

Scheme 3: Synthesis of penta-substituted piperazine compounds

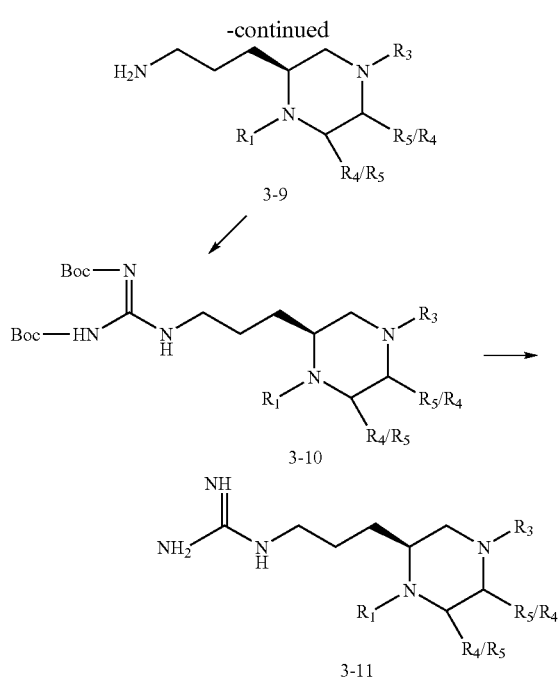

2-Benzyloxycarbonylamino-5-phthalimido-pentanoic acid (3-1) is synthesized from a mixture of Fmoc-ornithine (1.33 g, 5.0 mmol), N-carboethoxy-phthalimide (1.10 g, 5.0 mmol), and TEA (1.0 mL, 6.0 mmol) in 10 mL of dry THF and refluxed overnight. The solvent is evaporated in vacuo, the residue dissolved in EtOAc, and washed successively with 1 N HCl, water, brine, dried (MgSO$_4$) and evaporated in vacuo to afford the crude product, which is used for the next reaction without further purification.

The crude product (3-1) is dissolved in 5 mL of THF and to the solution is added NMM (0.44 mL). The solution is cooled to −15° C. with a salt-ice bath, and IBCF (0.52 mL, 1 equiv) added. After 10 minutes, the reaction mixture is filtered to remove formed solid salt. The solid is washed twice with adequate amounts of THF. The filtrate is cooled to −10° C. and to it is added NaBH$_4$ (0.23 g, 1.50 equiv) in 2 mL of water. The reaction mixture is stirred for another 15 minutes, and then concentrated in vacuo. The residue is dissolved in EtOAc and washed successively with 10% citric acid, saturated NaHCO$_3$, H$_2$O and saturated NaCl, and then dried (MgSO$_4$) and concentrated in vacuo. The crude product is purified with column chromatography eluted with 1:1 EtOAc:hexane. The purified product, [4-Phthalimido-1-hydroxymethyl-butyl]-carbamic acid benzyl ester (3-2), is obtained as a white solid.

At −20° C. under N$_2$ to the suspension of 3-2 (253 mg, 0.66 mmol) and TPP (260 mg, 1.5 equiv) in toluene is added tetrabromocarbon (242 mg, 1.1 equiv) and the reaction mixture stirred at room temperature overnight. The reaction mixture is concentrated in vacuo and the crude product purified by column chromatography eluted with hexane and EtOAc (2:1). The purified product, [1-Bromomethyl-4-phthalimido-butyl]-carbamic acid benzyl ester (3-3), is obtained as a white solid.

A mixture of 3-3 (400 mg, 0.90 mmol) and an amino alcohol (2-1) synthesized according to Scheme 2 (400 mg, 1.86 mmol) in 2 mL of DCM is stirred at 65° C. The solvent is evaporated and the dried reaction mixture heated at 65° C. for 2 hours. The formed crude product is purified by column chromatography and eluted with hexane and EtOAc (1:2) to give 3-4.

At room temperature 3-4 is treated with 20% diethylamine in EtOAc for 2 hours. The solvent is removed and the residue 3-5 is used for the next step reaction.

At 0° C. under nitrogen to the mixture of 3-5 (150 mg, 0.34 mmol) and TPP (133 mg, 1.5 equiv) in 10 mL of anhydrous THF is added diethyl azodicarbonate (65 mg, 1.1 equiv) in 1 mL of anhydrous THF. After stirring at room temperature for 4 hours, the reaction mixture is evaporated in vacuo and the crude product purified by column chromatography. The product 3-6 is obtained.

Compounds 3-7 are made by the procedures described in method of synthesis of compound 2-1.

At room temperature under nitrogen a mixture of 3-7 (240 mg, 0.41 mmol) and palladium black (80 mg) in 21 mL of 4% formic acid in methanol is stirred vigorously for 1 hour. The reaction mixture is filtered and the filtrate is neutralized with saturated NaHCO$_3$. The methanol is evaporated and the residue dissolved in EtOAc and washed successively with saturated NaHCO$_3$, water and saturated NaCl, then dried (MgSO$_4$) and solvent is evaporated. To this residue is added a mixture of a desired carboxylic acid (1.5 equiv), HOAt (1.5 equiv) and diisopropylcarbodiimide (1.5 equiv) in anhydrous DMF. This coupling reaction introduces the R$_3$ group in the molecule. Various other R$_3$ groups can be introduced in a similar manner by using appropriate protected amino acid residues, such as substituted D-Phe analogs and homologs. The reaction mixture is stirred at room temperature overnight. The solvent is evaporated in vacuo and the crude product purified by column chromatography (eluted with hexane and EtOAc, 1:2) to give purified product 3-8.

A solution of 3-8 (30 mg) in 10 mL of 0.2 M hydrazine in methanol is stirred at room temperature for 19 hours. Mass spectroscopy shows no starting material left in the reaction mixture. The reaction mixture is evaporated and co-evaporated three times with methanol and once with EtOAc, then dried under high vacuum for 2 days. The crude product 3-9 (about 30 mg) is used for the next reaction without further purification.

The crude product 3-9 is reacted with 1,3-bis(tert-butoxycarbonyl)-2-methyl-2-thiopseudourea (1.1 equiv) and silver nitrate (1.1 equiv) and NMM (2.2 equiv) in 5 mL of acetonitrile at room temperature for 24 hours, followed by evaporation to remove the solvent and column chromatography purification to produce the 3-10. Product 3-10 (4.5 mg) is treated with 33% TFA in DCM at room temperature for 2 hours and the reaction mixture concentrated and purified with HPLC to give the final compound 3-11.

Scheme 4: Alternative synthesis of tetra-substituted piperazine compounds

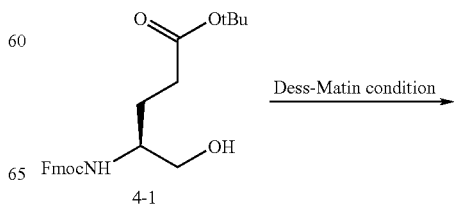

-continued

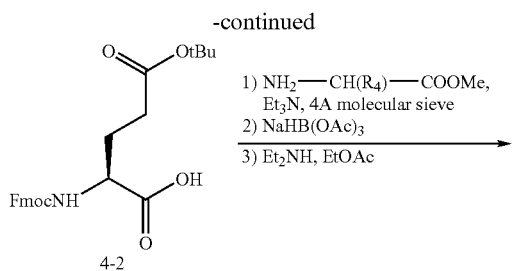
4-2

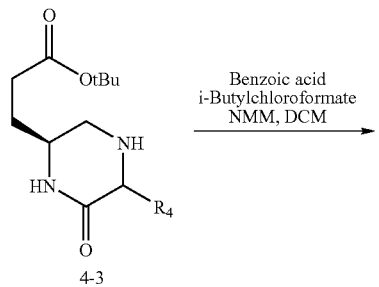
4-3

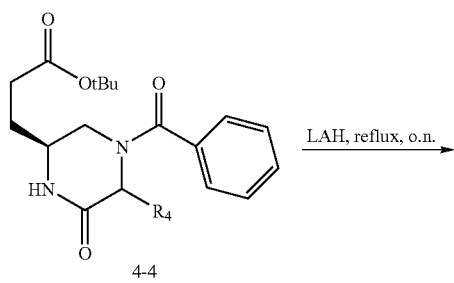
4-4

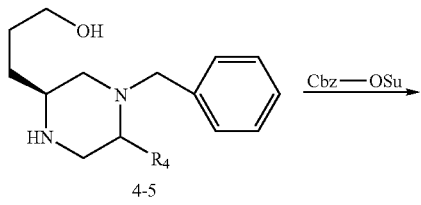
4-5

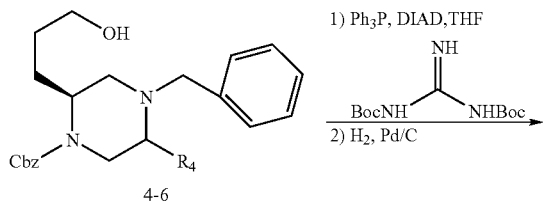
4-6

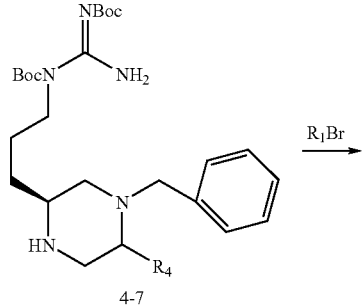
4-7

-continued

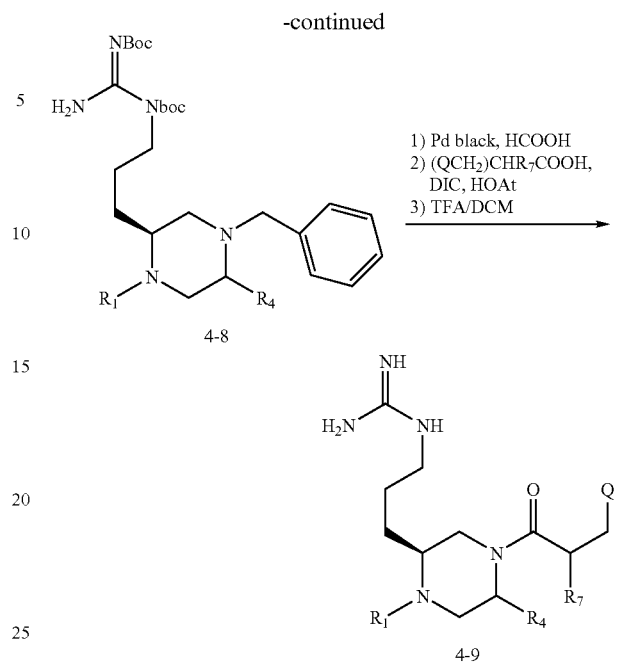

4-8

4-9

To a solution of compound Fmoc-Glutamol(OBut) (4-1) in DCM, 1,1,1-triacetoxy-1,1-dihydro-1,2-benziodoxol-3(1H)-one (1.1 equiv) is added in portions. After stirring for 30 minutes at room temperature the solution is diluted with ether, followed by addition of 25% sodium thiosulphate in an aqueous solution saturated with sodium bicarbonate. The mixture is stirred for an additional 5 minutes and the desired compound is extracted by EtOAc. The organic layer is washed with saturated bicarbonate solution, water and subsequently dried over magnesium sulfate. After evaporation of solvent, compound 4-2 is obtained for the next step reaction without further purification.

A mixture of compound 4-2, an (R) or (S) alpha amino acid methyl ester with its side chain appearing as $R_4$ in the final compound 4-8 (1 equiv), and TEA (1 equiv) in the presence of 4 Å molecular sieve in dry THF is stirred for two hours. After addition of sodium triacetoxyborohydride (1.5 equiv) the mixture is stirred for an additional 16 hours. The solid is removed by filtration and the product extracted by EtOAc from water. The organic layer is dried over sodium sulfate. After evaporation of solvent the residue is dissolved in EtOAc containing 20% diethylamine. The reaction is carried out for 16 hours and solvent removed under vacuum. The product 4-3 is obtained after purification by chromatography.

To a solution of benzoic acid (1 equiv) and NMM (1 equiv) in dichloromethane at −15° C. is added isopropyl chloroformate (1 equiv) slowly. The reaction mixture is stirred for 30 minutes and compound 4-3 subsequently added. After 30 minutes the reaction temperature is raised to room temperature and the mixture stirred for 16 hours. The solvent is evaporated and the residue purified on a column to give compound 4-4.

To the solution of compound 4-4 in THF is added LAH (in THF, 4.5 equiv) slowly. The reaction is conducted at room temperature for 2 hours and refluxing temperature for 16 hours. After cooling down, the reaction mixture is treated with water, 15% sodium hydroxide and again water. The white solids are removed by filtration and solvent is evaporated. The residue contains compound 4-5, which is used for the next step reaction without further purification.

Compound 4-5 and N-(benzyloxylcarbonyloxy)succinimide (1.5 equiv) is dissolved in acetonitrile. The mixture is stirred for 16 hours. The solvent is evaporated and residue re-dissolved in methanol. To this solution is added 1 N sodium hydroxide (1.5 equiv). The mixture is stirred for an additional 16 hours. After evaporation of solvent the residue is purified on a column to afford compound 4-6.

To a mixture of compound 4-6, TPP (3 equiv) and 1,3-Bis(tert-butoxycarbonyl) guanidine (3 equiv) in toluene is added diisopropyl azodicarboxylate (3 equiv) slowly at 0° C. The reaction mixture is stirred for 16 hours at room temperature. After evaporation of solvent the residue is purified on a column to give the desired compound. This compound is subject to treatment with hydrogen in the presence of a catalytic amount of palladium on carbon (10%) in methanol. After 16 hours the solvent is evaporated and the residue purified on a column to give compound 4-7.

Compound 4-8 is synthesized by the method described in Scheme 2 for compound 2-1.

The benzyl group in compound 4-8 is removed by the method described in the synthesis of compound 3-8. The resulting compound is coupled with desired amino acids (2 equiv) by use of HOAt (2 equiv) and 1,3-diisopropylcarbodiimide (2 equiv) in DMF solution overnight at room temperature to introduce an $R_3$ moiety in the molecule. Flash chromatograph gives the product with protecting groups. The Fmoc group is removed by treatment with 20% diethyl amine in EtOAc and the Boc group is removed by treatment with 30% TFA in methylene chloride for 1 hour, as applicable to the compounds. The final pure compounds (4-9) are obtained by purification on HPLC.

Scheme 5: Alternative synthesis of tetra-substituted piperazine compounds

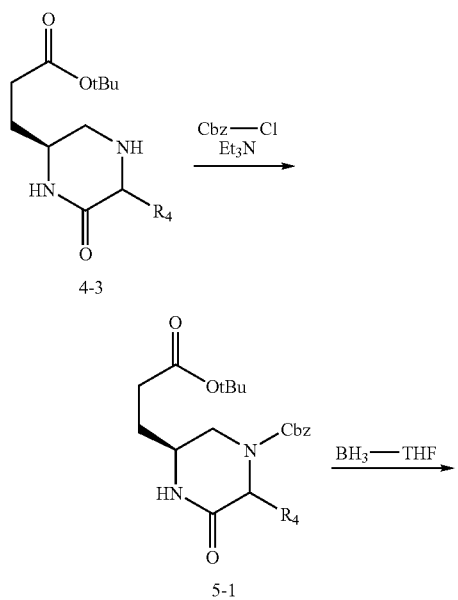

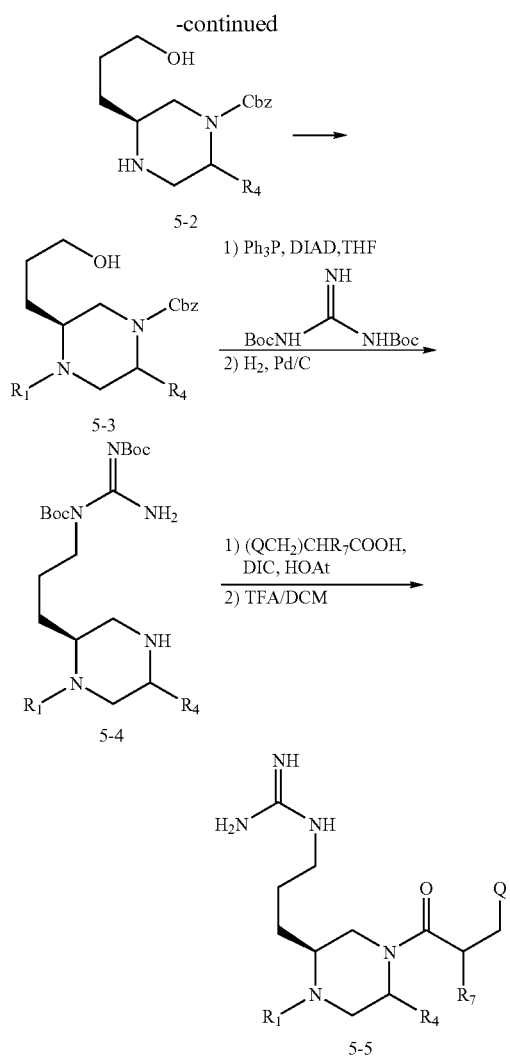

To a solution of compound 4-3 and TEA (1 equiv) in DCM at 0° C., benzyl chloroformate (1 equiv) is added slowly. The reaction is carried out overnight. After evaporation of solvent the product is purified on a column to give 5-1.

Compound 5-1 is dissolved in dry THF, to which borane in THF (1 M solution, 5 equiv total) is added. This solution is stirred for 16 hours. The reaction is quenched with 1 N HCl and the solution subsequently neutralized by 1 N NaOH. The product is extracted by EtOAc and the organic layer then washed by water and brine and dried over sodium sulfate. The solvent is evaporated and the dried product 5-2 used for next reaction step.

Compound 5-3 is synthesized by the method described for the synthesis of compound 1-1.

To a mixture of compound 5-3, TPP (3 equiv) and 1,3-Bis(tert-butoxycarbonyl)guanidine (3 equiv) in toluene is added diisopropyl azodicarboxylate (3 equiv) slowly at 0° C. The reaction mixture is stirred for 16 hours at room temperature. After evaporation of solvent the residue is purified on a column to give the desired compound. This compound is subject to treatment with hydrogen in the presence of a catalytic amount of palladium on carbon (10%) in methanol. After 16 hours the solvent is evaporated and the residue purified on a column to give compound 5-4.

Compound 5-4 is coupled with (QCH$_2$)CHR$_7$—COOH (1.5 equiv) by use of 1-hydroxy-7-azabenzotriazole (1.5 equiv) and 1,3-diisopropylcarbodiimide (1.5 equiv) in DMF solution overnight at room temperature, where Q is any group as described above. Flash chromatograph yields the product with Boc groups. The Boc groups are subjected to treatment with TFA/DCM (50/50) for one hour. After evaporation of solvent the final compound 5-5 is purified on HPLC.

Scheme 6: Alternative synthesis of tetra-substituted piperazine compounds

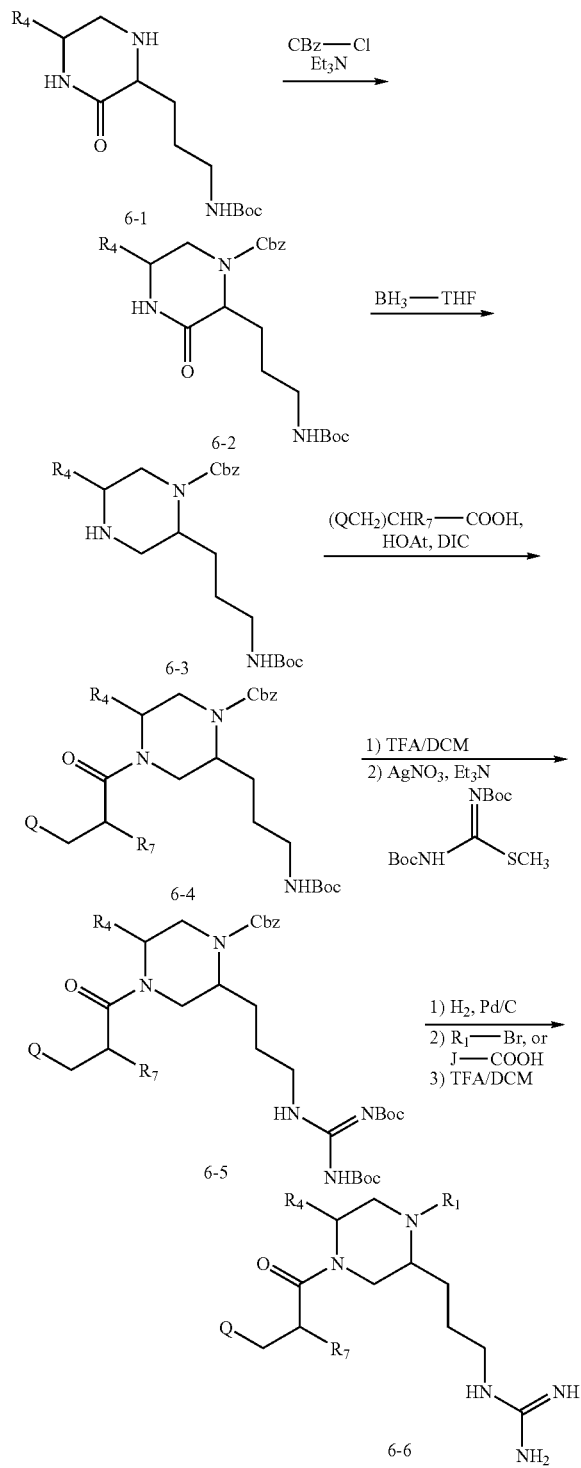

Compound 6-1 is synthesized by the methods described for compound 4-3. The starting material is an R or S isomer of an Fmoc-amino alcohol, such as for example alaninol. The aldehyde thus obtained is then reacted with Orn(Boc)-OMe under reductive amination conditions with cyclization giving compound 6-1 after removal of the Fmoc group. Thereafter compound 6-2 is synthesized by a method similar to that described for compound 5-1; compound 6-3 is synthesized by a method similar to that described for compound 5-2; compound 6-4 is synthesized by a method similar to that described for compound 5-5; and compound 6-5 is synthesized by a method similar to that described for compound 3-10.

Compound 6-5 is treated with hydrogen in the presence of a catalytic amount of palladium on carbon at room temperature for 16 hours. After filtration the solvent is evaporated and the resulting compound processed to give compound 6-6 in a manner similar to that for the synthesis of compounds 2-1 or 6-4, with subsequent treatment using TFA in methylene chloride. The final compound is purified by HPLC.

Scheme 7: Alternative synthesis of tetra-substituted piperazine compounds

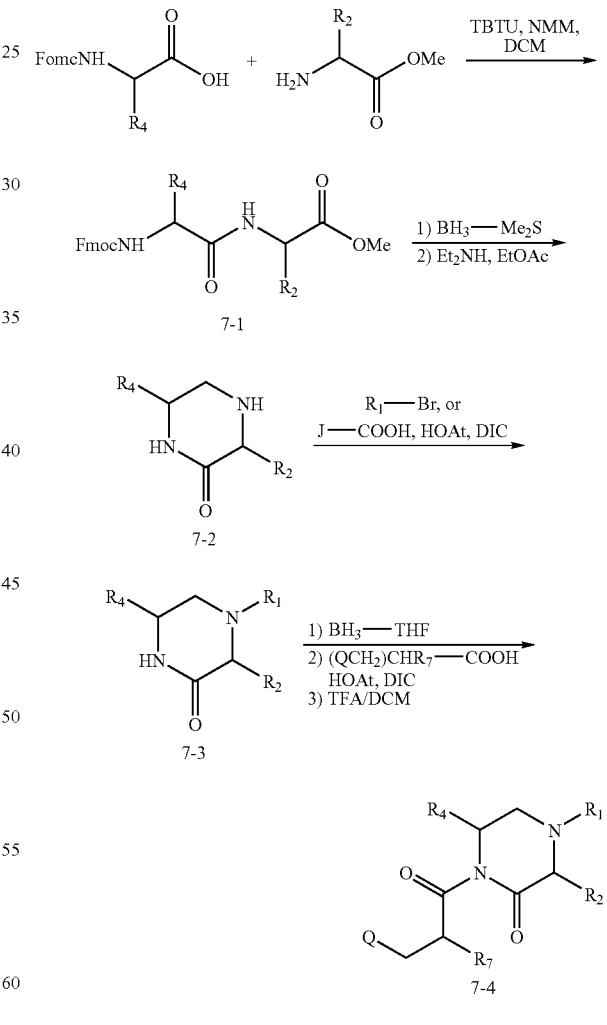

To an Fmoc-aliphatic amino acid or an appropriate di-basic amino acid derivative, such as Fmoc-Orn(Boc)-OH, and NMM (1 equiv) in dry DCM is added TBTU (1 equiv). The mixture is stirred at room temperature for 30 minutes. Separately, a mixture of an aliphatic amino acid methyl ester or an appropriate dibasic amino acid methyl ester, such as Orn (Boc)-OMe hydrochloride (1 equiv), and NMM (1 equiv) in DCM, is stirred for 30 minutes. These two mixtures are combined and stirred at room temperature for 16 hours. The organic solvent is evaporated and the residue extracted by EtOAc. The organic layer is washed by 1 N NaOH, water, 1 N HCl, water, brine and dried over sodium sulfate. The solvent is evaporated and the residue purified on a column to give compound 7-1.

Compound 7-1 is treated with $BH_3$-dimethyl sulfide (3 equiv) in THF overnight. The reaction is quenched with methanol and the solvent is removed. The residue is dissolved in EtOAc and washed with 1 N NaOH, brine and dried over sodium sulfate. After removing the solvent it is treated with 20% diethyl amine in EtOAc overnight at room temperature. The solvent is evaporated and the residue purified on a column to give 7-2.

Thereafter, compound 7-3 is synthesized by a method similar to that described for compounds 2-1 or 6-4, with the final compound 7-4 synthesized by a method similar to that described for compounds 6-3 and 6-4.

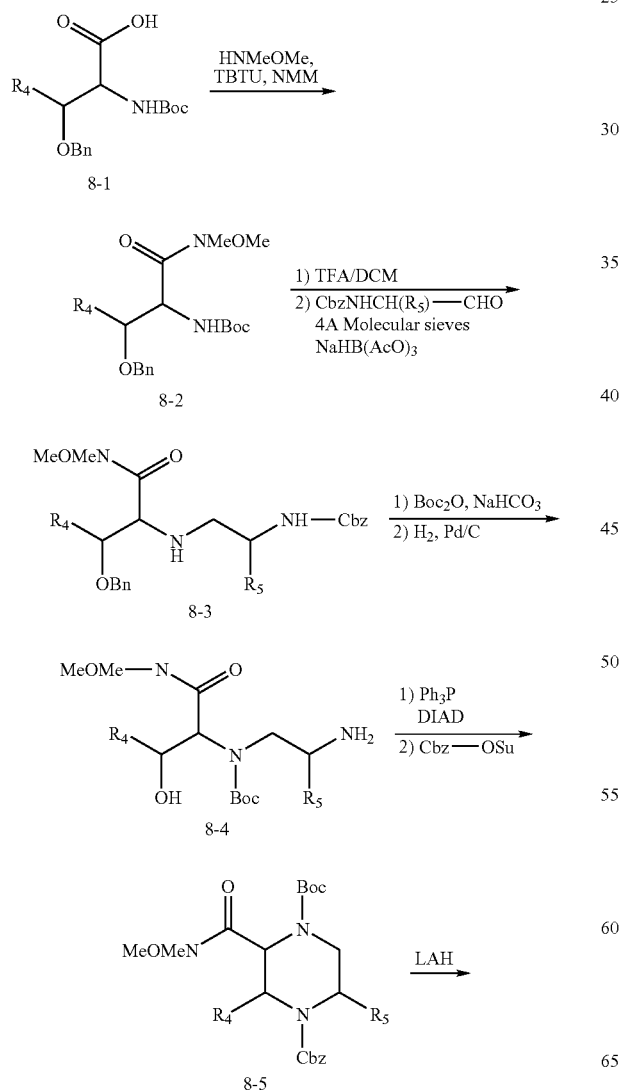
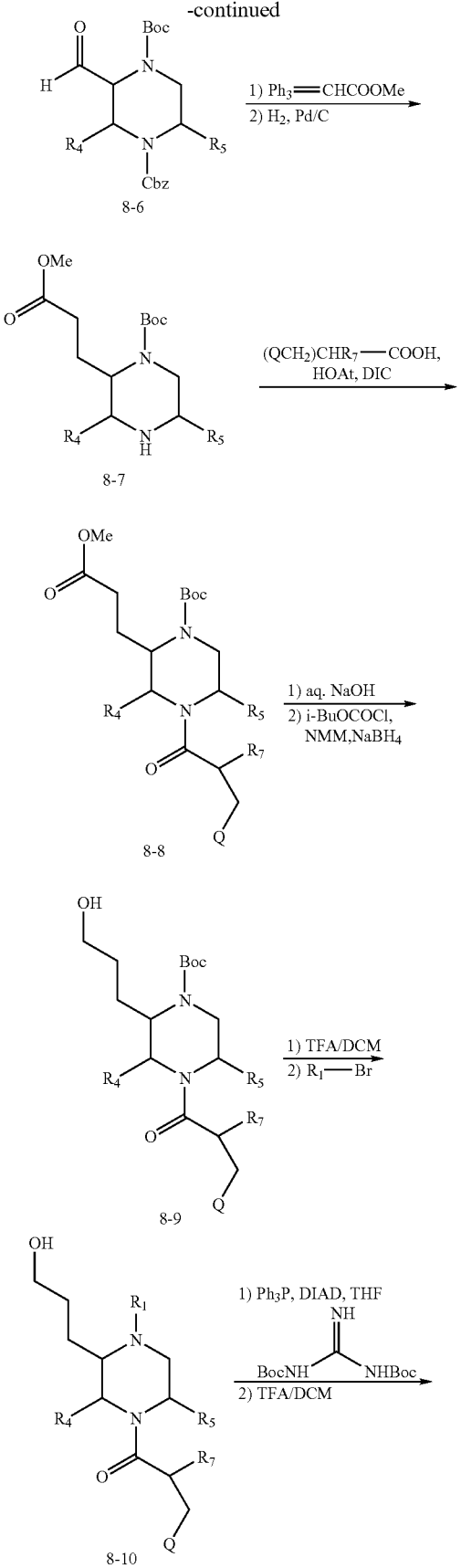

-continued

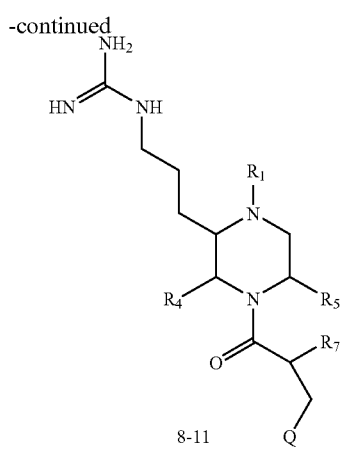

8-11

Compound 8-2 is synthesized by the method described in 2-3. The starting materials are protected beta-functionalized amino acids, such as L- or D-threonine or L- or D-allothreonine (8-1).

Compound 8-2 is treated with 30% TFA in methylene chloride for 1 hour. After evaporation of solvent the residue is dissolved in EtOAc. The organic phase is washed with sodium carbonate and water, and subsequently dried over sodium sulfate. The solvent is removed. The residue is subjected to reaction with Cbz-glycine aldehyde, or another Cbz-amino aldehyde derived from the corresponding amino acid, under the conditions described for the synthesis of 4-3 to give 8-3, and the resulting compound is purified by silica gel column.

Compound 8-3 is dissolved in THF in the presence of sodium bicarbonate and di-t-butyl dicarbonate (1.2 equiv). After removal of solvent and purification by a silica gel column the product is treated overnight with hydrogen in the presence of catalytic amounts of palladium on carbon in methanol. The solid is removed by filtration and solvent is removed to give 8-4, which is used for the next step reaction.

Compound 8-5 is synthesized by the method described for compound 3-5, with subsequent protecting with a Cbz group by treatment with Cbz-OSu as described for compound 3-6 and 4-6.

Compound 8-6 is synthesized by the method described for compound 2-3.

Compound 8-6 and methyl(triphenylphosphoranylidene) acetate (2 equiv) in methylene chloride is stirred for 16 hours. The solvent is evaporated and the residue purified on a silica gel column to give a compound mainly with (E)-olefin. This compound is subsequently subjected to treatment with hydrogen and catalytic amounts of Pd on carbon (10%) in EtOAc for 10 hours. After filtration and evaporation of solvent, compound 8-7 is obtained for use in the next step reaction without further purification.

Compound 8-8 is synthesized by the method described for compound 2-6.

Compound 8-8 is treated with aqueous sodium hydroxide (1.1 equiv) in methanol for 6 hours. The solution is neutralized with hydrochloric acid and solvent is evaporated. The residue is dissolved in THF and NMM (1 equiv) is added. To the solution is added slowly a THF solution of IBCF (1 equiv) at 15° C. The mixture is stirred at this temperature for an additional 30 minutes. A solution of sodium borohydride (1.5 equiv) in water is added in portions to the THF solution. After 20 minutes, the temperature is raised to room temperature and stirred for an 1 hour. The organic solvent is evaporated and the residue is purified on a column to give 8-9.

Compound 8-9 is treated with 30% TFA in methylene chloride for one hour. The solvent is then removed. The residue is dissolved in EtOAc and washed by aqueous sodium carbonate and water, and subsequently dried over sodium sulfate. After removal of solvent the resulting compound undergoes a reaction as described in the method of synthesis of compound 2-1 to give compound 8-10. Compound 8-10 is synthesized by the method described for compound 4-7. Treatment with 30% TFA in methylene chloride for one hour with subsequent purification by HPLC gives the final product 8-11.

Scheme 9: Synthesis of tetra-substituted piperazine compounds

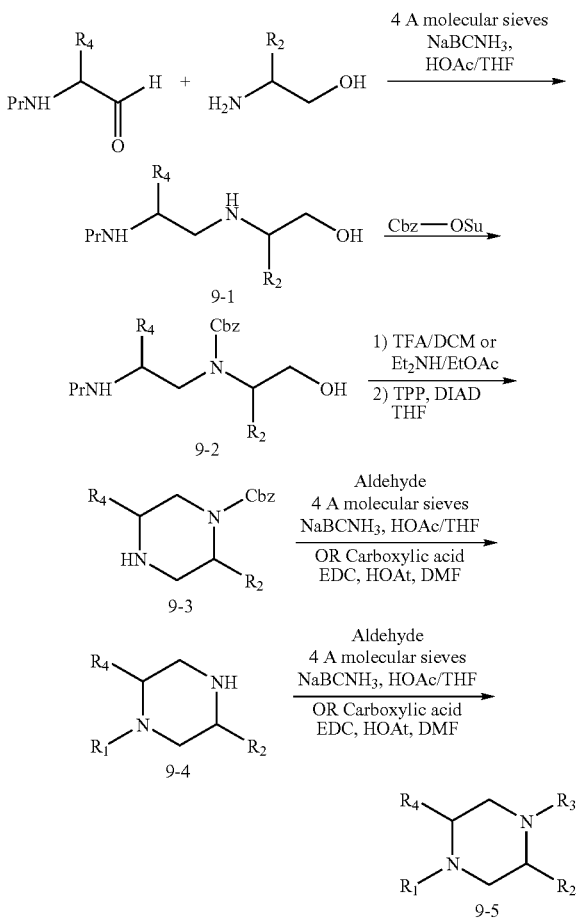

Compound 9-1 is synthesized by the method as described for compound 2-4.

Compound 9-2 is synthesized by the method as described for compound 4-6.

Compound 9-3 is synthesized by the method as described for compound 2-5.

Compound 9-4 and 9-5 are synthesized by the method as described for compound 2-6 or 2-7.

Compounds Resulting From Synthetic Schemes. It may thus be seen that Scheme 2, for example, results in a tetra-substituted compound of the following general structure:

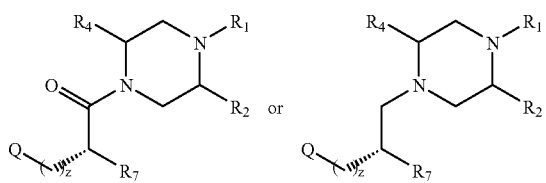

where $R_1$, $R_2$, $R_4$, $R_7$, Q and z are as defined above. $R_1$ may be any group as defined by -L-J, including groups such as those where L is —$(CH_2)_q$—, —$(CH_2)_q$—O—, —$(CH_2)_q$—O—(C=O)—, —$(CH_2)_q$—NH—, —$(CH_2)_q$—NH—(C=O)—, —$(CH_2)_q$—(C=O)—NH—, —$(CH_2)_q$—, (C=O)—O—, —NH—(C=O)—$(CH_2)_q$—, —(C=O)—NH—$(CH_2)_q$—, —NH—$(CH_2)_q$—, —NH—$(CH_2)_q$—O—, —(C=O)$(CH_2)_q$—, —$(CH_2)_q$—(C=O)— or —(C=O)—O—$(CH_2)_q$—, where q is from 0 to 6, and where J is

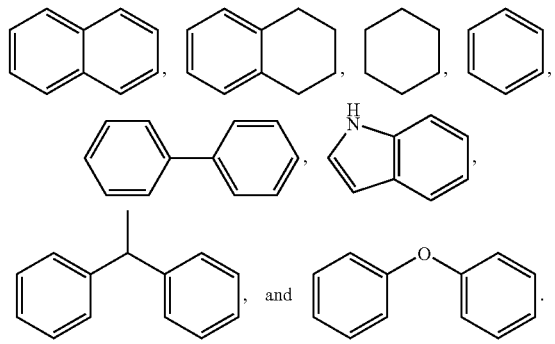

In the foregoing, at least one ring of J can be substituted at one or more positions with one or more substituents, such as hydroxyl, halogen, alkyl or aryl groups.

$R_2$ is —$(CH_2)_y$—W; particularly preferred are compounds where $R_2$ is

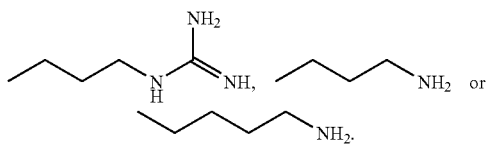

$R_4$ may be a $C_1$ to $C_6$ can be a linear or branched chain, including methyl, dimethyl, isopropyl or isobutyl. Alternatively, $R_4$ may be

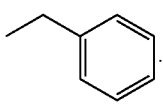

Scheme 2 can be efficiently used for the synthesis of compounds, such as compounds described generally in the examples. Structures without an $R_4$ group may be synthesized using an N-protected glycine at step 2-2. Structures with an $R_4$ group may be synthesized using an N-protected amino acid at step 2-2 with its side chain forming $R_4$.

It is evident from Scheme 2 that by using an alpha-alpha di-substituted amino acid, compounds with two $R_4$ groups at one carbon atom of the piperazine ring can also be synthesized.

Scheme 3 can be efficiently used for the synthesis of compounds with both an $R_4$ and $R_5$ group. The introduction of desired $R_4$ and $R_5$ groups is achieved by the use of an appropriately substituted amino alcohol in making 3-4. This methodology affords compounds with $R_2$ containing an amine function (compound 3-9) which can further be modified to derivatize the amino function as guanidine (compound 3-10), or through alkylation or acylation of the amine function can be used to synthesize compounds with hydrogen bonding potential.

Schemes 4, 5, 6 and 7 are versatile for the synthesis of compounds of the invention. These schemes also allows introduction of a variety of chiral $R_4$ groups by use of corresponding amino acid esters. This includes aliphatic as well as dibasic amino acids, among others. The $R_2$ from these schemes can also be obtained as a hydrogen bonding neutral group containing an —OH function (compounds 3-6 and 5-2) which can be processed directly to introduced $R_1$ and $R_3$ groups.

Scheme 8 allows introduction of a variety of chiral $R_5$ groups using corresponding amino acid derivatives. Among others, this includes aliphatic as well as dibasic amino acids. The $R_2$ from this scheme can also be obtained as a hydrogen bonding neutral group containing an ester, OH, or guanidine function (i.e., compounds 8-8, 8-9, and 8-10, respectively, which can be processed directly to introduced $R_1$ and $R_3$ groups).

Assays and Tests Employed in the Invention.

Competitive inhibition assay. A competitive inhibition binding assay was conducted using membranes prepared from hMC1-R or B-16 mouse melanoma cells (containing MC1-R), hMC3-R, hMC4-R, and hMC5-R, and using 0.4 nM $^{125}$I-NDP-α-MSH (New England Nuclear, Boston, Mass., USA) in 50 mM HEPES buffer containing 1 mM $MgCl_2$, 2 mM $CaCl_2$, and 5 mM KCl, at pH 7.2. The assay tube also contained a chosen concentration of the test compound of this invention, typically a 1 μM concentration, for determining its efficacy in inhibiting the binding of $^{125}$I-NDP-α-MSH to its receptor. Non-specific binding was measured by complete inhibition of binding of $^{125}$I-NDP-α-MSH in the assay with the presence of 1 μM α-MSH.

Incubation was for 90 minutes at room temperature, after which the assay mixture was filtered and the membranes washed three times with ice cold buffer. The filter was dried and counted in a gamma counter for remaining radioactivity bound to the membranes. 100% specific binding was defined as the difference in radioactivity (cpm) bound to cell membranes in the absence and presence of 1 μM α-MSH. The cpm obtained in the presence of test compounds are normalized with respect to 100% specific binding to determine the percent inhibition of $^{125}$I-NDP-α-MSH binding. Each assay was conducted in triplicate and the actual mean values are described, with results less than 0% reported as 0%.

$EC_{50}$ determination in functional activity assay. The Ki (nM) of certain compounds of the invention was determined. Functional evaluation of compounds at melanocortin receptors is performed by measuring the accumulation of intracellular cAMP in HEK-293 cells expressing MC3-R, MC4-R or MC5-R, and in B-16 mouse melanoma cells (containing MC1-R). Cells, suspended in Earle's Balanced Salt Solution containing 10 mM HEPES, pH 7.5, 5 mM $MgCl_2$, 1 mM glutamine, 0.1% albumin and 0.6 mM 3-isobutyl-1-methylxanthine, a phosphodiesterase inhibitor, were plated in 96 well plates at a density of $0.5 \times 10^5$ cells per well. Cells were incubated with the test compounds in the presence or absence of α-MSH for 1 hour at 37° C. cAMP levels were measured by EIA (Amersham) in the cell lysates. Data analysis and $EC_{50}$ values are determined using nonlinear regression analysis with Prism Graph-Pad software.

Functional status. The agonist/antagonist status with respect to MC1-4, MC4-R, and MC5-R of selected compounds of the invention was determined. Antagonistic activity was determined by measuring the inhibition of α-MSH-induced cAMP levels following exposure to the compounds as in the preceding descriptions.

Penile erection induction. The ability of compounds to induce penile erection (PE) in male rats is evaluated with selected compounds. Male Sprague-Dawley rats weighing 200-250 g are kept on a 12 hour on/off light cycle with food and water ad libitum. All behavioral studies are performed between 10 a.m. and 5 p.m. Groups of 4-8 rats are treated with compounds at a variety of doses via intravenous (IV) or intracerebroventricular (ICV) routes. Immediately after treatment, rats are placed into individual polystyrene cages (27 cm long, 16 cm wide, and 25 cm high) for behavioral observation. Rats are observed for 30 minutes IV or 90 minutes ICV, and the number of yawns, grooming bouts and PEs are recorded in 10-minute bins.

ICV food intake and body weight change. Change in food intake and body weight is evaluated with selected compounds. Male Sprague-Dawley rats weighing ~300 g at the beginning of the experiment are kept on a 12 hour on/off light cycle. Lights out is adjusted to 12:00 p.m. to allow for dosing just prior to the start of their dark period. Rats (8-12/group) are fed powdered chow and water ad libitum. For 1 week before treatment, 24-hour food intake and body weight change is recorded to assess a baseline for the group during vehicle treatment. The rats are dosed ICV with vehicle or selected compounds (1-3 nmol). The changes in body weight and food intake for the 24 hour period after dosing are determined. The changes in body weight and food intake for the 48 hour period, and in some cases for 72 hours as well, after dosing are also measured to determined reversal of changes in body weight and food intake effect back to baseline.

IV food intake and body weight change. Change in food intake and body weight is evaluated with selected compounds. Male Sprague-Dawley rats weighing ~300 g at the beginning of the experiment are kept on a 12 hour on/off light cycle. Lights out is adjusted to 12:00 p.m. to allow for dosing just prior to the start of their dark period. Rats (8-12/group) are fed powdered chow and water ad libitum. For 1 week before treatment, 24-hour food intake and body weight change is recorded to assess a baseline for the group during vehicle treatment. The rats are dosed IV with vehicle or selected compounds (0.5-3 mg/kg). The changes in body weight and food intake for the 24 hour period after dosing are determined. The changes in body weight and food intake for the 48 hour period, and in same cases for 72 hours as well, after dosing are also measured to determined reversal of changes in body weight and food intake effect back to baseline.

Determination of mass and nuclear magnetic resonance analysis. The mass values are determined using a Waters MicroMass ZQ device utilizing a positive mode. Mass determinations are compared with calculated values and expressed in the form of mass weight plus one (M+1).

Proton NMR data is obtained using a Bruker 300 MHz spectrometer. The spectra are obtained after dissolving compounds in a deuterated solvent such as chloroform, dimethyl sulfoxide, or methanol as appropriate.

Representative Compounds of the Invention

EXAMPLE 1

N-{3-[(S)-4-[(R)-2-Amino-3-(4-chloro-phenyl)-propionyl]-1-(2-naphthalen-2-yl-ethyl)-piperazin-2-yl]-propyl}-guanidine The following compound was synthesized by the method of Scheme 1 where $R_1$ was 2-naphthylacetic acid, Boc-$R_2$ was Fmoc-Orn(Boc)-OH to which a guanidine group was subsequently added, and Boc-$R_3$ was Boc-D-Phe(4-Cl)—OH. It was tested as described above with the results shown. The molecular weight (m+1) was 521.2.

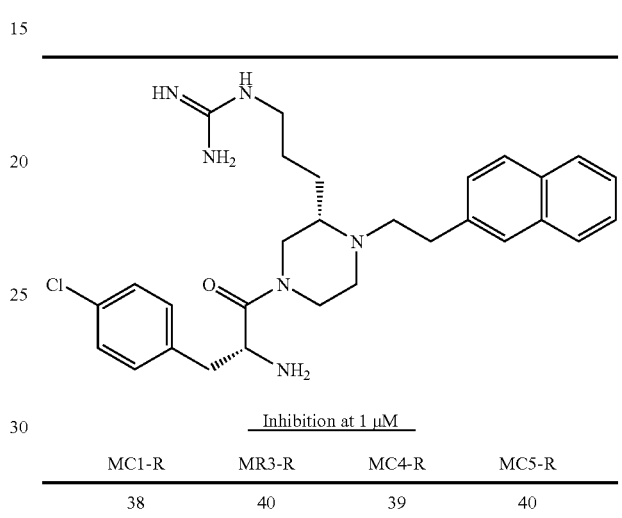

| Inhibition at 1 μM | | | |
|---|---|---|---|
| MC1-R | MR3-R | MC4-R | MC5-R |
| 38 | 40 | 39 | 40 |

EXAMPLE 2

N-(3-{(S)-4-[(R)-2-Amino-3-(4-chloro-phenyl)-propionyl]-1-benzyl-piperazin-2-yl}-propyl)-guanidine The following compound was synthesized by the method of Scheme 1 where $R_1$ was benzoic acid, Boc-$R_2$ was Fmoc-Orn(Boc)-OH to which a guanidine group was subsequently added and Boc-$R_3$ was Boc-D-Phe(4-Cl)—OH. It was tested as described above with the results shown. The molecular weight (m+1) was 471.3.

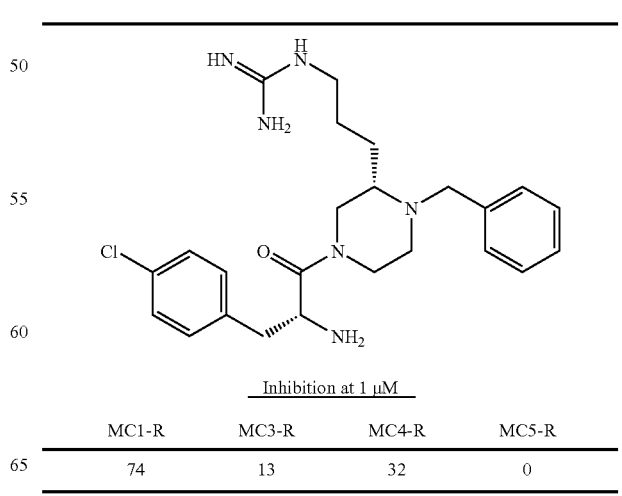

| Inhibition at 1 μM | | | |
|---|---|---|---|
| MC1-R | MC3-R | MC4-R | MC5-R |
| 74 | 13 | 32 | 0 |

EXAMPLE 3

N-(3-{(S)-4-[(R)-2-Amino-3-(4-chloro-phenyl)-propionyl]-1-phenethyl-piperazin-2-yl}-propyl)-guanidine The following compound was synthesized by the method of Scheme 1 where $R_1$ was naphthylacetic acid, Boc-$R_2$ was Fmoc-Orn(Boc)-OH to which a guanidine group was subsequently added and Boc-$R_3$ was Boc-D-Phe(4-Cl)—OH. It was tested as described above with the results shown. The molecular weight (m+1) was 457.4.

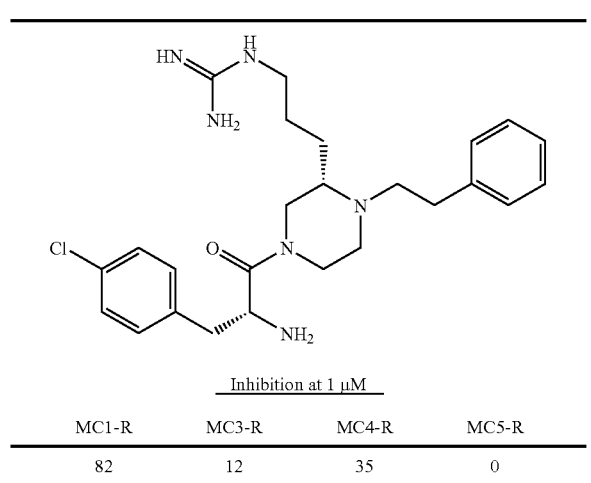

| Inhibition at 1 μM | | | |
|---|---|---|---|
| MC1-R | MC3-R | MC4-R | MC5-R |
| 82 | 12 | 35 | 0 |

EXAMPLE 4

N-{3-[(R)-4-[(R)-2-Amino-3-(4-chloro-phenyl)-propionyl]-1-(2-naphthalen-2-yl-ethyl)-piperazin-2-yl]-propyl}-guanidine The following compound was synthesized by the method of Scheme 1 where $R_1$ was 2-naphthylacetic acid, Boc-$R_2$ was Fmoc-Orn(Boc)-OH to which a guanidine group was subsequently added and Boc-$R_3$ was Boc-D-Phe(4-Cl)—OH. It was tested as described above with the results shown. The molecular weight (m+1) was 521.0.

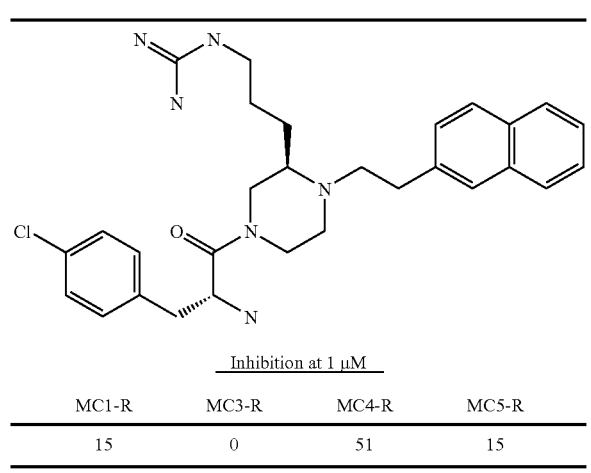

| Inhibition at 1 μM | | | |
|---|---|---|---|
| MC1-R | MC3-R | MC4-R | MC5-R |
| 15 | 0 | 51 | 15 |

EXAMPLE 5

N-(3-{(R)-4-[(R)-2-Amino-3-(4-chloro-phenyl)-propionyl]-1-phenethyl-piperazin-2-yl}-propyl)-guanidine The following compound was synthesized by the method of Scheme 1 where $R_1$ was naphthylacetic acid, Boc-$R_2$ was Fmoc-Orn(Boc)-OH to which a guanidine group was subsequently added and Boc-$R_3$ was Boc-D-Phe(4-Cl)—OH. It was tested as described above with the results shown. The molecular weight (m+1) was 470.9.

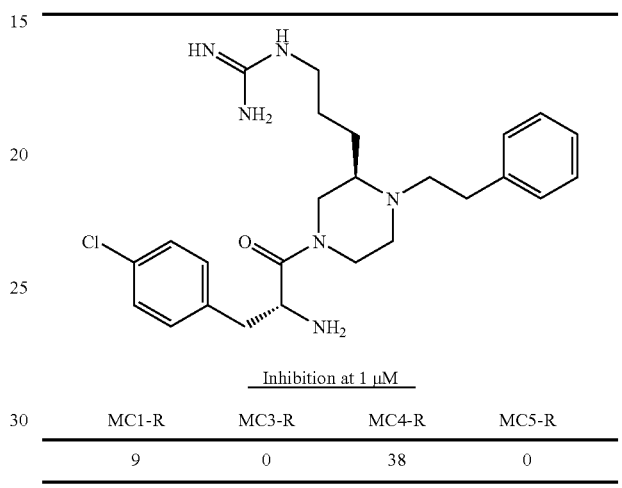

| Inhibition at 1 μM | | | |
|---|---|---|---|
| MC1-R | MC3-R | MC4-R | MC5-R |
| 9 | 0 | 38 | 0 |

EXAMPLE 6

N-(3-{(R)-4-[(R)-2-Amino-3-(4-chloro-phenyl)-propionyl]-1-benzyl-piperazin-2-yl}-propyl)-guanidine The following compound was synthesized by the method of Scheme 1 where $R_1$ was benzoic acid, Boc-$R_2$ was Fmoc-Orn(Boc)-OH to which a guanidine group was subsequently added and Boc-$R_3$ was Boc-D-Phe(4-Cl)—OH. It was tested as described above with the results shown. The molecular weight (m+1) was 456.9.

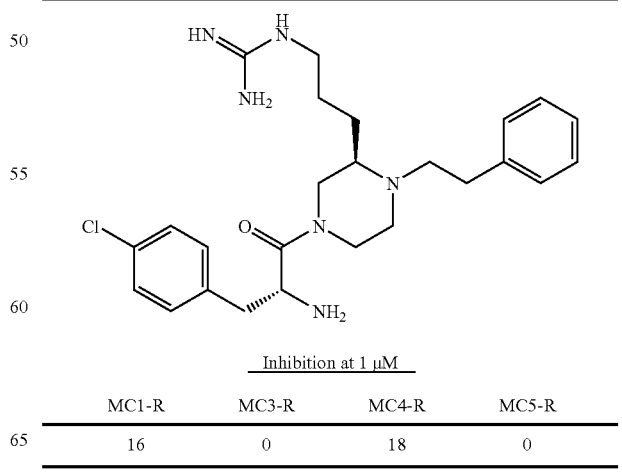

| Inhibition at 1 μM | | | |
|---|---|---|---|
| MC1-R | MC3-R | MC4-R | MC5-R |
| 16 | 0 | 18 | 0 |

EXAMPLE 7

(R)-2-Amino-1-[(R)-3-(3-amino-propyl)-4-(2-naphthalen-2-yl-ethyl)-piperazin-1-yl]-3-(4-chloro-phenyl)-propan-1-one The following compound was synthesized by the method of Scheme 1 where $R_1$ was 2-naphthylacetic acid, Boc-$R_2$ was Fmoc-D-Orn(Boc)-OH, and Boc-$R_3$ was Boc-D-Phe(4-Cl)—OH. Thus the synthetic scheme was as follows:

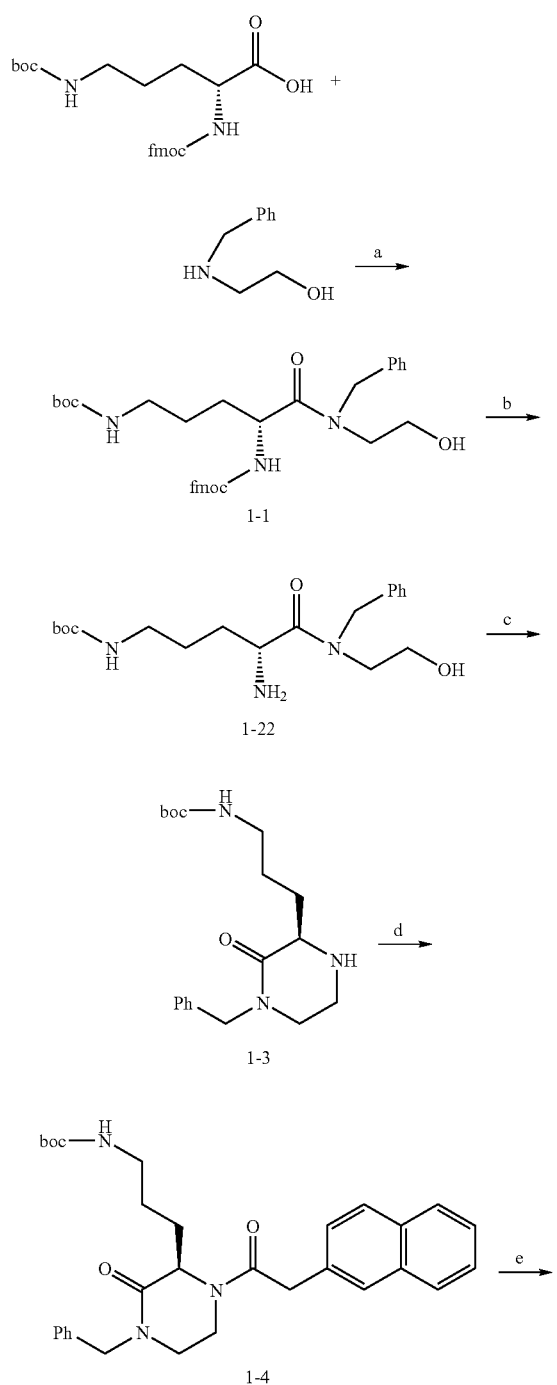
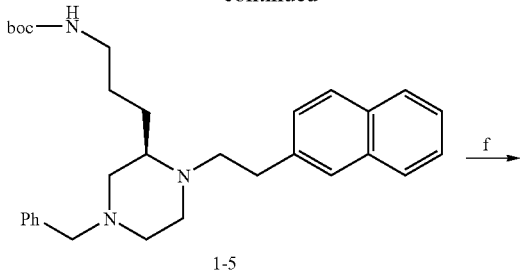
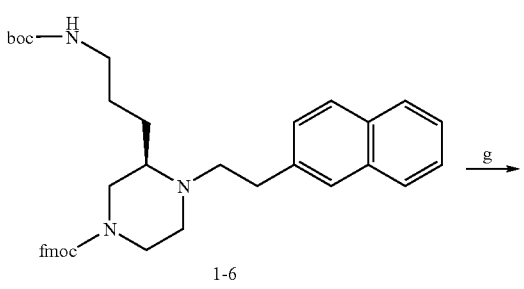
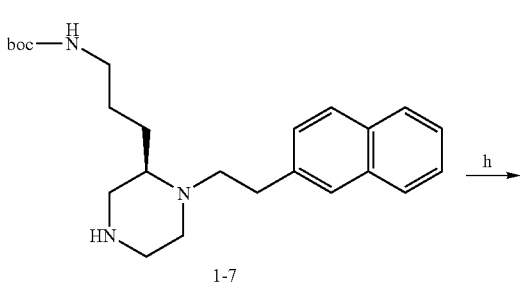
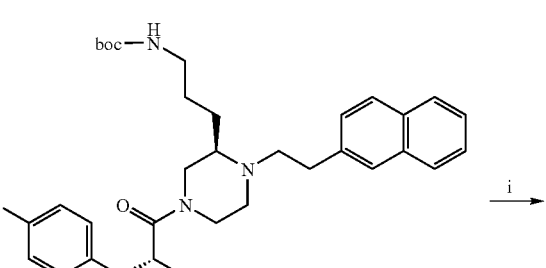
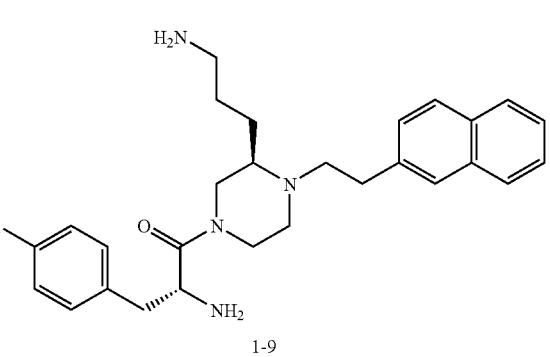

a) TBTU, NMM, EtOAc; b) 20% Et$_2$NH/EtOAc; c) Ph$_3$P, DIAD, EtOAc; d) Naphthylacetic acid, HOAt, EDC, NMM, DMF; e) AlH$_3$—TEA; f) Fmoc—Cl, CH$_3$CN; g) 20% Et$_2$NH/EtOAc; h) EDC, HOAt, DMF, NMM, Boc—D—Phe(4-Cl)—OH; i) TFA/DCM The compound was tested as described above with the results shown. The molecular weight (m+1) was 479.5.

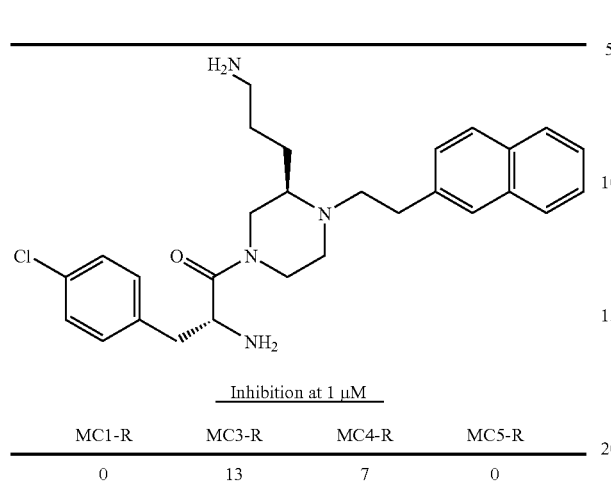

| Inhibition at 1 μM | | | |
|---|---|---|---|
| MC1-R | MC3-R | MC4-R | MC5-R |
| 0 | 13 | 7 | 0 |

EXAMPLE 8

(R)-2-Amino-1-[(R)-3-(4-amino-butyl)-4-(2-naphthalen-2-yl-ethyl)-piperazin-1-yl]-3-(4-chloro-phenyl)-propan-1-one The following compound was synthesized by the method of Scheme 1 where $R_1$ was 2-naphthylacetic acid, Boc-$R_2$ was Fmoc-D-Lys(Boc)-OH, and Boc-$R_3$ was Boc-D-Phe(4-Cl)—OH. It was tested as described above with the results shown. The molecular weight (m+1) was 493.4.

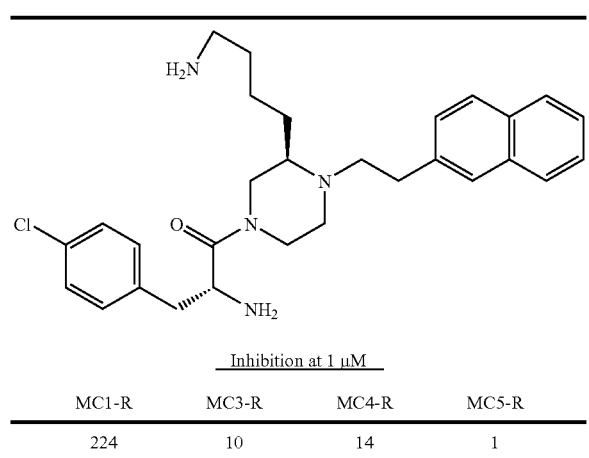

| Inhibition at 1 μM | | | |
|---|---|---|---|
| MC1-R | MC3-R | MC4-R | MC5-R |
| 224 | 10 | 14 | 1 |

EXAMPLE 9

(R)-2-Amino-1-[(R)-3-(2-amino-ethyl)-4-(2-naphthalen-2-yl-ethyl)-piperazin-1-yl]-3-(4-chloro-phenyl)-propan-1-one The following compound was synthesized by the method of Scheme 1 where $R_1$ was 2-naphthylacetic acid, Boc-$R_2$ was Fmoc-D-Dab(Boc)-OH (N-alpha-Fmoc—N-gamma-Boc-D-diaminobutanoic acid), and Boc-$R_3$ was Boc-D-Phe(4-Cl)—OH. It was tested as described above with the results shown. The molecular weight (m+1) was 465.2.

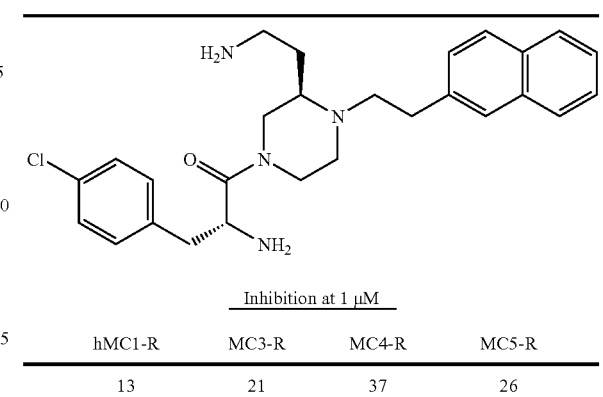

| Inhibition at 1 μM | | | |
|---|---|---|---|
| hMC1-R | MC3-R | MC4-R | MC5-R |
| 13 | 21 | 37 | 26 |

EXAMPLE 10

(R)-2-Amino-1-[(R)-3-aminomethyl-4-(2-naphthalen-2-yl-ethyl)-piperazin-1-yl]-3-(4-chloro-phenyl)-propan-1-one The following compound was synthesized by the method of Scheme 1 where Scheme 1 where $R_1$ was 2-naphthylacetic acid, Boc-$R_2$ was Fmoc-D-Dpr(Boc)-OH (N-alpha-Fmoc-N-beta-Boc-D-diaminopropionic acid), and Boc-$R_3$ was Boc-D-Phe(4-Cl)—OH. It was tested as described above with the results shown. The molecular weight (m+1) was 451.2.

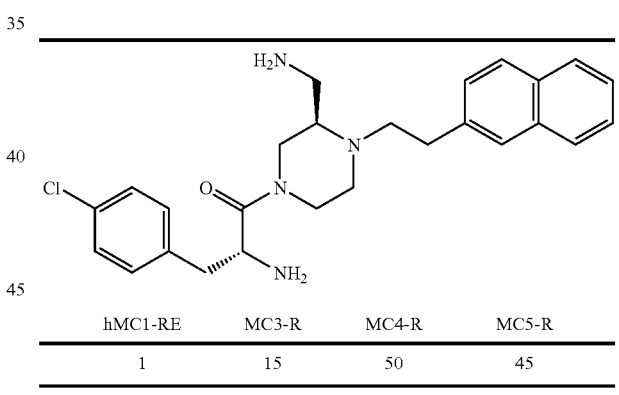

| hMC1-RE | MC3-R | MC4-R | MC5-R |
|---|---|---|---|
| 1 | 15 | 50 | 45 |

EXAMPLE 11

The compounds of Table 1 where $R_4$ is H are synthesized by the method of any of Schemes 1 through 8. This is achieved by using an appropriate starting material that yields H as $R_4$. For example, in Scheme 2, 2-2 is glycine, in Scheme 3 compound 2-1 is N-benzyl-1-amino ethanol, in Schemes 3 and 4 glycine methyl ester is reacted with 4-2 to give 4-3, in Scheme 6 Fmoc-amino ethanol is reacted with Orn(Boc)-OMe to give 6-1, and in Scheme 7 Fmoc-glycine is used to prepare 7-1. The $R_1$ group is introduced using 3-beta-naphthalene propionic acid or 2-beta-naphthalene ethyl bromide as described. All the compounds are prepared using an appropriate (QCH$_2$)CHR$_7$COOH reactant to yield the listed $R_3$ groups. The compounds are tested as described above.

The compounds all have the following general structure:

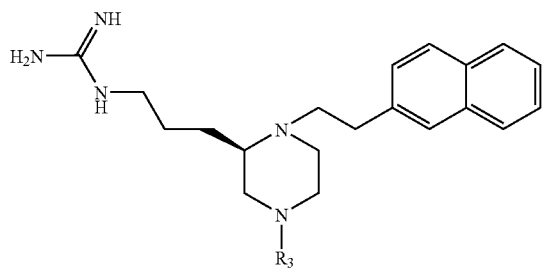

with $R_3$ as shown in Table 1.

TABLE 1

| No. | $R_3$ |
|-----|-------|
| 1-1 | benzyl-CH(NH$_2$)-C(O)-CH$_3$ |
| 1-2 | 4-methylbenzyl-CH(NH$_2$)-C(O)-CH$_3$ |
| 1-3 | 4-methoxybenzyl-CH(NH$_2$)-C(O)-CH$_3$ |
| 1-4 | 4-chlorobenzyl-CH(N(CH$_3$)$_2$)-C(O)-CH$_3$ |
| 1-5 | 4-chlorobenzyl-CH(NHCH$_3$)-C(O)-CH$_3$ |
| 1-6 | 4-chlorobenzyl-CH(N(CH$_2$CH$_3$)$_2$)-C(O)-CH$_3$ |
| 1-7 | 4-chlorobenzyl-CH(NH-CH(CH$_3$)$_2$)-C(O)-CH$_3$ |

EXAMPLE 12

The compounds of Table 2 where $R_4$ is H are synthesized by the method of any of Schemes 1 through 8. This is achieved by using an appropriate starting material that yields H as $R_4$. For example, in Scheme 2, 2-2 is glycine, in Scheme 3 compound 2-1 is N-benzyl-1-amino ethanol, in Schemes 3 and 4 glycine methyl ester is reacted with 4-2 to give 4-3, in Scheme 6 Fmoc-amino ethanol is reacted with Orn(Boc)-OMe to give 6-1, and in Scheme 7 Fmoc-glycine is used to prepare 7-1. The $R_1$ group is introduced using 3-indole propionic acid or 2-indole ethyl bromide as described. All the compounds are prepared using an appropriate (QCH$_2$)CHR$_7$COOH reactant to yield the listed $R_3$ groups. The compounds are tested as described above.

The compounds all have the following general structure:

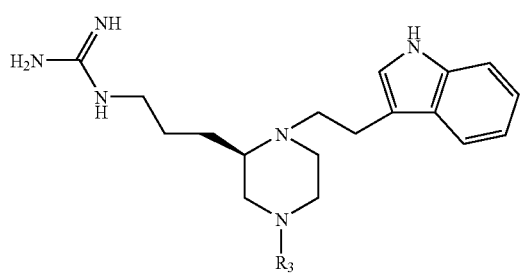

with $R_3$ as shown in Table 2.

TABLE 2

| No. | $R_3$ |
|-----|-------|
| 2-1 | benzyl-CH(NH$_2$)-C(O)-CH$_3$ |
| 2-2 | 4-methylbenzyl-CH(NH$_2$)-C(O)-CH$_3$ |
| 2-3 | 4-methoxybenzyl-CH(NH$_2$)-C(O)-CH$_3$ |
| 2-4 | 4-chlorobenzyl-CH(N(CH$_3$)$_2$)-C(O)-CH$_3$ |
| 2-5 | 4-chlorobenzyl-CH(NHCH$_3$)-C(O)-CH$_3$ |
| 2-6 | 4-chlorobenzyl-CH(N(CH$_2$CH$_3$)$_2$)-C(O)-CH$_3$ |

TABLE 2-continued

| No. | R₃ |
|---|---|
| 2-7 | (4-Cl-benzyl, C(=O)CH₃, NH-CH(CH₃)₂) |

EXAMPLE 13

The compounds of Table 3 where $R_4$ is H are synthesized by the method of any of Schemes 6 or 7. This is achieved by using an appropriate starting material that yields H as $R_4$. For example, in Scheme 6 Fmoc-amino ethanol is reacted with Orn(Boc)-OMe to give 6-1, and in Scheme 7 Fmoc-glycine is used to prepare 7-1. The $R_1$ group is introduced using 3-phenyl-propionic acid as described. All the compounds are prepared using appropriate (QCH₂)CHR₇COOH reactant to yield the listed $R_3$ groups. The compounds are tested as described above.

The compounds all have the following general structure:

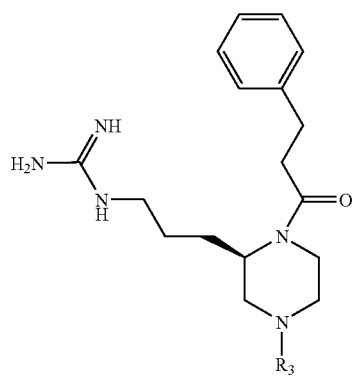

with $R_3$ as shown in Table 3.

TABLE 3

| No. | R₃ |
|---|---|
| 3-1 | (benzyl, C(=O)CH₃, NH₂) |
| 3-2 | (4-CH₃-benzyl, C(=O)CH₃, NH₂) |
| 3-3 | (4-CH₃O-benzyl, C(=O)CH₃, NH₂) |

TABLE 3-continued

| No. | R₃ |
|---|---|
| 3-4 | (4-Cl-benzyl, C(=O)CH₃, N(CH₃)₂) |
| 3-5 | (4-Cl-benzyl, C(=O)CH₃, NHCH₃) |
| 3-6 | (4-Cl-benzyl, C(=O)CH₃, N(CH₂CH₃)₂) |
| 3-7 | (4-Cl-benzyl, C(=O)CH₃, NH-CH(CH₃)₂) |

EXAMPLE 14

The compounds of Table 4 where $R_4$ is $CH_3$ are synthesized by the methods of Schemes 6 or 7. This is achieved by using the appropriate starting material that yields $CH_3$ as $R_4$. For example, in Scheme 6 Fmoc-alaninol is reacted with Orn(Boc)-OMe to give 6-1, and in Scheme 7 Fmoc-alanine is used to prepare 7-1. The $R_1$ group is introduced using 3-phenyl-propionic acid as described. All the compounds are prepared using an appropriate (QCH₂)CHR₇COOH reactant to yield the listed $R_3$ groups. The compounds are tested as described above.

The compounds all have the following general structure:

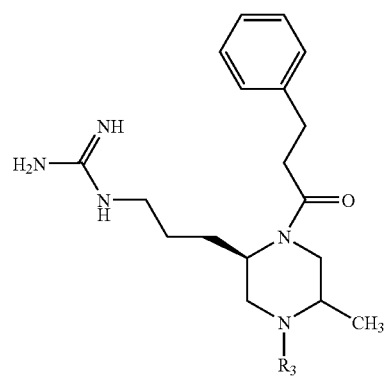

with $R_3$ as shown in Table 4.

TABLE 4

| No. | R₃ |
|---|---|
| 4-1 | (S)-2-amino-1-oxo-3-phenylpropyl |
| 4-2 | (S)-2-amino-3-(4-methylphenyl)-1-oxopropyl |
| 4-3 | (S)-2-amino-3-(4-methoxyphenyl)-1-oxopropyl |
| 4-4 | (S)-3-(4-chlorophenyl)-2-(dimethylamino)-1-oxopropyl |
| 4-5 | (S)-3-(4-chlorophenyl)-2-(methylamino)-1-oxopropyl |
| 4-6 | (S)-3-(4-chlorophenyl)-2-(diethylamino)-1-oxopropyl |
| 4-7 | (S)-3-(4-chlorophenyl)-2-(isopropylamino)-1-oxopropyl |

EXAMPLE 15

The compounds of Table 5 where $R_4$ is $CH_3$ and $R_5$ is $CH-(CH_3)_2$ are synthesized by the method of Scheme 8. This is achieved by using the appropriate starting materials that yield $CH_3$ as $R_4$ and $CH-(CH_3)_2$ as $R_5$. For example, in Scheme 8, the compound 8-1 is a threonine derivative and Cbz-valine-aldehyde is used to react with 8-2. The $R_1$ is introduced using 3-phenyl-propionic acid as described (steps 8-9 to 8-10). Furthermore, all the compounds are prepared using an appropriate $(QCH_2)CHR_7COOH$ reactant to yield the listed $R_3$ groups (step 8-7 to 8-8). The compounds are tested as described above.

The compounds all have the following general structure:

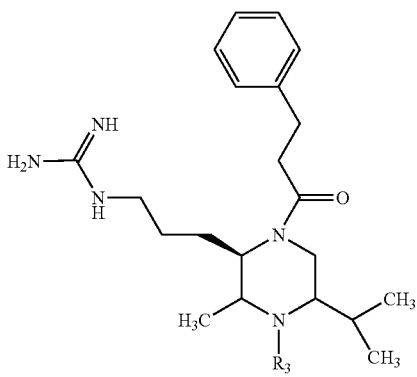

with $R_3$ as shown in Table 5.

TABLE 5

| No. | R₃ |
|---|---|
| 5-1 | (S)-2-amino-1-oxo-3-phenylpropyl |
| 5-2 | (S)-2-amino-3-(4-methylphenyl)-1-oxopropyl |
| 5-3 | (S)-2-amino-3-(4-methoxyphenyl)-1-oxopropyl |
| 5-4 | (S)-3-(4-chlorophenyl)-2-(dimethylamino)-1-oxopropyl |
| 5-5 | (S)-3-(4-chlorophenyl)-2-(methylamino)-1-oxopropyl |
| 5-6 | (S)-3-(4-chlorophenyl)-2-(diethylamino)-1-oxopropyl |
| 5-7 | (S)-3-(4-chlorophenyl)-2-(isopropylamino)-1-oxopropyl |

EXAMPLE 16

The compounds of Example 16 are synthesized by the methods of Scheme 9. The $R_1$ group is introduced using 2-naphthylacetaldehyde, which results from the oxidation of 2-naphthylethanol by Dess-martin periodinane as described in the synthesis of aminoaldehyde derivatives. The $R_2$ group is introduced by using an amino aldehyde derived from Fmoc-Arg(Boc)$_2$-OH. The $R_3$ groups are introduced by reductive amination with N-protected amino aldehydes. The compounds are tested as described above.

The compounds all have the following general structure:

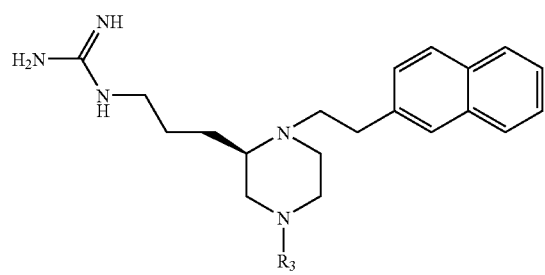

with $R_3$ as shown in Table 6.

TABLE 6

| No. | $R_3$ |
|---|---|
| 6-1 | |
| 6-2 | |
| 6-3 | |
| 6-4 | |
| 6-5 | |
| 6-6 | |

TABLE 6-continued

| No. | $R_3$ |
|---|---|
| 6-7 | |

EXAMPLE 17

The compounds of Example 17 are synthesized by the general methods of Scheme 9. The $R_1$ group is introduced using 2-naphthylacetic acid as described. The $R_2$ group is introduced by using an amino aldehyde derived from Fmoc-Arg(Boc)$_2$-OH. The $R_3$ groups are introduced by reductive amination with N-protected amino aldehydes. The compounds are tested as described above.

The compounds all have the following general structure:

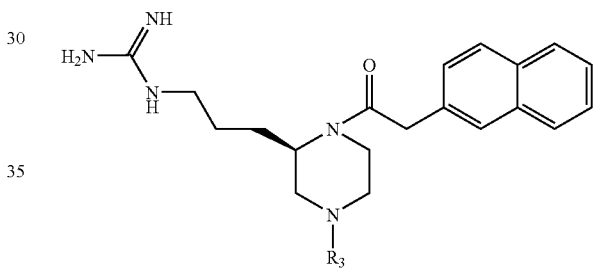

with $R_3$ as shown in Table 7.

TABLE 7

| No. | $R_3$ |
|---|---|
| 7-1 | |
| 7-2 | |
| 7-3 | |
| 7-4 | |

TABLE 7-continued

| No. | R₃ |
|---|---|
| 7-5 | 4-chlorobenzyl with C(=O)- and NHCH₃ substituent |
| 7-6 | 4-chlorobenzyl with C(=O)- and N(CH₂CH₃)₂ substituent |
| 7-7 | 4-chlorobenzyl with C(=O)- and NH-isopropyl substituent |

EXAMPLE 18

The compounds of Example 18 are synthesized by the methods of Scheme 9. The $R_1$ group is introduced using 2-naphthylacetaldehyde, which is from the oxidation of 2-naphthylethanol by Dess-martin periodinane as described in the synthesis of aminoaldehyde derivatives. The $R_2$ group is introduced by using an amino aldehyde derived from Fmoc-Arg(Boc)₂-OH. The $R_4$ group is introduced by using leucine amino alcohol. The $R_3$ groups are introduced by reductive amination with N-protected amino aldehydes. The compounds are tested as described above.

The compounds all have the following general structure:

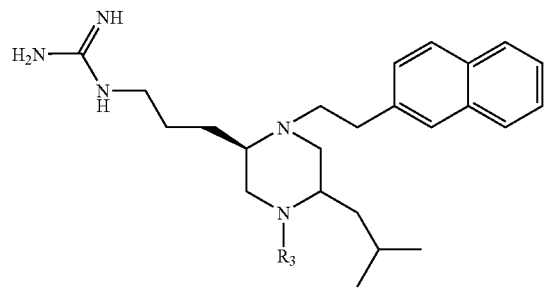

with $R_3$ as shown in Table 8.

TABLE 8

| No. | R₃ |
|---|---|
| 8-1 | benzyl with C(=O)- and NH₂ substituent |
| 8-2 | 4-methylbenzyl with C(=O)- and NH₂ substituent |
| 8-3 | 4-methoxybenzyl with C(=O)- and NH₂ substituent |
| 8-4 | 4-chlorobenzyl with C(=O)- and N(CH₃)₂ substituent |
| 8-5 | 4-chlorobenzyl with C(=O)- and NHCH₃ substituent |
| 8-6 | 4-chlorobenzyl with C(=O)- and N(CH₂CH₃)₂ substituent |
| 8-7 | 4-chlorobenzyl with C(=O)- and NH-isopropyl substituent |

EXAMPLE 19

The compounds of Example 19 are synthesized by the general methods of Scheme 9. The $R_1$ group is introduced using 2-naphthylacetic acid as described. The $R_2$ group is introduced by using an amino aldehyde derived from Fmoc-Arg(Boc)₂-OH. The $R_4$ group is introduced by using leucine amino alcohol. The $R_3$ groups are introduced by reductive amination with N-protected amino aldehydes.

The compounds all have the following general structure:

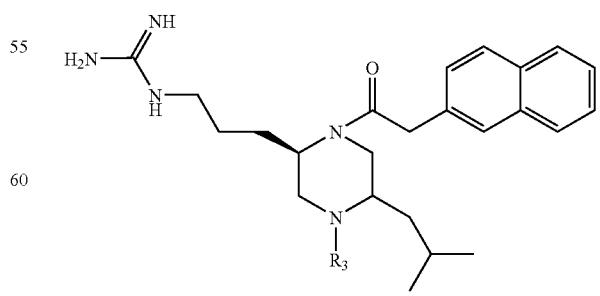

with $R_3$ as shown in Table 9.

TABLE 9

| No. | R₃ |
|---|---|
| 9-1 | 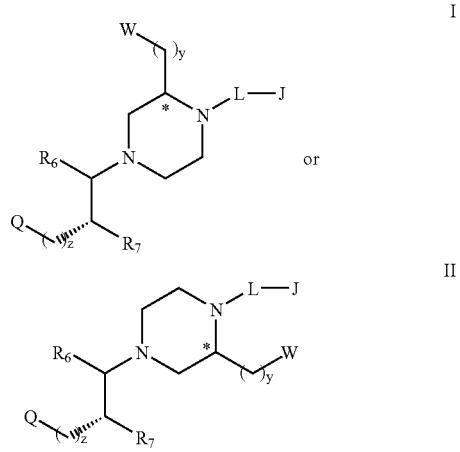 |
| 9-2 | |
| 9-3 | |
| 9-4 | |
| 9-5 | |
| 9-6 | |
| 9-7 | |

The preceding examples can be repeated with similar success by substituting the generically or specifically described reactants and/or synthetic conditions of this invention for those used in the preceding examples.

Although the invention has been described in detail with particular reference to these preferred embodiments, other embodiments can achieve the same results. Variations and modifications of the present invention will be obvious to those skilled in the art and it is intended to cover all such modifications and equivalents. The entire disclosures of all references, applications, patents, and publications cited above, and of the corresponding application(s), are hereby incorporated by reference.

What is claimed is:

1. A compound of formula I or II:

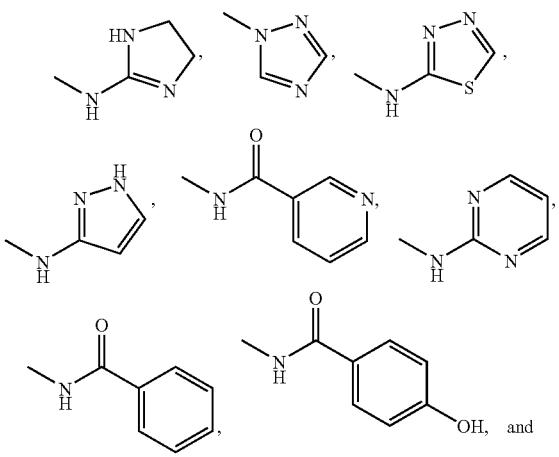

and pharmaceutically acceptable salts thereof;
wherein
J is a substituted or unsubstituted monocyclic or bicyclic ring structure, wherein in each instance the ring or rings have 5 or 6 ring atoms;
L is a linker selected from the group consisting of —(CH$_2$)$_q$—, —(CH$_2$)$_q$—O—, —(CH$_2$)$_q$—O—(C═O)—, —(CH$_2$)$_q$—NH—, —(CH$_2$)$_q$—NH—(C═O)—, —(CH$_2$)$_q$—(C═O)—NH—, —(CH$_2$)$_q$—(C═O)—O—, —NH—(C═O)—(CH$_2$)$_q$—, —(C═O)—NH—(CH$_2$)$_q$—, —NH—(CH$_2$)$_q$—, —NH—(CH$_2$)$_q$—O—, —(C═O)(CH$_2$)$_q$—, —(CH$_2$)$_q$—(C═O)—and —(C═O)—O—(CH$_2$)$_q$—,
q is from 0 to 6;
W is a heteroatom unit with at least one cationic center, hydrogen bond donor or hydrogen bond acceptor selected from the group consisting of NH$_2$, NH(C═NH)NH$_2$, —NHCOCH$_3$, —CONHCH$_3$, —NH(C═NH)NHMe, —NH(C═NH)NHEt, —NH(C═NH)NHPr, —NH(C═NH)NHPr—I, —NH(C═NH)NH$_2$, —NH(C═O)OCH$_3$, —NH(C═O)CH$_3$, —NH(C═O)NH$_2$, —NH(C═O)NHCH$_3$,

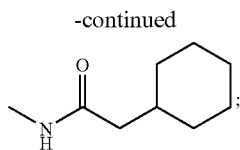

Q represents a substituted or unsubstituted aromatic carbocyclic ring;

$R_6$ is H, =O, =S or $CH_3$;

$R_7$ is $NH_2$, NH—$R_8$, or

$R_8$ is a $C_1$ to $C_6$ linear or branched chain or an amine capping group, and where there are two $R_8$ groups, each $R_8$ is independently a $C_1$ to $C_6$ linear or branched chain or an amine capping group, wherein the amine capping group is allyl, cyclopropane methyl, hexanoyl, heptanoyl, acetyl, propionoyl, butanoyl, phenylacetyl, cyclohexylacetyl, naphthylacetyl, cinnamoyl, phenyl, benzyl, benzoyl, 12-Ado, 7'-amino heptanoyl, 6-Ahx, Amc, 8-Aoc or polyethylene glycol with a formula molecular weight of between about 100 and about 10,000;

y is from 0 to 6;

z is from 0 to 6; and wherein the carbon atom marked with an asterisk can have any stereochemical configuration.

2. The compound of claim 1 wherein $R_6$ is H or =O.

3. The compound of claim 1 wherein $R_7$ is NH2, $N(CH_3)_2$, $NHCH_3$,

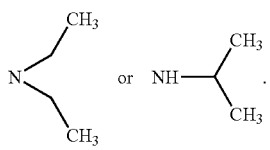

4. The compound of claim 1 wherein L is —$CH_2$—, —$(CH_2)_2$—, or —(C=O)$(CH_2)_2$—.

5. The compound of claim 1 wherein J is a substituted or unsubstituted ring structure selected from the group consisting of:

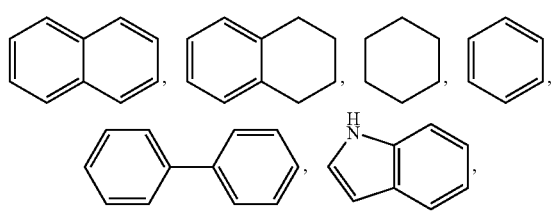

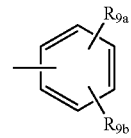

6. The compound of claim 5 wherein J is substituted at one or more positions with one or more hydroxyl, halogen, alkyl or aryl groups.

7. The compound of claim 1 wherein W is selected from the group consisting of $NH_2$ and NH(C=NH)$NH_2$.

8. The compound of claim 1 wherein Q is phenyl, substituted phenyl, naphthyl or substituted naphthyl.

9. The compound of claim 1 wherein Q is an indole, substituted indole, quinoline, substituted quinoline, isoquinoline or substituted isoquinoline.

10. The compound of claim 1 wherein Q is:

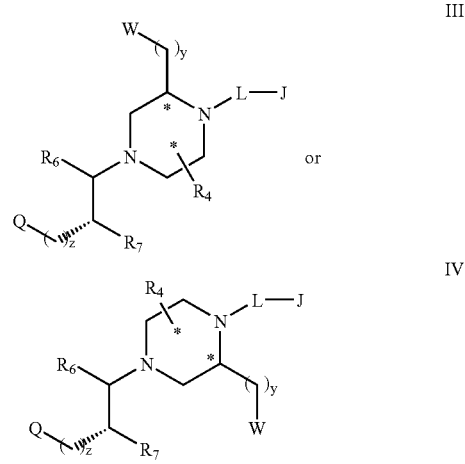

wherein $R_{9a}$ and $R_{9b}$ are optional ring substituents, and when one or both are present, are the same or different and independently hydroxyl, halogen, alkyl, or aryl groups attached directly or through an ether linkage.

11. A compound of formula III or IV:

and pharmaceutically acceptable salts thereof
wherein
J is a substituted or unsubstituted monocyclic or bicyclic ring structure, wherein in each instance the ring or rings have 5 or 6 ring atoms;
L is a linker selected from the group consisting of —($CH_2)_q$—, —$(CH_2)_q$—O—, —$(CH_2)_q$—O—(C=O)—, —$(CH_2)_q$—NH—, —$(CH_2)_q$—NH—(C=O)—, —$CH_2)_q$—(C=O)—NH—, —$CH_2)_q$—(C=O)—O—, —NH—(C=O)—$(CH_2)_q$, —(C=O)—NH—$(CH_2)_q$, —NH—$(CH_2)_q$—, —NH—$(CH_2)_q$—O—, —(C=O)$(CH_2)_q$—, —$CH_2)_q$—(C=O)— and —(C=O)—O—$(CH_2)_q$— q is from 0 to 6;

W is a heteroatom unit with at least one cationic center, hydrogen bond donor or hydrogen bond acceptor selected from the group consisting of $NH_2$, $NH(C=NH)NH_2$, $-NHCOCH_3$, $-CONHCH_3$, $-NH(C=NH)NHMe$, $-NH(C=NH)NHEt$, $-NH(C=NH)NHPr$, $-NH(C=NH)NHPr-I$, $-NH(C=NH)NH_2$, $-NH(C=O)OCH_3$, $-NH(C=O)CH_3$, $-NH(C=O)NH_2$, $-NH(C=O)NHCH_3$,

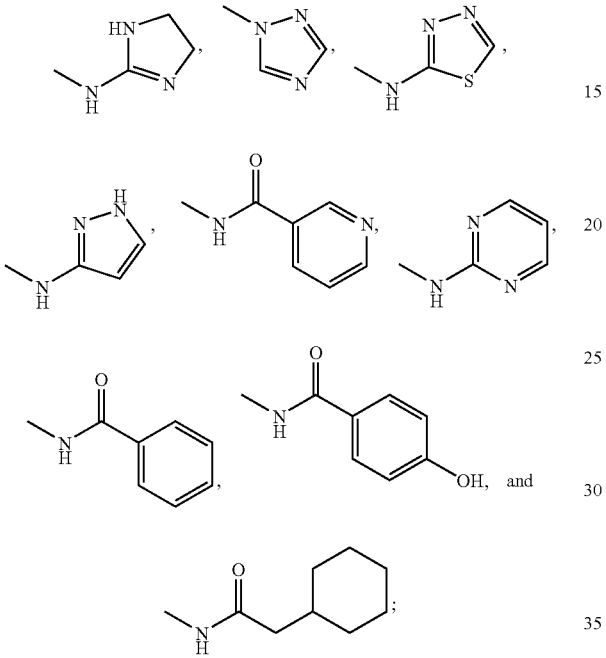

Q represents a substituted or unsubstituted aromatic carbocyclic ring;

$R_4$ is a $C_1$ to $C_6$ linear or branched chain or a $C_1$ to $C_6$ linear or branched chain with an aryl group;

$R_6$ is H, =O, =S or $-CH_3$;

$R_7$ is NH2, NH$-R_8$, or

$R_8$ is a $C_1$ to $C_6$ linear or branched chain or an amine capping group, and where there are two $R_8$ groups, each $R_8$ is independently a $C_1$ to $C_6$ linear or branched chain or an amine capping group, wherein the amine capping group is allyl, cyclopropane methyl, hexanoyl, heptanoyl, acetyl, propionoyl, butanoyl, phenylacetyl, cyclohexylacetyl, naphthylacetyl, cinnamoyl, phenyl, benzyl, benzoyl, 12-Ado, 7'-amino heptanoyl, 6-Ahx, Amc, 8-Aoc or polyethylene glycol with a formula molecular weight of between about 100 and about 10,000;

y is from 0 to 6;

z is from 0 to 6; and wherein the carbon atoms marked with an asterisk can have any stereochemical configuration.

12. The compound of claim 11 of formula

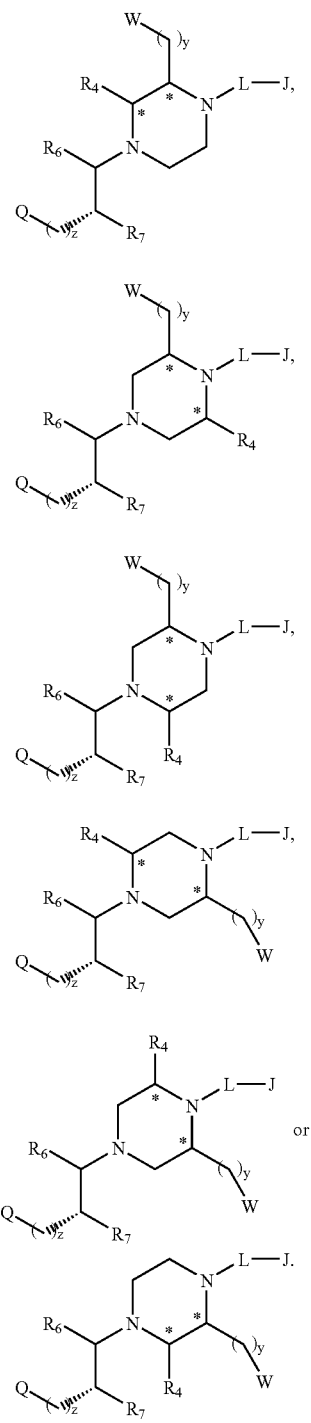

13. The compound of claim 11 wherein $R_6$ is $CH_3$,

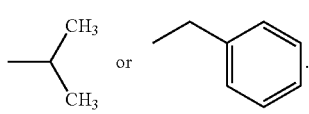

14. The compound of claim 11 wherein $R_6$ is H or =O.

15. The compound of claim 11 wherein $R_7$ is $NH_2$, $N(CH_3)_2$, $NHCH_3$,

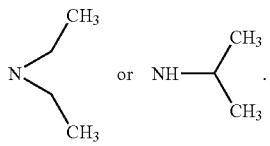

16. The compound of claim 11 wherein L is —$CH_2$—, —$(CH_2)_2$—, or —$(C=O)(CH_2)_2$—.

17. The compound of claim 11 wherein J is a substituted or unsubstituted ring structure selected from the group consisting of:

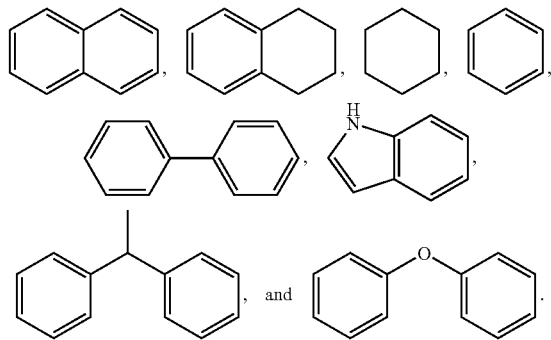

18. The compound of claim 17 wherein J is substituted at one or more positions with one or more hydroxyl, halogen, alkyl or aryl groups.

19. The compound of claim 11 wherein W is selected from the group consisting of —$NH_2$ and —$NH(C=NH)NH_2$.

20. The compound of claim 11 wherein Q is phenyl, substituted phenyl, naphthyl or substituted naphthyl.

21. The compound of claim 11 wherein Q is an indole, substituted indole, quinoline, substituted quinoline, isoquinoline or substituted isoquinoline.

22. The compound of claim 11 wherein Q is:

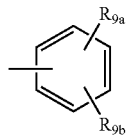

wherein $R_{9a}$ and $R_{9b}$ are optional ring substituents, and when one or both are present, are the same or different and independently hydroxyl, halogen, alkyl, or aryl groups attached directly or through an ether linkage.

23. A compound of formula V or VI:

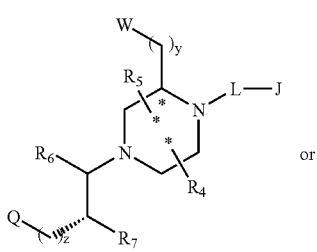

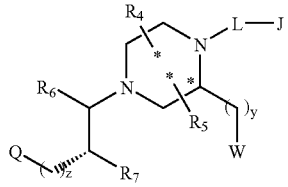

and pharmaceutically acceptable salts thereof;
wherein
J is a substituted or unsubstituted monocyclic or bicyclic ring structure, wherein in each instance the ring or rings have 5 or 6 ring atoms;
L is a linker selected from the group consisting of —$(CH_2)_q$—, —$(CH_2)_q$—O—, —$(CH_2)_q$—O—$(C=O)$—, —$CH_2)_q$—NH—, —$CH_2)_q$—NH—$(C=O)$—, —$CH_2)_q$—$C=O)$—NH—, —$(CH_2)_q$—$(C=O)$—O—, —NH—$(C=O)$—$(CH_2)_q$—, —$C=O)$—NH—$(CH_2)_q$—, —NH—$(CH_2)_q$—, —NH—$CH_2)_q$—O—, —$(C=O)(CH_2)_q$—, —$(CH_2)_q$—$(C=O)$— and —$(C=O)$—O—$(CH_2)_q$— q is from 0 to 6;

W is a cationic center, hydrogen bond donor or hydrogen bond acceptor selected from the group consisting of NH2, NH(C=NH)NH2, —NHCOCH$_3$, —CONHCH$_3$, —NH(C=NH)NHMe, —NH(C=NH)NHEt, —NH(C=NH)NHPr, —NH(C=NH)NHPr-I, —NH(C=NH)NH2, —NH(C=0)OCH$_3$, —NH(C=0)CH$_3$, —NH(C=0)NH2, —NH(C=0)NHCH$_3$,

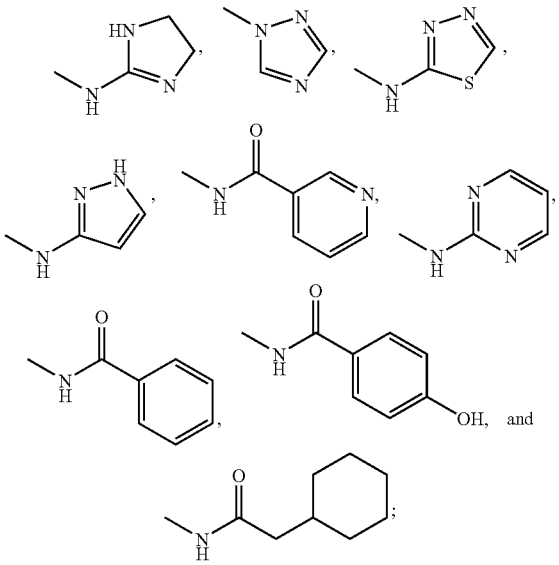

Q represents a substituted or unsubstituted aromatic carbocyclic ring;

$R_4$ and $R_5$ are each independently a $C_1$ to $C_6$ linear or branched chain or a $C_1$ to $C_6$ linear or branched chain with an aryl group;

$R_6$ is H, =O, =S or —$CH_3$;

$R_7$ is $NH_2$, NH—$R_8$, or

$R_8$ is a $C_1$ to $C_6$ linear or branched chain or an amine capping group, and where there are two $R_8$ groups, each $R_8$ is independently a $C_1$ to $C_6$ linear or branched chain or an amine capping group, wherein the amine capping group is allyl, cyclopropane methyl, hexanoyl, heptanoyl, acetyl, propionoyl, butanoyl, phenylacetyl, cyclohexylacetyl, naphthylacetyl, cinnamoyl, phenyl, benzyl, benzoyl, 12-Ado, 7'—amino heptanoyl, 6-Ahx, Ame, 8-Aoc or polyethylene glycol with a formula molecular weight of between about 100 and about 10,000;

y is from 0 to 6;

z is from 0 to 6; and wherein the carbon atoms marked with an asterisk can have any stereochemical configuration.

24. The compound of claim 23 of formula

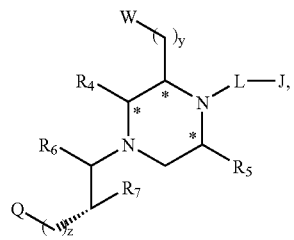

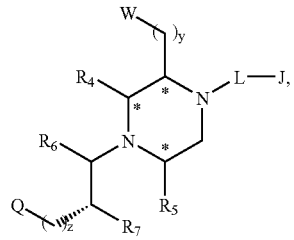

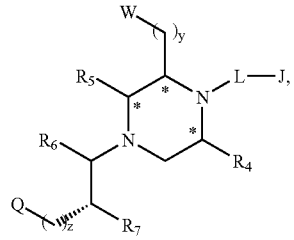

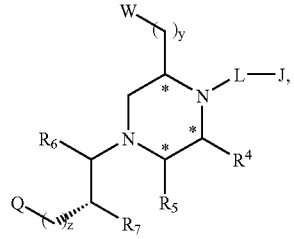

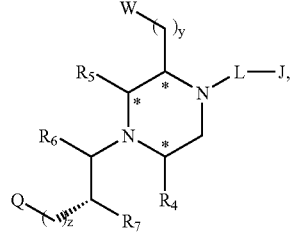

-continued

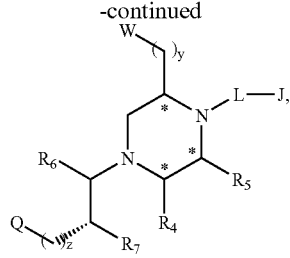

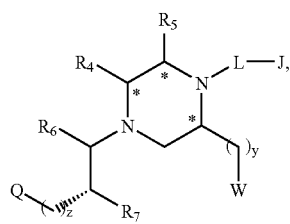

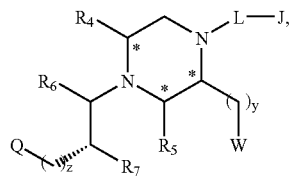

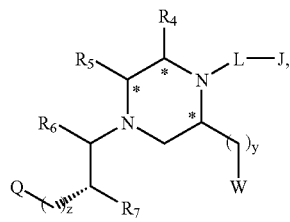

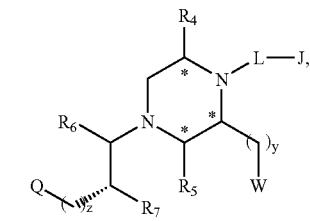

or

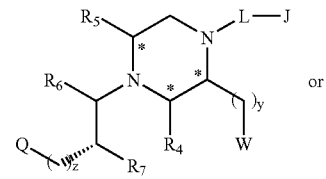

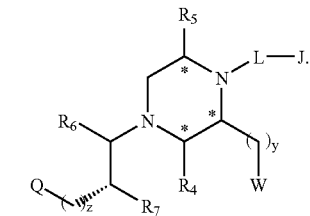

25. The compound of claim 23 wherein $R_4$ and $R_5$ are each independently

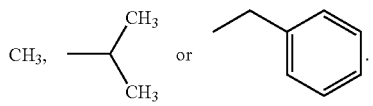

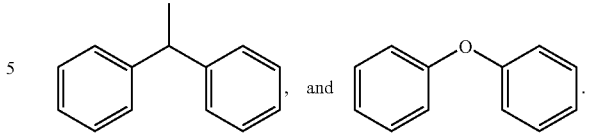, and 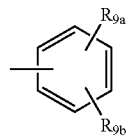.

26. The compound of claim 23 wherein $R_6$ is H or =O.

27. The compound of claim 23 wherein $R_7$ is NH2, N(CH$_3$)$_2$, NHCH$_3$,

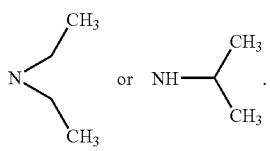

28. The compound of claim 23 wherein L is —CH$_2$—, —(CH$_2$)$_2$—, or —(C=O)(CH$_2$)$_2$—.

29. The compound of claim 23 wherein J is a substituted or unsubstituted ring structure selected from the group consisting of:

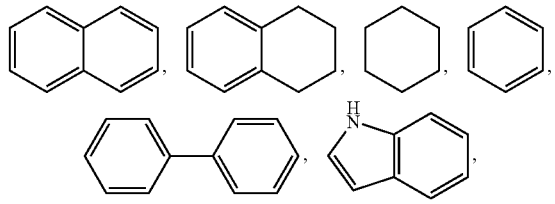

30. The compound of claim 29 wherein J is substituted at one or more positions with one or more hydroxyl, halogen, alkyl or aryl groups.

31. The compound of claim 23 wherein W is selected from the group consisting of —NH$_2$ and —NH(C=NH)NH$_2$.

32. The compound of claim 23 wherein Q is phenyl, substituted phenyl, naphthyl or substituted naphthyl.

33. The compound of claim 23 wherein Q is an indole, substituted indole, quinoline, substituted quinoline, isoquinoline or substituted isoquinoline.

34. The compound of claim 23 wherein Q is:

wherein $R_{9a}$ and $R_{9b}$ are optional ring substituents, and when one or both are present, are the same or different and independently hydroxyl, halogen, alkyl, or aryl groups attached directly or through an ether linkage.

* * * * *

UNITED STATES PATENT AND TRADEMARK OFFICE
CERTIFICATE OF CORRECTION

| | | |
|---|---|---|
| PATENT NO. | : 7,718,802 B2 | Page 1 of 1 |
| APPLICATION NO. | : 11/099814 | |
| DATED | : May 18, 2010 | |
| INVENTOR(S) | : Shubh D. Sharma et al. | |

It is certified that error appears in the above-identified patent and that said Letters Patent is hereby corrected as shown below:

Claim 1, column 69, line 40, delete "NH2" and replace with --$NH_2$--.

Claim 11, column 70, delete line 64, and replace with -- -NH-(C=O)-$(CH_2)_q$-, -(C=O)-NH-$(CH_2)_q$-,--.

Claim 11, column 71, line 44, delete "NH2" and replace with --$NH_2$--.

Claim 13, column 72, line 59, delete "$R_6$" and replace with --$R_4$--.

Claim 23, column 74, delete lines 16 through 23 and replace with --L is a linker selected from the group consisting of -$(CH_2)_q$-, -$(CH_2)_q$-O-, -$(CH_2)_q$-O-(C=O)-, -$(CH_2)_q$-NH-, -$(CH_2)_q$-NH-(C=O)-, -$(CH_2)_q$-(C=O)-NH-, -$(CH_2)_q$-(C=O)-O-, -NH-(C=O)-$(CH_2)_q$-, -(C=O)-NH-$(CH_2)_q$-, -NH-$(CH_2)_q$-, -NH-$(CH_2)_q$-O-, -(C=O)$(CH_2)_q$-, -$(CH_2)_q$-(C=O)- and -(C=O)-O-$(CH_2)_q$- --.

Claim 23, column 74, delete lines 27 through 31 and replace with --$NH_2$, NH(C=NH)$NH_2$, -NHCOCH_3, -CONHCH_3, -NH(C=NH)NHMe, -NH(C=NH)NHEt, -NH(C=NH)NHPr, -NH(C=NH)NHPr-l, -NH(C=NH)$NH_2$, -NH(C=O)OCH_3, -NH(C=O)CH_3, -NH(C=O)$NH_2$, -NH(C=O)NHCH_3,--.

Claim 23, column 75, line 10, delete "Ame" and replace with --Amc--.

Claim 27, column 77, line 11, delete "NH2" and replace with --$NH_2$--.

Signed and Sealed this

Twenty-second Day of June, 2010

David J. Kappos
*Director of the United States Patent and Trademark Office*